United States Patent
Abeywardane et al.

(10) Patent No.: US 8,063,094 B2
(45) Date of Patent: Nov. 22, 2011

(54) ANTI-CYTOKINE HETEROCYCLIC COMPOUNDS

(75) Inventors: Asitha Abeywardane, Danbury, CT (US); Denise Andersen, Montara, CA (US); Tina Marie Morwick, New Milford, CT (US); Roger John Snow, Danbury, CT (US); Yancey David Ward, Sandy Hook, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 12/526,144

(22) PCT Filed: Feb. 7, 2008

(86) PCT No.: PCT/US2008/053243
§ 371 (c)(1),
(2), (4) Date: Nov. 11, 2010

(87) PCT Pub. No.: WO2008/098096
PCT Pub. Date: Aug. 14, 2008

(65) Prior Publication Data
US 2011/0053955 A1 Mar. 3, 2011

Related U.S. Application Data

(60) Provisional application No. 60/888,779, filed on Feb. 8, 2007.

(51) Int. Cl.
*A61K 31/4045* (2006.01)
*C07D 209/16* (2006.01)
(52) U.S. Cl. .......................... 514/419; 548/491
(58) Field of Classification Search .................. 514/419; 548/491
See application file for complete search history.

(56) References Cited

U.S. PATENT DOCUMENTS

| | | | | |
|---|---|---|---|---|
| 3,216,898 A | * | 11/1965 | Fellows | 514/415 |
| 4,428,877 A | * | 1/1984 | Szantay et al. | 540/520 |
| 4,839,377 A | | 6/1989 | Bays et al. | |
| 6,821,966 B2 | | 11/2004 | Dugar et al. | |
| 6,906,067 B2 | | 6/2005 | Moriarty et al. | |
| 7,169,925 B2 | | 1/2007 | Merriman et al. | |
| 2006/0183906 A1 | | 8/2006 | Rodgers et al. | |
| 2006/0276496 A1 | * | 12/2006 | Goldberg et al. | 514/291 |

FOREIGN PATENT DOCUMENTS

GB 888.426 * 4/1958

OTHER PUBLICATIONS

Bradham et al, p38 MAPK in Development and Cancer, Cell Cycle, 2006, vol. 5:8, p. 824-828.*
Evgen'ev et al, Flow-Injection Determination of Indole Derivatives in Pharmaceutical Mixtures, Journal of Analytical Chemistry, 2006, vol. 6, No. 7, p. 694-701.*
Golub et al, Molecular Classification of Cancer: Class Discovery and Class Prediction by Gene Expression Monitoring, Science, 1999, vol. 286, p. 531-537.*
King, Role of Inflammatory Cytokines in Diabetes and Its Complications, J. Periodontol, Jun. 2008, vol. 79, p. 1527-1534.*
Medical News: Inflammatory Cytokines Linked to Alzheimers Disease, http://www.medpagetoday.com/Neurology/Alzheimers Disease/5796, accessed Apr. 26, 2011.*
Moya et al, Synthesis of 7-fluoro- and 6,7-difluoroserotonin and 7-fluoro- and 6,7-difluoromelatonin, Journal of Fluorine Chemistry, 2006, vol. 127, p. 1256-1260.*
Shioi et al, Proinflammatory Cytokine Inhibitor Prolongs Survival of Rats with Heart Failure Induced by Pressure Overload, Jpn Circ J, 2001, vol. 65, p. 584-585.*
Targeted Cancer Therapies, http://www.cancer.gov/cancertopics/factsheet/therapy/targeted, accessed Jan. 12, 2011.*
Zenvirt et al, Status of p53 in human cancer cells does not predict efficacy of CHK1 kinase inhibitors combined with chemotherapeutic agents, Oncogene, 2010, vol. 29, p. 6149-6159.*

* cited by examiner

*Primary Examiner* — Andrew D Kosar
*Assistant Examiner* — Karen Cheng
(74) *Attorney, Agent, or Firm* — Michael P. Morris; Edward S. Lazer

(57) ABSTRACT

Heterocyclic compounds which are inhibitors of Mitrogen-Activated Protein Kinase-Activated Protein Kinase-2 (MAP-KAP-K2) as described, in addition to their use in the treatment of cytokine mediated diseases.

4 Claims, No Drawings

ANTI-CYTOKINE HETEROCYCLIC COMPOUNDS

This application is the national phase entry under 35 U.S.C. §371 of International Application No. PCT/US2008/053243, filed Feb. 7, 2008, which claims priority to U.S. Provisional Application No. 60/888,779, filed Feb. 8, 2007, each of which is hereby incorporated by reference in its entirety.

BACKGROUND OF THE INVENTION

1. Field of the Invention

This present invention relates to heterocyclic compounds and analogues thereof and their use as inhibitors of Mitogen-Activated Protein Kinase-Activated Protein kinase-2 (MAP-KAP-k2). The present invention also related to a method for preventing or treating a disease or disorder that can be treated or prevented by modulating the activity of MAPKAP-K2 in a subject, and to pharmaceutical compositions and kits that include these MAPKAP-K2 inhibitors.

2. Description of Related Art

Mitogen Activated Protein Kinases (MAPKs) are members of signal transduction pathways that change cell physiology in response to external stimuli by activating a variety of downstream signaling genes products. These gene products control diverse cellular functions such as the production of pro-inflammatory cytokines involved in establishing and maintaining specific human diseases. The MAPKs are activated by phosphorylation on specific residues within the activation loop sequence by specific upstream MAPK kinases (MKKs) in response to a cellular activation signal. In turn, the MAPKs activate a variety of downstream gene products. There are four major classes of MAPKs: 1) the archetypal Extracellular Regulated kinases (ERKs), 2) the c-jun N-terminal kinases (JNKs), 3) the p38 MAPKs and finally, 4) the ERK5 or BigMAPKs. The MAPK pathways are involved in alterations in cell physiology resulting from cell stimulation. They control various cell processes such as: cell death, cell cycle machinery, gene transcription and protein translation.

Of particular relevance to this invention is the p38 MAPK family (also known as p38, SAPK2a, RK, MPK2, Mxi2 and CSBP). These kinases, most notably the p38alpha and p38beta isoforms, can activate a wide variety of regulatory proteins. In this manner, p38 can diversify downstream signaling leading to a wide variety of cellular outcomes. Central to the signal transduction process initiated by p38 activation is MAPKAP-K2. Most of the physiological outcomes of MAPKAP-K2 have been established using mice genetically deficient in MAPKAP-K2 (designated MAPKAP-K2$^{(-/-)}$). A significant phenotype of the MAPKAP-K2$^{(-/-)}$ mice is that pro-inflammatory cytokine production is inhibited following stimulation of splenocytes with lipopolysaccharide (LPS). Specifically, the production of tumor necrosis factor-alpha (TNF-alpha) is blocked by 92%, interleukin-1beta (IL-1-beta) is blocked by 40%, IL-6 is blocked by 87% and interferon-gamma (IFN-gamma) is blocked by 86%. This phenotype cannot be rescued by the expression of a kinase dead MAPKAP-K2 mutant, indicating that the kinase function of MAPKAP-K2 is required for proinflammatory cytokine production. Thus, an inhibitor of MAPKAP-K2 kinase activity has the potential to exhibit the same inhibitory effects on the production of proinflammatory cytokines.

MK2 activates a number of substrates, including the mRNA binding protein, tristetraproline (TTP). TTP expression is induced by proinflammatory stimuli such as lipopolysaccharide (LPS) or tumor necrosis factor-alpha (TNF-alpha). TTP binds to the AU-rich element within the 3'-untranslated region of the TNF-alpha transcript resulting in a decrease in TNF-alpha mRNA stability. TTP$^{(-/-)}$ mice exhibit many defects including arthritis and systemic lupus erythematosis-like symptoms presumably resulting from an increase in circulating TNF-alpha levels. Data from in vivo studies with MK2$^{(-/-)}$ indicate that the repressive effects of TTP on both TNF-alpha and interleukin-6 (IL-6) production are downstream of MK2 further establishing p38-MK2-TTP as a critical signaling sequence for the production of proinflammatory cytokines.

Elevated levels of proinflammatory cytokines are associated with a number of diseases such as toxic shock syndrome, rheumatoid arthritis, osteoarthritis, diabetes and inflammatory bowel disease. In these diseases, chronic elevation of inflammation exacerbates or causes much of the pathophysiology observed. For example, rheumatoid synovial tissue becomes invaded with inflammatory cells that result in destruction to cartilage and bone. Studies suggest that inflammatory changes mediated by cytokines may be involved in endothelial cell pathogenesis including restenosis after percutaneous transluminal coronary angioplasty (PTCA). An important and accepted therapeutic approach for potential drug intervention in these diseases is the reduction of pro-inflammatory cytokines such as TNF-alpha and IL-1-beta. Several biological agents directed against these pro-inflammatory cytokines (anti-TNF antibodies, a soluble TNF receptor and an IL-1 receptor antagonist) have been FDA approved for the treatment of RA, Crohn's disease and psoriatic arthritis; Abbott Laboratories markets HUMIRA® (Adalimumab) for the treatment of rheumatoid arthritis (RA).

A soluble TNF-alpha receptor has been engineered that interacts with TNF-alpha. The approach is similar to that described above for the monoclonal antibodies directed against TNF-alpha; both agents bind to soluble TNF-alpha, thus reducing its concentration. One version of this construct, Enbrel® (Immunex, Seattle, Wash.), is marketed for the treatment of rheumatoid arthritis, psoriasis, ankylosing spondylitis, and psoriatic arthritis. Another version of the TNF-alpha receptor, Ro 45-2081 (Hoffman-LaRoche Inc., Nutley, N.J.) has demonstrated efficacy in various animal models of allergic lung inflammation and acute lung injury. Ro 45-2081 is a recombinant chimeric molecule constructed from the soluble 55 kDa human TNF receptor fused to the hinge region of the heavy chain IgG1 gene and expressed in eukaryotic cells.

Proinflammatory cytokines such as TNF-alpha and IL-6 are also important mediators of septic shock and associated cardiopulmonary dysfunction, acute respiratory distress syndrome (ARDS) and multiple organ failure. In a study of patients presenting with sepsis, a correlation was found between TNF-alpha and IL-6 levels and septic complications. TNFα has also been implicated in cachexia and muscle degradation, associated with HIV infection. Obesity is associated with an increase incidence of infection, diabetes and cardiovascular disease. Abnormalities in TNF-alpha expression have been noted for each of the above conditions. It has been proposed that elevated levels of TNF-alpha are involved in other eating related disorders such as anorexia and bulimia nervosa. Pathophysiological parallels are drawn between anorexia nervosa and cancer cachexia. An inhibitor of TNF-alpha production, HU-211, was shown to improve the outcome of closed brain injury in an experimental model. Atherosclerosis is known to have an inflammatory component and cytokines such as IL-1 and TNF have been suggested to promote the disease. In an animal model an IL-1 receptor antagonist was shown to inhibit fatty streak formation.

TNF-alpha levels are elevated in airways of patients with chronic obstructive pulmonary disease and it may contribute to the pathogenesis of this disease. Circulating TNFα may also contribute to weight loss associated with this disease. Elevated TNF-alpha levels have also been found to be associated with congestive heart failure and the level has been correlated with severity of the disease. In addition, TNF-alpha has been implicated in reperfusion injury in lung, kidney, and the nervous system. TNF-alpha is also a potent osteoclastogenic agent and is involved in bone resorption and diseases involving bone resorption. It has also been found highly expressed in chondrocytes of patients with traumatic arthritis. TNF-alpha has also been shown to play a key role in the development of glomerulonephritis.

The proinflammatory cytokine IL-6 has been implicated with the acute phase response. IL-6 is a growth factor in a number in oncological diseases including multiple myeloma and related plasma cell dyscrasias. It has also been shown to be an important mediator of inflammation within the central nervous system. Elevated levels of IL-6 are found in several neurological disorders including AIDS dementia complex, Alzheimer's disease, multiple sclerosis, systemic lupus erythematosus, CNS trauma and viral and bacterial meningitis. IL-6 also plays a significant role in osteoporosis. In murine models it has been shown to effect bone resorption and to induce osteoclast activity. Marked cytokine differences, such as IL-6 levels, exist in vivo between osteoclasts of normal bone and bone from patients with Paget's disease. A number of cytokines have been shown to be involved in cancer cachexia. The severity of key parameters of cachexia can be reduced by treatment with anti IL-6 antibodies or with IL-6 receptor antagonists. Several infectious diseases, such as influenza, indicate IL-6 and IFN alpha as key factors in both symptom formation and in host defense. Overexpression of IL-6 has been implicated in the pathology of a number of diseases including multiple myeloma, rheumatoid arthritis, Castleman's disease, psoriasis, post-menopausal osteoporosis and juvenile idiopathic arthritis. Compounds that interfered with the production of cytokines including IL-6, and TNF were effective in blocking a passive cutaneous anaphylaxis in mice. More recently, a humanized antibody directed against the IL-6 receptor, demonstrated efficacy in a randomized double-blind pilot human clinical study by significantly reducing the Crohn's disease activity index.

IFN-gamma has been implicated in a number of diseases. It has been associated with increased collagen deposition that is a central histopathological feature of graft-versus-host disease. Following kidney transplantation, a patient was diagnosed with acute myelogenous leukemia. Retrospective analysis of peripheral blood cytokines revealed elevated levels of GM-CSF and IFN-gamma. These elevated levels coincided with a rise in peripheral blood white cell count. The development of insulin-dependent diabetes (Type 1) can be correlated with the accumulation in pancreatic islet cells of T-cells producing IFN-gamma. IFN-gamma along with TNF, IL-2 and IL-6 lead to the activation of most peripheral T-cells prior to the development of lesions in the central nervous system for diseases such as multiple sclerosis (MS) and AIDS dementia complex. Atherosclerotic lesions result in arterial disease that can lead to cardiac and cerebral infarction. Many activated immune cells are present in these lesions, mainly T-cells and macrophages. These cells produce large amounts of proinflammatory cytokines such as TNF, IL-1 and IFN-gamma. These cytokines are thought to be involved in promoting apoptosis or programmed cell death of the surrounding vascular smooth muscle cells resulting in the atherosclerotic lesions. Allergic subjects produce mRNA specific for IFN-gamma following challenge with Vespula venom. The expression of a number of cytokines, including IFN-gamma has been shown to increase following a delayed type hypersensitivity reaction thus indicating a role for IFN-gamma in atopic dermatitis. Histopathologic and immunohistologic studies were performed in cases of fatal cerebral malaria. Evidence for elevated IFN-gamma amongst other cytokines was observed indicating a role in this disease. The importance of free radical species in the pathogenesis of various infectious diseases has been established. The nitric oxide synthesis pathway is activated in response to infection with certain viruses via the induction of proinflammatory cytokines such as IFN-gamma. Patients, chronically infected with hepatitis B virus (HBV) can develop cirrhosis and hepatocellular carcinoma. Viral gene expression and replication in HBV transgenic mice can be suppressed by a post-transcriptional mechanism mediated by IFN-gamma, TNF and IL-2. IFN-gamma can selectively inhibit cytokine induced bone resorption. It appears to do this via the intermediacy of nitric oxide (NO) which is an important regulatory molecule in bone remodeling. NO may be involved as a mediator of bone disease for such diseases as: rheumatoid arthritis, tumor associated osteolysis and postmenopausal osteoporosis. Studies with gene deficient mice have demonstrated that the IL-12 dependent production of IFN-gamma is critical in the control of early parasitic growth. Although this process is independent of nitric oxide the control of chronic infection does appear to be NO dependent. NO is an important vasodilator and convincing evidence exists for its role in cardiovascular shock. IFN-gamma is required for progression of chronic intestinal inflammation in such diseases as Crohn's disease and inflammatory bowel disease (IBD) presumably through the intermediacy of CD4+ lymphocytes probably of the TH1 phenotype. An elevated level of serum IgE is associated with various atopic diseases such as bronchial asthma and atopic dermatitis. The level of IFN-gamma was negatively correlated with serum IgE suggesting a role for IFNgamma in atopic patients.

The proinflammatory cytokine, IL-1-beta, is partially controlled by MAPKAP-k2. Hence, inhibition of MAPKAP-k2 may impact IL-1-beta dependent processes. IL-1 has been implicated as an immunological effector molecule in a large number of disease processes. IL-1 receptor antagonist (IL-1ra) had been examined in human clinical trials. Efficacy has been demonstrated for the treatment of rheumatoid arthritis. In a phase III human clinical trial IL-1ra reduced the mortality rate in patients with septic shock syndrome. Several other diseases affected by IL-1 include Adult Onset Still's disease, macrophage auto-activation syndromes, Muckle-Wells syndrome, Familial Cold Autoinflammatory Syndrome and Neonatal Onset Multisystem Inflammatory Disease. Patients with Muckle-Wells syndrome exhibiting systemic inflammation were treated with anakinra (IL-1ra), leukocytosis serum amyloid A, C-reactive protein and local inflammatory arthritis were reduced with a few days demonstrating that systemic inflammation is IL-1 mediated. Osteoarthritis is a slow progressive disease characterized by destruction of the articular cartilage. IL-1 is detected in synovial fluid and in the cartilage matrix of osteoarthritic joints. Antagonists of IL-1 have been shown to diminish the degradation of cartilage matrix components in a variety of experimental models of arthritis. Nitric oxide (NO) is a mediator of cardiovascular homeostasis, neurotransmission and immune function; recently it has been shown to have important effects in the modulation of bone remodeling. Cytokines such as IL-1 and TNF are potent stimulators of NO production. NO is an important regulatory molecule in bone with effects on cells of the osteoblast and osteoclast lineage. The promotion of beta-cell destruction leading to insulin dependent diabetes mellitus shows dependence on IL-1. Some of this damage may be mediated through other effectors such as prostaglandins and thromboxanes. IL-1 can effect this process by controlling the level of both cyclooxygenase II and inducible nitric oxide synthetase expression.

Inhibitors of cytokine production are expected to block inducible cyclooxygenase (COX-2) expression. COX-2 expression has been shown to be increased by cytokines and it is believed to be the isoform of cyclooxygenase responsible for inflammation. Accordingly, inhibitors of MAPKAP-k2 reducing the production of cytokines such as IL-1, would be expected to exhibit efficacy against those disorders currently treated with COX inhibitors such as the familiar NSAIDs. These disorders include acute and chronic pain as well as symptoms of inflammation and cardiovascular disease.

Elevation of several cytokines has been demonstrated during active inflammatory bowel disease (IBD). A mucosal imbalance of intestinal IL-1 and IL-1ra is present in patients with IBD. Insufficient production of endogenous IL-1ra may contribute to the pathogenesis of IBD. Alzheimer disease is characterized by the presence of beta-amyloid protein deposits, neurofibrillary tangles and cholinergic dysfunction throughout the hippocampal region. The structural and metabolic damage found in Alzheimer disease is possibly due to a sustained elevation of IL-1. A role for IL-1 in the pathogenesis of human immunodeficiency virus (HIV) has been identified. IL-1ra showed a clear relationship to acute inflammatory events as well as to the different disease stages in the pathophysiology of HIV infection. IL-1 and TNF are both involved in periodontal disease. The destructive process associated with periodontal disease may be due to a disregulation of both IL-1 and TNF.

IL-1 has also been shown to induce uveitis in rats which could be inhibited with IL-1 blockers. Cytokines including IL-1, TNF and GM-CSF have been shown to stimulate proliferation of acute myelogenous leukemia blasts. IL-1 was shown to be essential for the development of both irritant and allergic contact dermatitis. Epicutaneous sensitization can be prevented by the administration of an anti-IL-1 monoclonal antibody before epicutaneous application of an allergen. Data obtained from IL-1 knock out mice indicates the critical involvement in fever for this cytokine A variety of cytokines including TNF, IL-1, IL-6 and IL-8 initiate the acute-phase reaction which is stereotyped in fever, malaise, myalgia, headaches, cellular hypermetabolism and multiple endocrine and enzyme responses. The production of these inflammatory cytokines rapidly follows trauma or pathogenic organism invasion.

This application discloses compounds that have the ability to inhibit TNF-alpha. Compounds disclosed herein are indicated to be effective in treating the following diseases: Rheumatoid arthritis, psoriasis, crohn's disease, dementia associated with HIV infection, glaucoma, optic-neuropathy, optic neuritis, retinal ischemia, laser induced optic damage, surgery or trauma-induced proliferative vitreoretinopathy, cerebral ischemia, hypoxia-ischemia, hypoglycemia, domoic acid poisoning, anoxia, carbon monoxide or manganese or cyanide poisoning, Huntington's disease, Alzheimer's disease, Parkinson's disease, meningitis, multiple sclerosis and other demyelinating diseases, amyotrophic lateral sclerosis, head and spinal cord trauma, seizures, convulsions, olivopontocerebellar atrophy, neuropathic pain syndromes, diabetic neuropathy, HIV-related neuropathy, MERRF and MELAS syndromes, Leber's disease, Wernicke's encephalopathy, Rett syndrome, homocysteinuria, hyperprolinemia, hyperhomocysteinemia, nonketotic hyperglycinemia, hydroxybutyric aminoaciduria, sulfite oxidase deficiency, combined systems disease, lead encephalopathy, Tourett's syndrome, hepatic encephalopathy, drug addiction, drug tolerance, drug dependency, depression, anxiety and schizophrenia. In addition, compounds disclosed herein are useful for treating acute and chronic inflammation in the lung caused by inhalation of smoke such as cigarette smoke. TNF-alpha anatagonists are apparently also useful for the treatment of endometriosis, see EP 1022027 A1, as well as rheumatoid arthritis, psoriasis, ankylosing spondylitis, and psoriatic arthritis. The p38MAP kinase pathway plays an role in *B. burgdorferi*-elicited inflammation and may be useful in treating inflammation induced by the Lyme disease agent.

As noted above, inhibition of cytokine production will be beneficial in the treatment of cytokine mediated diseases. Therefore a need exists for small molecule inhibitors for treating these diseases with optimized efficacy, pharmacokinetic and safety profiles.

BRIEF SUMMARY OF THE INVENTION

Inhibition of MAPKAP-k2 will be beneficial in the treatment of various disease states.

Compounds of formula I:

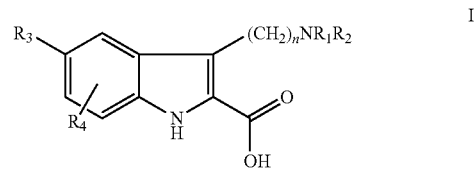

wherein $R^1$-$R^4$ and n are defined below, have been discovered, and such compounds inhibit the activity of MAPKAP-k2.

It is a further object of the invention to provide methods for treating MAPKAP-k2 mediated diseases and pathological conditions involving inflammation such as chronic inflammatory disease, using the novel compounds of the invention.

It is yet a further object of the invention to provide processes of preparation of the above-mentioned novel compounds.

DETAILED SUMMARY OF THE INVENTION

In an embodiment of the present invention, there is provided a compound, salt, isomer, or product thereof that is effective for treating or preventing a disease or disorder in a subject, which diseases or disorders can be treated or prevented by inhibiting the activity of MAPKAP-ak2, wherein the compound has the structure:

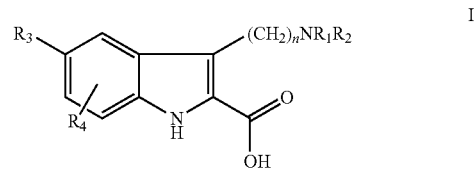

wherein:
$R_1$ and $R_2$ are H or $C_{1-3}$alkyl;
$R_3$ is chosen from
halogen, $C_{1-3}$alkoxy, benzyloxy, —NHC(O)OCH$_2$phenyl, —NHC(O)phenyl, —NHC(O)NH$_2$, phenyl optionally substituted with 1 to 3 halogens, $C_{1-3}$alkyl or $C_{1-3}$alkoxy, or $R_3$ is —C(O)NR$_5$R$_6$
wherein
$R_5$ is chosen from hydrogen, $C_{1-6}$ alkyl, $C_{2-6}$ alkenyl, $C_{2-6}$ alkynyl, $C_{1-6}$ alkoxy, or $C_{3-7}$ cycloalkyl; and $R_6$ is chosen from hydrogen, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, hydroxy, $C_{3-7}$ cycloalkyl, heterocyclyl, aryl, aryloxy, acyl, heteroaryl, $C_{3-7}$ cycloalkyl-$C_{1-6}$ alkyl, aryl-$C_{1-6}$ alkyl, aryl-$C_{1-6}$ haloalkyl, heterocyclyl-$C_{1-6}$ alkyl, heteroaryl-$C_{1-6}$ alkyl, $C_{3-7}$ cycloalkyl-$C_{2-6}$ alkenyl, aryl-$C_{2-6}$ alkenyl, heterocyclyl-$C_{2-6}$ alkenyl, heteroaryl-$C_{2-6}$ alkenyl, di$C_{1-3}$alkylamino(CH$_2$)$_{2-4}$, or $C_{2-6}$ alkylthio, wherein the sulfur atom is optionally oxidized to a sulfoxide or sulfone; wherein each aryl, heterocycle or heteroaryl may be singly or multiply substituted with $R^y$, wherein $R^y$ may be chosen from:

halogen, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, hydroxy, $C_{3-7}$ cycloalkyl, heterocyclyl, aryl optionally substituted with $R^x$, aryloxy, acyl, heteroaryl optionally substituted with $R^x$, $C_{3-7}$ cycloalkyl-$C_{1-6}$ alkyl, aryl-$C_{1-6}$ alkyl, aryl-$C_{1-6}$ haloalkyl, aryl-$C_{1-6}$-aminoalkyl, heterocyclyl-$C_{1-6}$ alkyl, heteroaryl-$C_{1-6}$ alkyl, $C_{3-7}$ cycloalkyl-$C_{2-6}$ alkenyl, aryl-$C_{2-6}$ alkenyl, heterocyclyl-$C_{2-6}$ alkenyl, heteroaryl-$C_{2-6}$ alkenyl, $C_{2-6}$ alkylthio wherein the sulfur atom is optionally oxidized to a sulfoxide or sulfone, —OCF$_3$, amino, $C_{1-3}$alkylamino, di$C_{1-3}$alkylamino, acylamino, hydroxyethylamino, —CN, —CO$_2$C$_{1-3}$alkyl, —CH$_2$NH$_2$, —C(O)N(R$^a$)(R$^b$) where $R^a$ and $R^b$ are independently selected from H, $C_{1-3}$alkyl, —CH$_2$C(O)NH$_2$, —(CH$_2$)$_n$OH, —(CH$_2$)$_n$NR$^c$R$^d$, where n is 2 or 3 and $R^c$ and $R^d$ are independently selected from H, $C_{1-3}$alkyl and C(O)CH$_3$, or —C(O)NH—N=C—R$^e$, where $R^e$ is aryl or heteroaryl optionally substituted with $R^x$, or $R^a$ and $R^b$ together with the N they are connected to can form a pyrrolidine, piperazine, piperidine or morpholine ring optionally substituted with one to three groups selected from —CO$_2$C$_{1-3}$alkyl, —C(O)NH$_2$, —OH, $C_{1-3}$alkyl, amino, $C_{1-3}$alkylamino and di$C_{1-3}$alkylamino; or $R_5$ and $R_6$ can be taken together to form a cycloalkyl or heterocyclyl ring;

$R_4$ is selected from H, $C_{1-6}$alkyl, halogen and CF$_3$;

$R^x$ is selected from:

amino, $C_{1-6}$ alkyl, $C_{2-6}$ alkenyl, amino $C_{1-6}$ alkyl, hydroxy$C_{1-6}$ alkyl, cyano $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, hydroxy, $C_{3-7}$ cycloalkyl, heterocyclyl, aryl, aryloxy, acyl, heteroaryl, $C_{3-7}$ cycloalkyl-$C_{1-6}$ alkyl, aryl-$C_{1-6}$ alkyl, aryl-$C_{1-6}$ haloalkyl, heterocyclyl-$C_{1-6}$ alkyl, heteroaryl-$C_{1-6}$ alkyl, $C_{3-7}$ cycloalkyl-$C_{2-6}$ alkenyl, aryl-$C_{2-6}$ alkenyl, heterocyclyl-$C_{2-6}$ alkenyl, heteroaryl-$C_{2-6}$ alkenyl, carbonyl, carbamoyl, ureido, or $C_{2-6}$ alkylthio wherein the sulfur atom is oxidized to a sulfoxide or sulfone; and n is an integer selected from 2, 3 or 4.

In a second embodiment there are provided compounds of formula (I) as described above and wherein $R_1$ and $R_2$ are H;

$R_3$ is —C(O)NR$_5$R$_6$ wherein $R_5$ is chosen from hydrogen, $C_{1-6}$ alkyl, $C_{2-6}$ alkenyl, $C_{2-6}$ alkynyl, $C_{1-6}$ alkoxy, or $C_{3-7}$ cycloalkyl; and $R_6$ is chosen from hydrogen, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, hydroxy, $C_{3-7}$ cycloalkyl, heterocyclyl, aryl, aryloxy, acyl, heteroaryl, $C_{3-7}$ cycloalkyl-$C_{1-6}$ alkyl, aryl-$C_{1-6}$ alkyl, aryl-$C_{1-6}$ haloalkyl, heterocyclyl-$C_{1-6}$ alkyl, heteroaryl-$C_{1-6}$ alkyl, $C_{3-7}$ cycloalkyl-$C_{2-6}$ alkenyl, aryl-$C_{2-6}$ alkenyl, heterocyclyl-$C_{2-6}$ alkenyl, heteroaryl-$C_{2-6}$ alkenyl, di$C_{1-3}$alkylamino(CH$_2$)$_{2-4}$ or $C_{2-6}$ alkylthio, wherein the sulfur atom is optionally oxidized to a sulfoxide or sulfone; wherein each aryl, heterocycle or heteroaryl may be singly or multiply substituted with $R^y$, wherein $R^y$ may be chosen from:

halogen, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, hydroxy, $C_{3-7}$ cycloalkyl, heterocyclyl, aryl optionally substituted with $R^x$, aryloxy, acyl, heteroaryl optionally substituted with $R^x$, $C_{3-7}$ cycloalkyl-$C_{1-6}$ alkyl, aryl-$C_{1-6}$ alkyl, aryl-$C_{1-6}$ haloalkyl, aryl-$C_{1-6}$aminoalkyl, heterocyclyl-$C_{1-6}$ alkyl, heteroaryl-$C_{1-6}$ alkyl, $C_{3-7}$ cycloalkyl-$C_{2-6}$ alkenyl, aryl-$C_{2-6}$ alkenyl, heterocyclyl-$C_{2-6}$ alkenyl, heteroaryl-$C_{2-6}$ alkenyl, $C_{2-6}$ alkylthio wherein the sulfur atom is optionally oxidized to a sulfoxide or sulfone, —OCF$_3$, amino, $C_{1-3}$alkylamino, di$C_{1-3}$alkylamino, acylamino, hydroxyethylamino, —CN, —CO$_2$C$_{1-3}$alkyl, —CH$_2$NH$_2$, —C(O)N(R$^a$)(R$^b$) where $R^a$ and $R^b$ are independently selected from H, $C_{1-3}$alkyl, —CH$_2$C(O)NH$_2$, —(CH$_2$)$_n$OH, —(CH$_2$)$_n$NR$^c$R$^d$, and $R^c$ and $R^d$ are independently selected from H, $C_{1-3}$alkyl and C(O)CH$_3$, or —C(O)NH—N=C—R$^e$, where $R^e$ is aryl or heteroaryl optionally substituted with $R^x$, or $R^a$ and $R^b$ together with the N they are connected to can form a pyrrolidine, piperazine, piperidine or morpholine ring optionally substituted with one to three groups selected from —CO$_2$C$_{1-3}$alkyl, —C(O)NH$_2$, —OH, $C_{1-3}$alkyl, amino, $C_{1-3}$alkylamino and di$C_{1-3}$alkylamino; or $R_5$ and $R_6$ can be taken together to form a cycloalkyl or heterocyclyl ring;

$R_4$ is H;

$R^x$ is selected from:

hydrogen, amino, $C_{1-6}$ alkyl, $C_{2-6}$ alkenyl, amino $C_{1-6}$ alkyl, hydroxy $C_{1-6}$ alkyl, cyano $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, hydroxy, $C_{3-7}$ cycloalkyl, acyl, $C_{3-7}$ cycloalkyl-$C_{1-6}$ alkyl, $C_{3-7}$ cycloalkyl-$C_{2-6}$ alkenyl, carbonyl, carbamoyl, or —CO$_2$C$_{1-6}$alkyl; and n is 3.

In a third embodiment there are provided compounds of formula (I) as described above and wherein $R_1$ and $R_2$ are H;

$R_3$ is —C(O)NR$_5$R$_6$ wherein $R_5$ is hydrogen; and $R_6$ is chosen from hydrogen, $C_{1-6}$ alkyl, $C_{3-7}$ cycloalkyl, heterocyclyl, aryl, heteroaryl, $C_{3-7}$ cycloalkyl-$C_{1-6}$ alkyl, aryl-$C_{1-6}$ alkyl, heterocyclyl-$C_{1-6}$ alkyl, heteroaryl-$C_{1-6}$ alkyl, or (CH$_3$)$_2$NCH$_2$CH$_2$—, wherein each aryl, heterocycle or heteroaryl may be singly or multiply substituted with $R^y$, wherein $R^y$ may be chosen from:

halogen, $C_{1-6}$ alkyl, $C_{2-6}$ alkenyl, $C_{2-6}$ alkynyl, $C_{1-6}$ alkoxy, hydroxy, $C_{3-7}$ cycloalkyl, acyl, $C_{3-7}$ cycloalkyl-$C_{1-6}$ alkyl, aryl-$C_{1-6}$ alkyl, aryl-$C_{1-6}$aminoalkyl, heterocyclyl-$C_{1-6}$ alkyl, heteroaryl-$C_{1-6}$ alkyl, $C_{2-6}$ alkylthio wherein the sulfur atom is optionally oxidized to a sulfoxide or sulfone, —OCF$_3$, amino, $C_{1-3}$alkylamino, di$C_{1-3}$alkylamino, acylamino, hydroxyethylamino, —CN, —CO$_2$C$_{1-3}$alkyl, —CH$_2$NH$_2$, —C(O)N(R$^a$)(R$^b$) where $R^a$ and $R^b$ are independently selected from H, $C_{1-3}$alkyl, —CH$_2$C(O)NH$_2$, —(CH$_2$)$_n$OH, —(CH$_2$)$_n$NR$^c$R$^d$, and $R^c$ and $R^d$ are independently selected from H, $C_{1-3}$alkyl and C(O)CH$_3$;

$R_4$ is H;

$R^x$ is selected from:

hydrogen, amino, $C_{1-6}$ alkyl, $C_{2-6}$ alkenyl, amino $C_{1-6}$ alkyl, hydroxy $C_{1-6}$ alkyl, cyano $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, hydroxy, $C_{3-7}$ cycloalkyl, acyl, $C_{3-7}$ cycloalkyl-$C_{1-6}$ alkyl, $C_{3-7}$ cycloalkyl-$C_{2-6}$ alkenyl, carbonyl, carbamoyl, or —CO$_2$C$_{1-6}$alkyl; and n is 3.

The following are representative compounds of the invention which can be made according to the general schemes and working examples below:

| Name | Structure |
|---|---|
| 3-(3-Amino-propyl)-5-benzyloxy-1H-indole-2-carboxylic acid | ![structure] |
| 3-(3-Amino-propyl)-5-bromo-1H-indole-2-carboxylic acid | ![structure] |
| 3-(3-Amino-propyl)-5-methoxy-1H-indole-2-carboxylic acid | ![structure] |
| 3-(3-Amino-propyl)-5-(2-fluoro-phenyl)-1H-indole-2-carboxylic acid | ![structure] |
| 3-(3-Amino-propyl)-5-(3-fluoro-phenyl)-1H-indole-2-carboxylic acid | ![structure] |
| 3-(3-Amino-propyl)-5-(4-fluoro-phenyl)-1H-indole-2-carboxylic acid | ![structure] |
| 3-(3-Amino-propyl)-5-carbamoyl-1H-indole-2-carboxylic acid | ![structure] |

-continued
| Name | Structure |
|---|---|
| 3-(3-Amino-propyl)-5-benzyloxycarbonylamino-1H-indole-2-carboxylic acid | 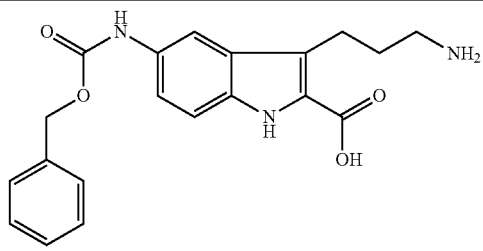 |
| 3-(3-Amino-propyl)-5-benzoylamino-1H-indole-2-carboxylic acid | 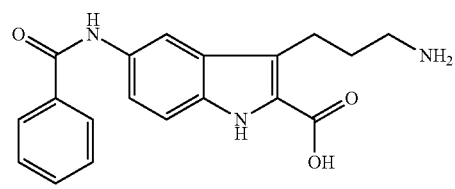 |
| 3-(3-Amino-propyl)-5-ureido-1H-indole-2-carboxylic acid | 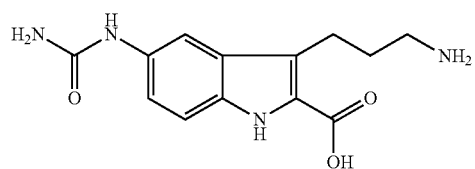 |
| 3-(3-Amino-propyl)-5-phenyl-1H-indole-2-carboxylic acid | 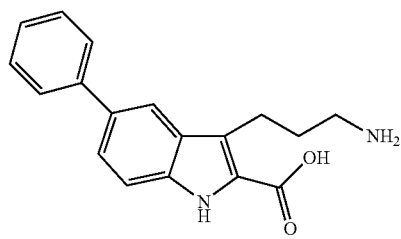 |
| 3-(3-Amino-propyl)-5-methylcarbamoyl-1H-indole-2-carboxylic acid | 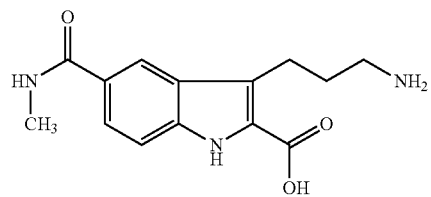 |
| 3-(3-Amino-propyl)-5-phenylcarbamoyl-1H-indole-2-carboxylic acid | 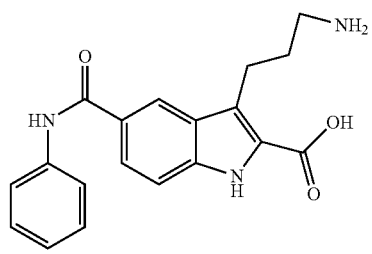 |

-continued

| Name | Structure |
|---|---|
| 3-(3-Amino-propyl)-5-phenethylcarbamoyl-1H-indole-2-carboxylic acid | 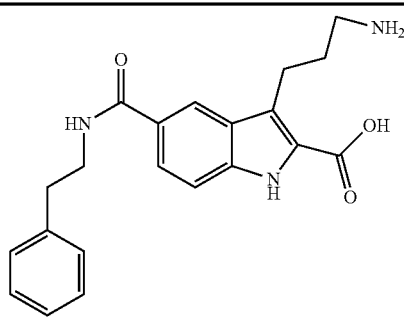 |
| 3-(3-Amino-propyl)-5-propylcarbamoyl-1H-indole-2-carboxylic acid | 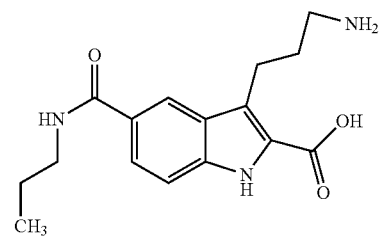 |
| 3-(3-Amino-propyl)-5 p-tolylcarbamoyl-1H-indole-2-carboxylic acid | 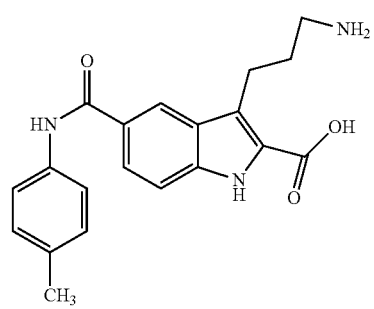 |
| 3-(3-Amino-propyl)-5-m-tolylcarbamoyl-1H-indole-2-carboxylic acid | 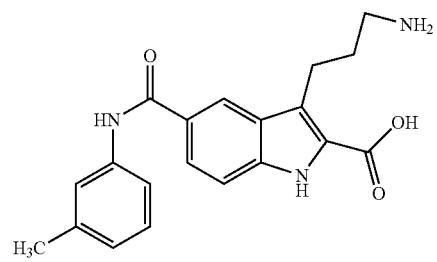 |
| 3-(3-Amino-propyl)-5-o-tolylcarbamoyl-1H-indole-2-carboxylic acid | 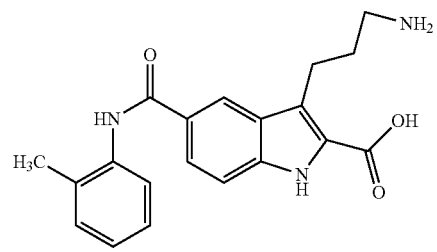 |
| 3-(3-Amino-propyl)-5-(2-dimethylamino-ethylcarbamoyl)-1H-indole-2-carboxylic acid | 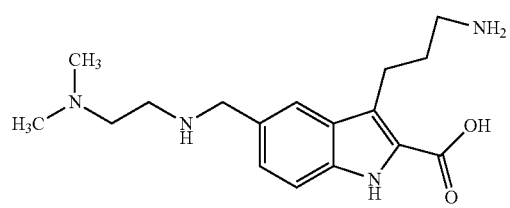 |

-continued
| Name | Structure |
|---|---|
| 3-(3-Amino-propyl)-5-(3-methoxy-phenylcarbamoyl)-1H-indole-2-carboxylic acid | 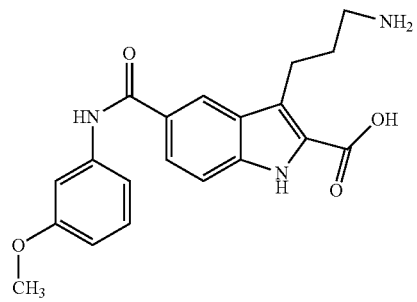 |
| 3-(3-Amino-propyl)-5-(4-methoxy-phenylcarbamoyl)-1H-indole-2-carboxylic acid | 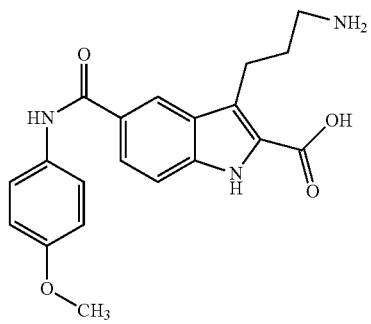 |
| 3-(3-Amino-propyl)-5-(4-isopropyl-phenylcarbamoyl)-1H-indole-2-carboxylic acid | 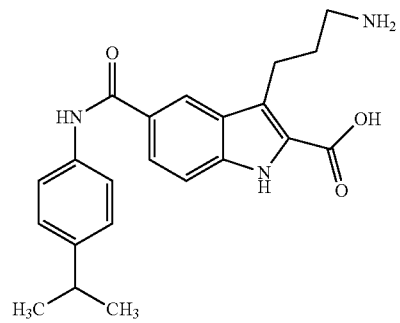 |
| 3-(3-Amino-propyl)-5-(indan-5-ylcarbamoyl)-1H-indole-2-carboxylic acid | 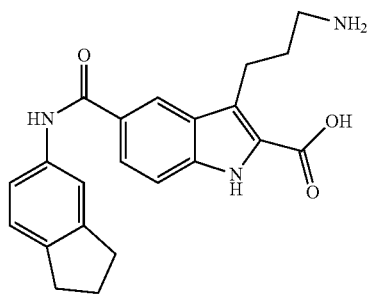 |
| 3-(3-Amino-propyl)-5-(3,4-dimethyl-phenylcarbamoyl)-1H-indole-2-carboxylic acid | 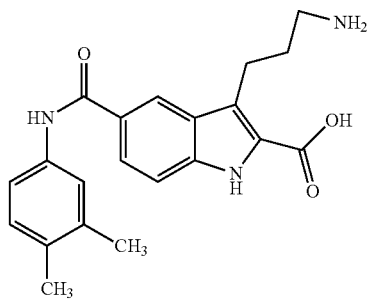 |

-continued

| Name | Structure |
|---|---|
| 5-Carbamoyl-3-(3-methylamino-propyl)-1H-indole-2-carboxylic acid | 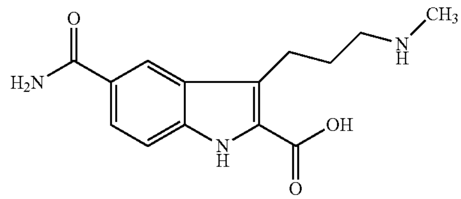 |
| 3-(3-Amino-propyl)-5-(pyridin-3-ylcarbamoyl)-1H-indole-2-carboxylic acid | 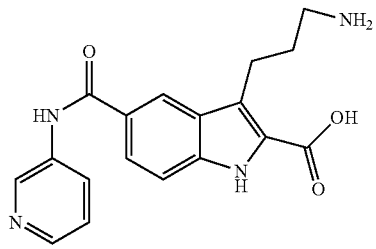 |
| 3-(3-Amino-propyl)-5-(pyridin-4-ylcarbamoyl)-1H-indole-2-carboxylic acid | 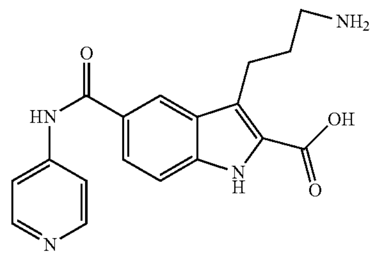 |
| 3-(3-Amino-propyl)-5-(3-bromo-phenylcarbamoyl)-1H-indole-2-carboxylic acid | 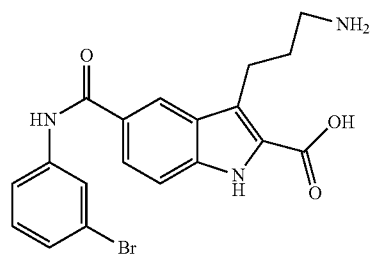 |
| 3-(3-Amino-propyl)-5-(4-bromo-phenylcarbamoyl)-1H-indole-2-carboxylic acid | 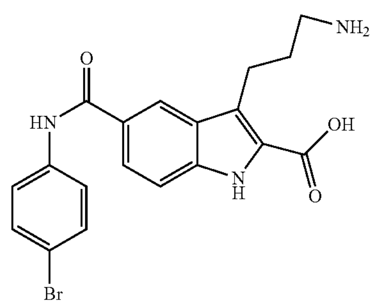 |
| 3-(3-Amino-propyl)-5-[4-(pyridin-4-ylcarbamoyl)-thiazol-2-ylcarbamoyl]-1H-indole-2-carboxylic acid | 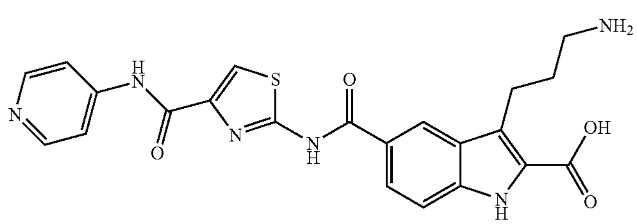 |

-continued

| Name | Structure |
|---|---|
| 3-(3-Amino-propyl)-5-{4-[2-(1H-indol-3-yl)-1-methyl-ethylcarbamoyl]-thiazol-2-ylcarbamoyl}-1H-indole-2-carboxylic acid | 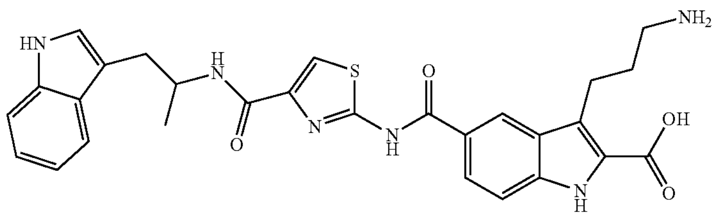 |
| 3-(3-Amino-propyl)-5-[4-(1-cyclohexyl-ethylcarbamoyl)-thiazol-2-ylcarbamoyl]-1H-indole-2-carboxylic acid | 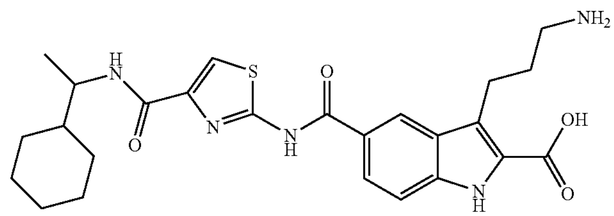 |
| 3-(3-Amino-propyl)-5-[4-(1-phenyl-ethylcarbamoyl)-thiazol-2-ylcarbamoyl]-1H-indole-2-carboxylic acid | 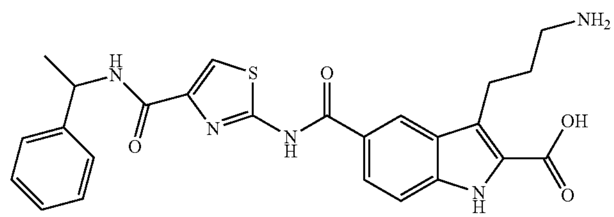 |
| 3-(3-Amino-propyl)-5-[4-(4-methyl-cyclohexylcarbamoyl)-thiazol-2-ylcarbamoyl]-1H-indole-2-carboxylic acid | 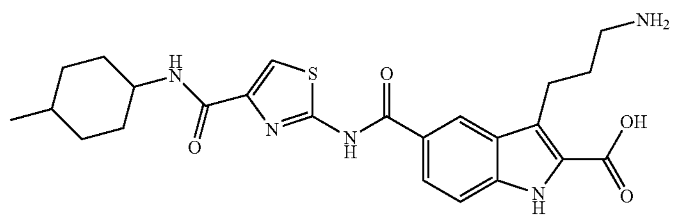 |
| 3-(3-Amino-propyl)-5-[4-(pyridin-3-ylcarbamoyl)-thiazol-2-ylcarbamoyl]-1H-indole-2-carboxylic acid | 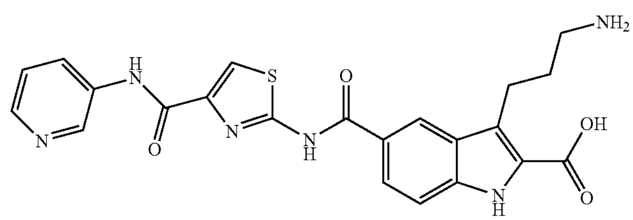 |
| 3-(3-Amino-propyl)-5-[4-(1-methyl-1H-pyrazol-3-ylcarbamoyl)-thiazol-2-ylcarbamoyl]-1H-indole-2-carboxylic acid | 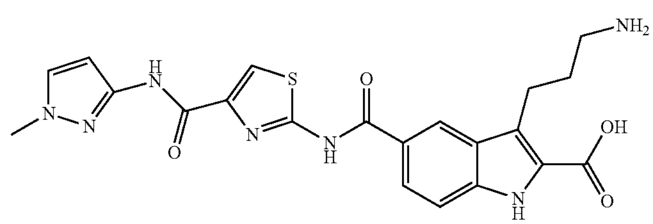 |
| 5-[4-(3-Acetylamino-phenylcarbamoyl)-thiazol-2-ylcarbamoyl]-3-(3-amino-propyl)-1H-indole-2-carboxylic acid | 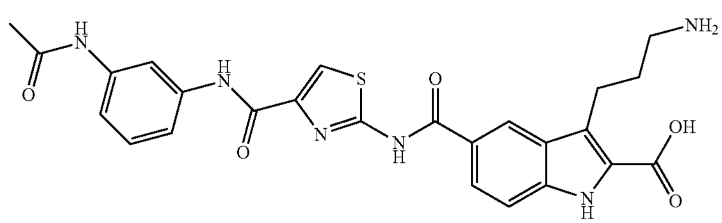 |

-continued

| Name | Structure |
|---|---|
| 3-(3-Amino-propyl)-5-[4-(1H-indol-4-ylcarbamoyl)-thiazol-2-ylcarbamoyl]-1H-indole-2-carboxylic acid | 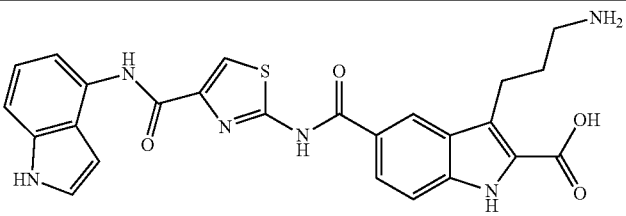 |
| 3-(3-Amino-propyl)-5-(4-ethylcarbamoyl-thiazol-2-ylcarbamoyl)-1H-indole-2-carboxylic acid | 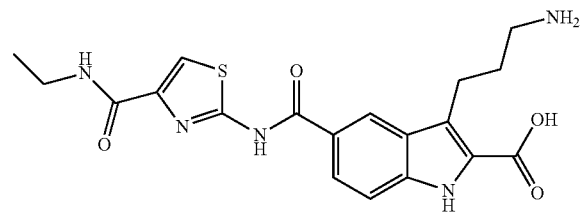 |
| 3-(3-Amino-propyl)-5-[4-(2,2-dimethyl-propylcarbamoyl)-thiazol-2-ylcarbamoyl]-1H-indole-2-carboxylic acid | 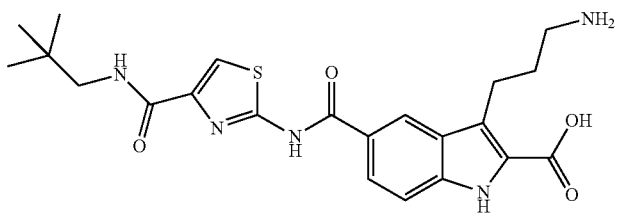 |
| 3-(3-Amino-propyl)-5-{4-[(pyridin-4-ylmethyl)-carbamoyl]-thiazol-2-ylcarbamoyl}-1H-indole-2-carboxylic acid | 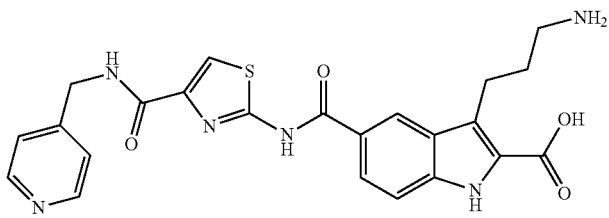 |
| 3-(3-Amino-propyl)-5-(5-ethyl-4-propylcarbamoyl-thiazol-2-ylcarbamoyl)-1H-indole-2-carboxylic acid | 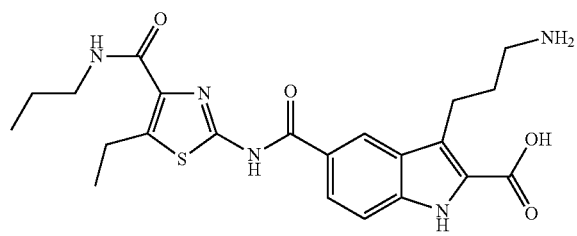 |
| 3-(3-Amino-propyl)-5-(4-cyclopropylcarbamoyl-thiazol-2-ylcarbamoyl)-1H-indole-2-carboxylic acid | 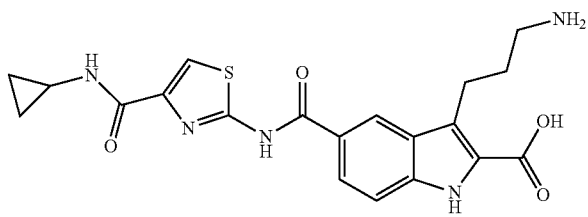 |
| 3-(3-Amino-propyl)-5-[5-ethyl-4-(2-hydroxy-ethylcarbamoyl)-thiazol-2-ylcarbamoyl]-1H-indole-2-carboxylic acid | 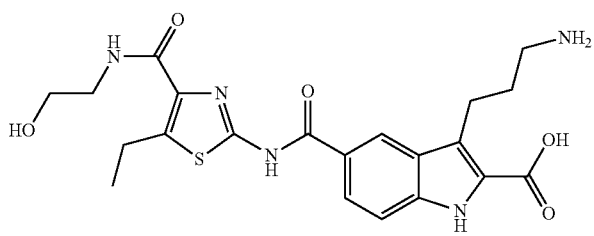 |

-continued

| Name | Structure |
|---|---|
| 3-(3-Amino-propyl)-5-[4-(2,4-difluoro-phenylcarbamoyl)-thiazol-2-ylcarbamoyl]-1H-indole-2-carboxylic acid | 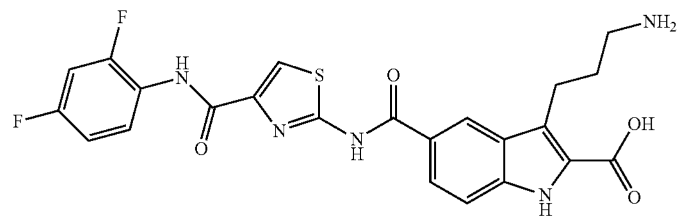 |
| 3-(3-Amino-propyl)-5-[5-ethyl-4-(3-hydroxy-propylcarbamoyl)-thiazol-2-ylcarbamoyl]-1H-indole-2-carboxylic acid | 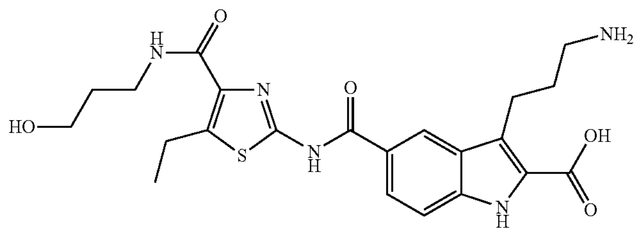 |
| 3-(3-Amino-propyl)-5-[4-(2-hydroxy-ethylcarbamoyl)-thiazol-2-ylcarbamoyl]-1H-indole-2-carboxylic acid | 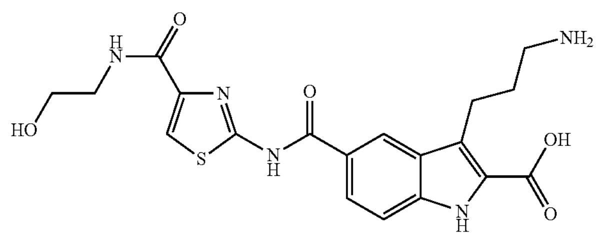 |
| 3-(3-Amino-propyl)-5-(4-butylcarbamoyl-thiazol-2-ylcarbamoyl)-1H-indole-2-carboxylic acid | 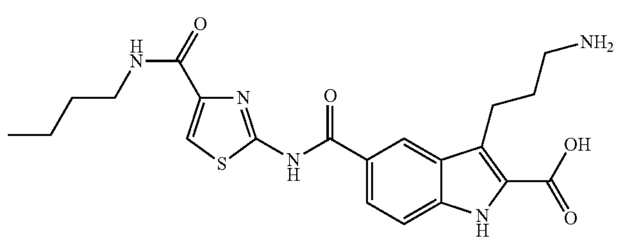 |
| 3-(3-Amino-propyl)-5-[4-(carbamoylmethyl-carbamoyl)-5-ethyl-thiazol-2-ylcarbamoyl]-1H-indole-2-carboxylic acid | 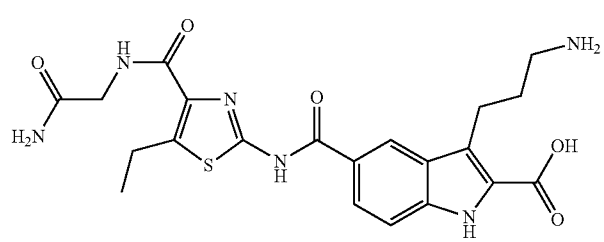 |
| 3-(3-Amino-propyl)-5-(4-propylcarbamoyl-thiazol-2-ylcarbamoyl)-1H-indole-2-carboxylic acid | 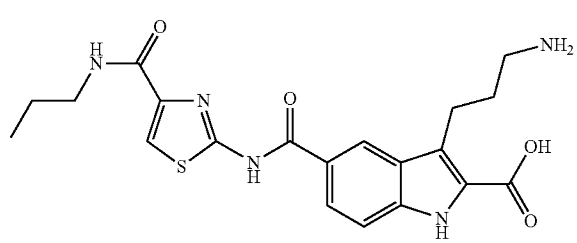 |

-continued

| Name | Structure |
|---|---|
| 3-(3-Amino-propyl)-5-[4-(1-methanesulfonyl-piperidin-4-ylcarbamoyl)-thiazol-2-ylcarbamoyl]-1H-indole-2-carboxylic acid | 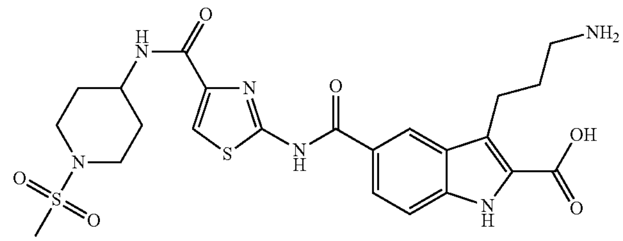 |
| 3-(3-Amino-propyl)-5-[4-(2-carbamoyl-ethylcarbamoyl)-thiazol-2-ylcarbamoyl]-1H-indole-2-carboxylic acid | 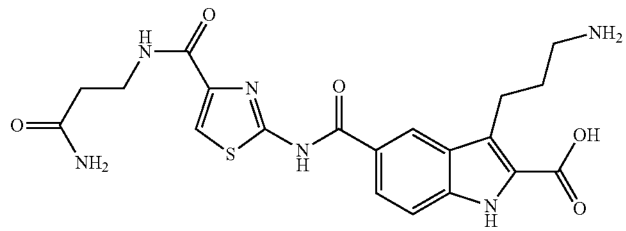 |
| 3-(3-Amino-propyl)-5-(4-cyclobutylcarbamoyl-thiazol-2-ylcarbamoyl)-1H-indole-2-carboxylic acid | 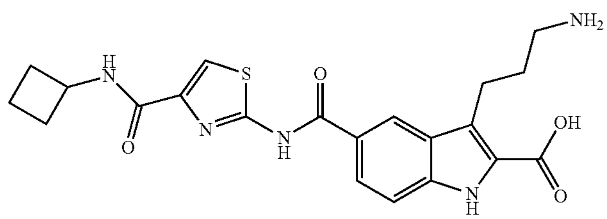 |
| 3-(3-Amino-propyl)-5-{4-[4-(4-methyl-piperazin-1-yl)-phenylcarbamoyl]-thiazol-2-ylcarbamoyl}-1H-indole-2-carboxylic acid | 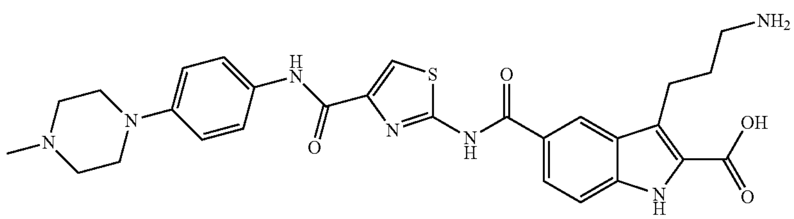 |
| 3-(3-Amino-propyl)-5-[4-(2-dimethylamino-ethylcarbamoyl)-thiazol-2-ylcarbamoyl]-1H-indole-2-carboxylic acid | 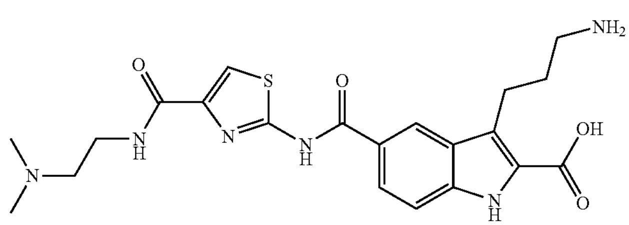 |
| 5-[4-(2-Acetylamino-ethylcarbamoyl)-thiazol-2-ylcarbamoyl]-3-(3-amino-propyl)-1H-indole-2-carboxylic acid | 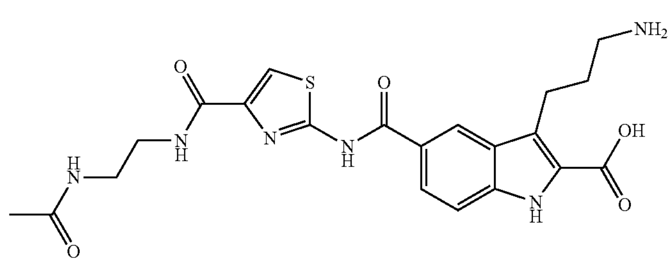 |

-continued

| Name | Structure |
|---|---|
| 3-(3-Amino-propyl)-5-[4-(5-hydroxy-1,5-dimethyl-hexylcarbamoyl)-thiazol-2-ylcarbamoyl]-1H-indole-2-carboxylic acid | 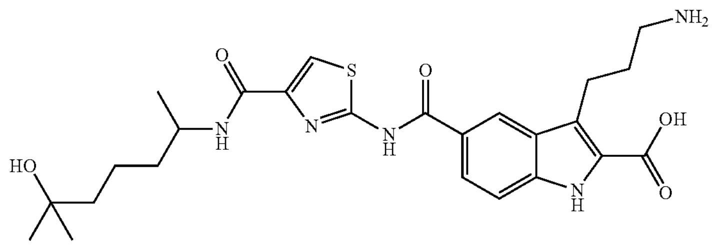 |
| 3-(3-Amino-propyl)-5-[4-(2-hydroxy-1-methyl-ethylcarbamoyl)-thiazol-2-ylcarbamoyl]-1H-indole-2-carboxylic acid | 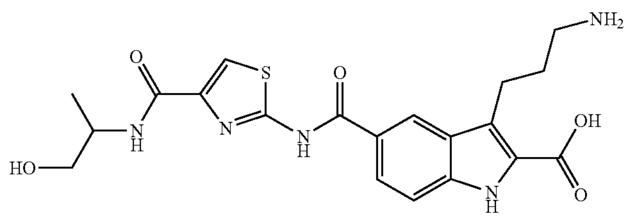 |
| 3-(3-Amino-propyl)-5-{4-[(5-methyl-pyrazin-2-ylmethyl)-carbamoyl]-thiazol-2-ylcarbamoyl}-1H-indole-2-carboxylic acid | 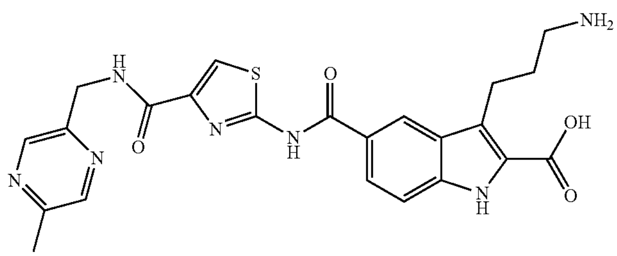 |
| 3-(3-Amino-propyl)-5-[4-(carbamoylmethyl-carbamoyl)-thiazol-2-ylcarbamoyl]-1H-indole-2-carboxylic acid | 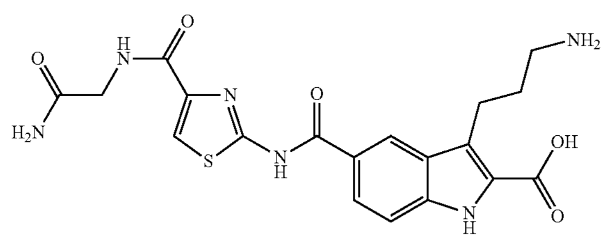 |
| 3-(3-Amino-propyl)-5-(4-cyclopentylcarbamoyl-thiazol-2-ylcarbamoyl)-1H-indole-2-carboxylic acid | 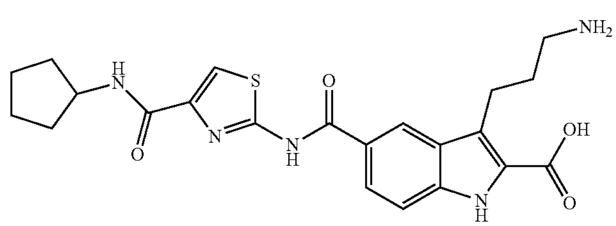 |
| 3-(3-Amino-propyl)-5-(4-cyclohexylcarbamoyl-thiazol-2-ylcarbamoyl)-1H-indole-2-carboxylic acid | 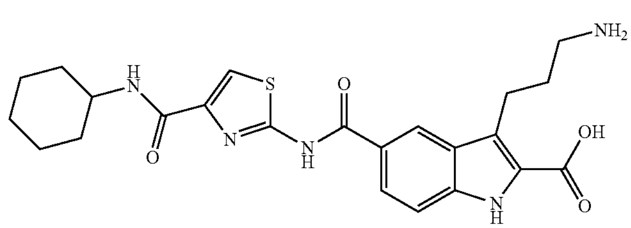 |

-continued

| Name | Structure |
|---|---|
| 3-(3-Amino-propyl)-5-(4-isopropylcarbamoyl-thiazol-2-ylcarbamoyl)-1H-indole-2-carboxylic acid | 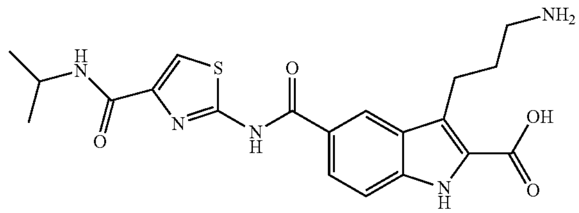 |
| 3-(3-Amino-propyl)-5-{4-[(1-methyl-pyrrolidin-2-ylmethyl)-carbamoyl]-thiazol-2-ylcarbamoyl}-1H-indole-2-carboxylic acid | 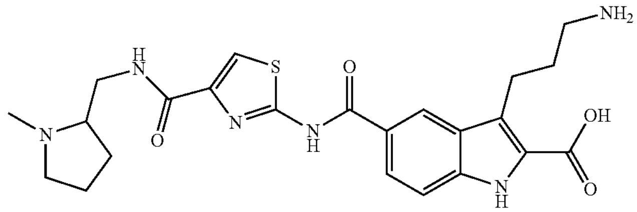 |
| 5-[4-(4-Acetylamino-phenylcarbamoyl)-thiazol-2-ylcarbamoyl]-3-(3-amino-propyl)-1H-indole-2-carboxylic acid | 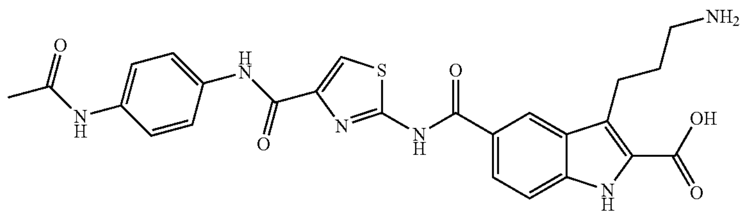 |
| 3-(3-Amino-propyl)-5-[4-(1-hydroxymethyl-propylcarbamoyl)-thiazol-2-ylcarbamoyl]-1H-indole-2-carboxylic acid | 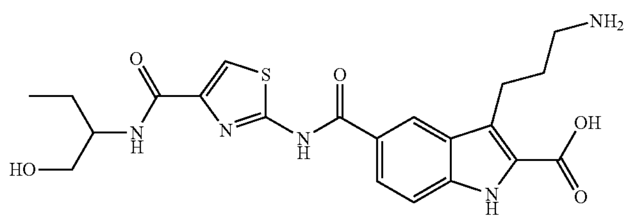 |
| 3-(3-Amino-propyl)-5-{4-[(carbamoyl-phenyl-methyl)-carbamoyl]-thiazol-2-ylcarbamoyl}-1H-indole-2-carboxylic acid | 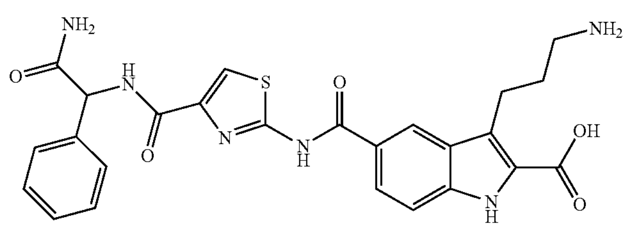 |
| 3-(3-Amino-propyl)-5-[4-(3-hydroxy-propylcarbamoyl)-thiazol-2-ylcarbamoyl]-1H-indole-2-carboxylic acid | 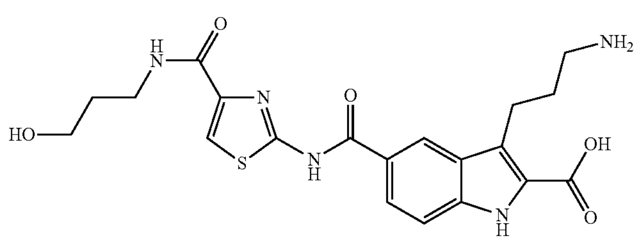 |
| 3-(3-Amino-propyl)-5-[4-(3-dimethylamino-propylcarbamoyl)-thiazol-2-ylcarbamoyl]-1H-indole-2-carboxylic acid | 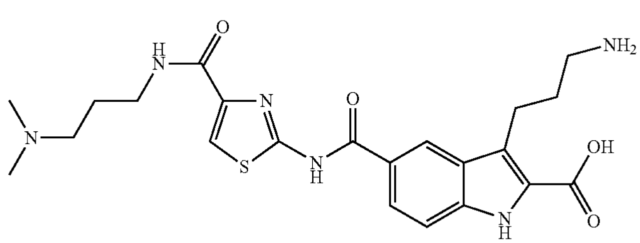 |

| Name | Structure |
|---|---|
| 5-[4-(2-Amino-ethylcarbamoyl)-thiazol-2-ylcarbamoyl]-3-(3-amino-propyl)-1H-indole-2-carboxylic acid | 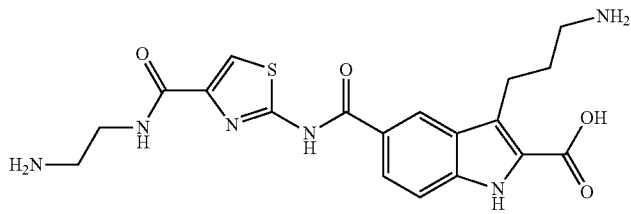 |
| 5-[4-(2-Amino-2-methyl-propylcarbamoyl)-thiazol-2-ylcarbamoyl]-3-(3-amino-propyl)-1H-indole-2-carboxylic acid | 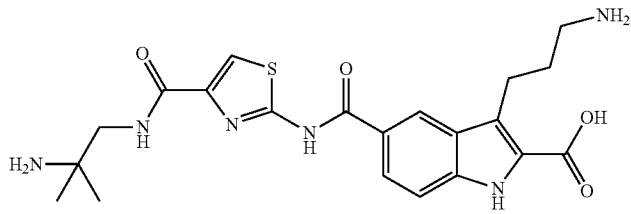 |
| 3-(3-Amino-propyl)-5-{4-[(6-trifluoromethyl-pyridin-3-ylmethyl)-carbamoyl]-thiazol-2-ylcarbamoyl}-1H-indole-2-carboxylic acid | 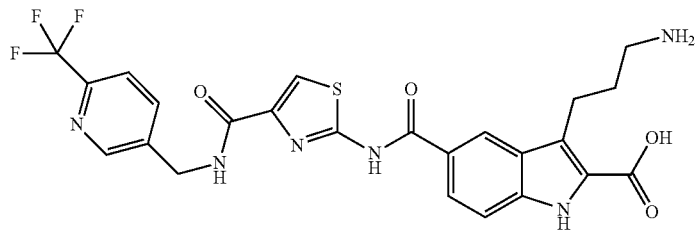 |
| 3-(3-Amino-propyl)-5-[4-(1-ethyl-propylcarbamoyl)-thiazol-2-ylcarbamoyl]-1H-indole-2-carboxylic acid | 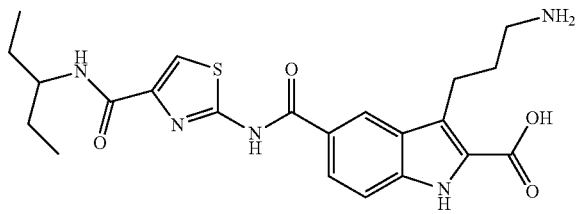 |
| 5-[4-(2-Methamino-ethylcarbamoyl)-thiazol-2-ylcarbamoyl]-3-(3-amino-propyl)-1H-indole-2-carboxylic acid | 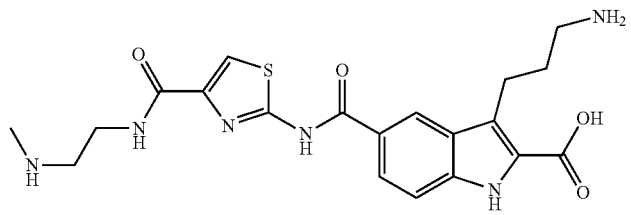 |
| 3-(3-Amino-propyl)-5-{4-[(tetrahydropyran-4-ylmethyl)-carbamoyl]-thiazol-2-ylcarbamoyl}-1H-indole-2-carboxylic acid | 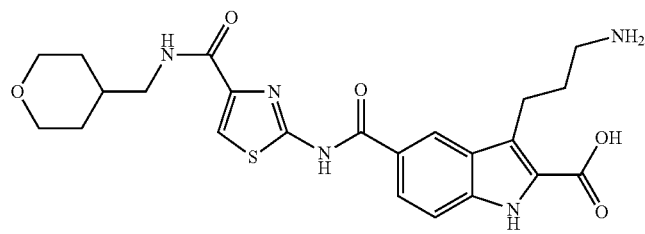 |
| 3-(3-Amino-propyl)-5-[4-(1-phenyl-2-pyrrolidin-1-yl-ethylcarbamoyl)-thiazol-2-ylcarbamoyl]-1H-indole-2-carboxylic acid | 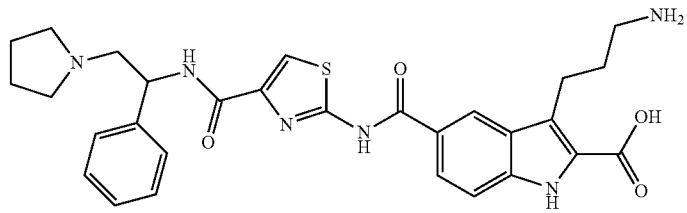 |

-continued

| Name | Structure |
|---|---|
| 3-(3-Amino-propyl)-5-(4-methylcarbamoyl-thiazol-2-ylcarbamoyl)-1H-indole-2-carboxylic acid | 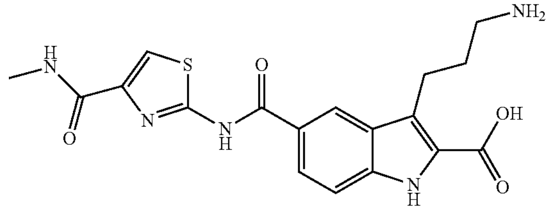 |
| 3-(3-Amino-propyl)-5-[4-(3-propylcarbamoyl)-thiazol-2-ylcarbamoyl]-1H-indole-2-carboxylic acid | 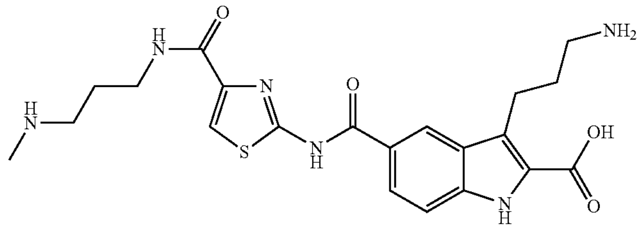 |
| 5-[4-(2-Dimethylamino-ethylcarbamoyl)-thiazol-2-ylcarbamoyl]-3-(3-amino-propyl)-1H-indole-2-carboxylic acid | 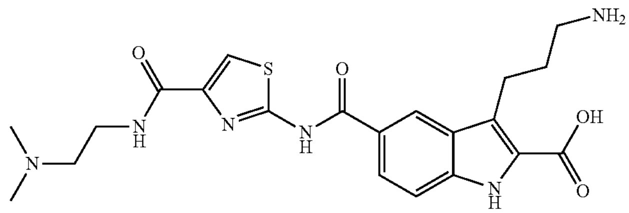 |
| 3-(3-Amino-propyl)-5-{4-[2-(4-methyl-piperazin-1-yl)-ethylcarbamoyl]-thiazol-2-ylcarbamoyl}-1H-indole-2-carboxylic acid | 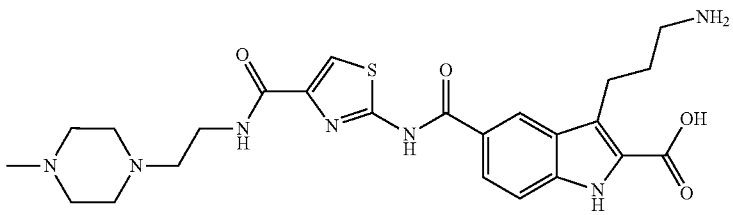 |
| 3-(3-Amino-propyl)-5-(4-tert-butylcarbamoyl-thiazol-2-ylcarbamoyl)-1H-indole-2-carboxylic acid | 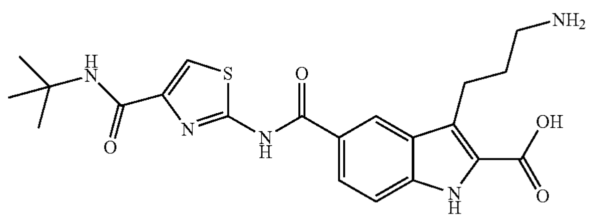 |
| 5-[4-(1-Acetyl-piperidin-4-ylcarbamoyl)-thiazol-2-ylcarbamoyl]-3-(3-amino-propyl)-1H-indole-2-carboxylic acid | 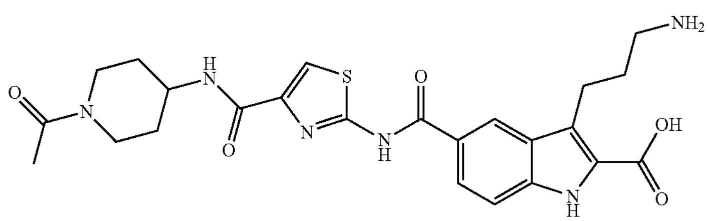 |
| 3-(3-Amino-propyl)-5-[4-(tetrahydro-pyran-4-ylcarbamoyl)-thiazol-2-ylcarbamoyl]-1H-indole-2-carboxylic acid | 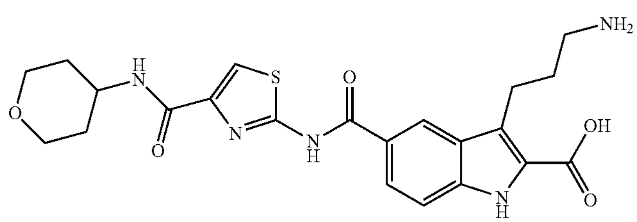 |

| Name | Structure |
|---|---|
| 3-(3-Amino-propyl)-5-[5-ethyl-4-(1-methyl-piperidin-4-ylcarbamoyl)-thiazol-2-ylcarbamoyl]-1H-indole-2-carboxylic acid | 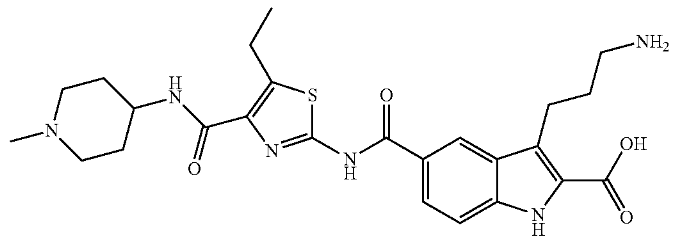 |
| 5-[4-(Piperidin-4-ylcarbamoyl)-thiazol-2-ylcarbamoyl]-3-(3-amino-propyl)-1H-indole-2-carboxylic acid | 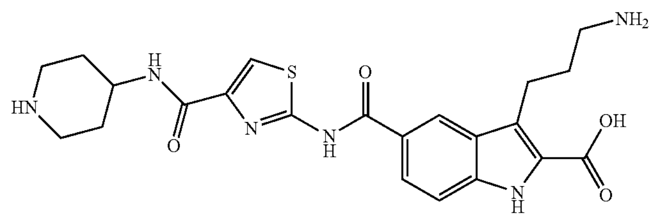 |
| 3-(3-Amino-propyl)-5-{4-[1-(4-methanesulfonyl-phenyl)-ethylcarbamoyl]-thiazol-2-ylcarbamoyl}-1H-indole-2-carboxylic acid | 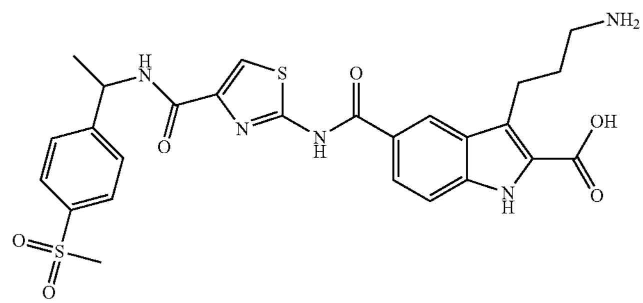 |
| 3-(3-Amino-propyl)-5-[4-(2-dimethylamino-ethylcarbamoyl)-5-ethyl-thiazol-2-ylcarbamoyl]-1H-indole-2-carboxylic acid | 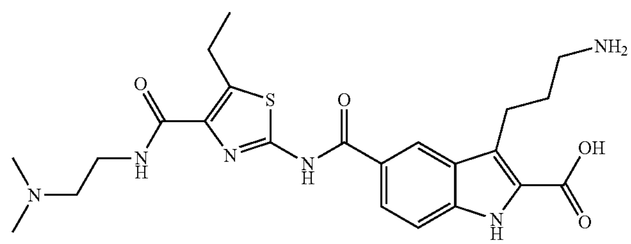 |
| 3-(3-Amino-propyl)-5-[4-(1-benzyl-piperidin-4-ylcarbamoyl)-thiazol-2-ylcarbamoyl]-1H-indole-2-carboxylic acid | 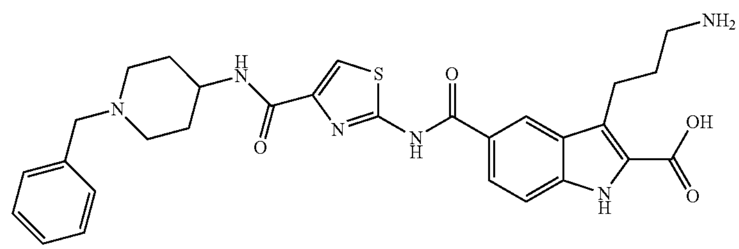 |
| 3-(3-Amino-propyl)-5-[4-(1-cyclohexyl-piperidin-4-ylcarbamoyl)-thiazol-2-ylcarbamoyl]-1H-indole-2-carboxylic acid | 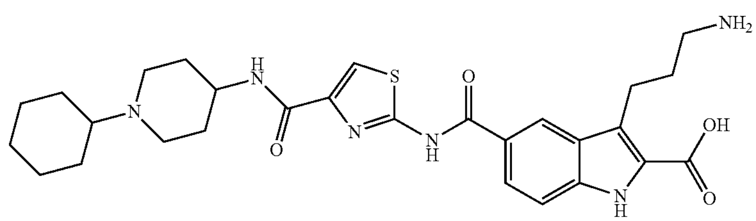 |

-continued

| Name | Structure |
|---|---|
| 3-(3-Amino-propyl)-5-[4-(2,2,6,6-tetramethyl-piperidin-4-ylcarbamoyl)-thiazol-2-ylcarbamoyl]-1H-indole-2-carboxylic acid | 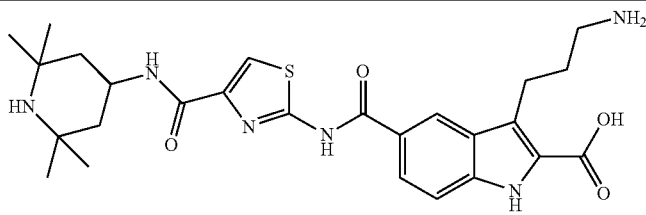 |
| 3-(3-Amino-propyl)-5-{4-[1-(2,2-dimethyl-propyl)-piperidin-4-ylcarbamoyl]-thiazol-2-ylcarbamoyl}-1H-indole-2-carboxylic acid | 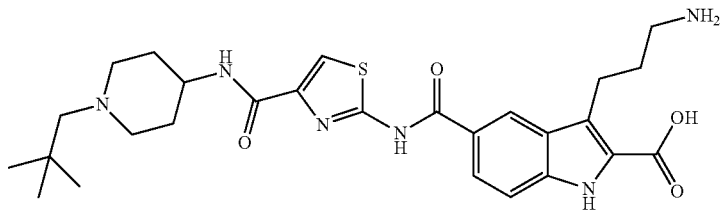 |
| 3-(3-Amino-propyl)-5-[4-(1,2,2,6,6-pentamethyl-piperidin-4-ylcarbamoyl)-thiazol-2-ylcarbamoyl]-1H-indole-2-carboxylic acid | 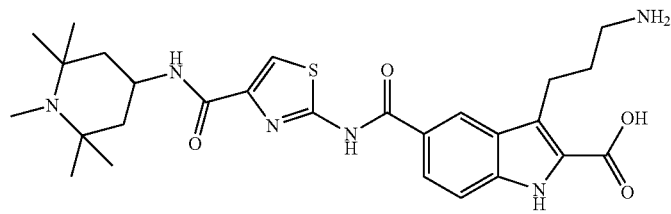 |
| 3-(3-Amino-propyl)-5-[4-(1-methyl-piperidin-4-ylcarbamoyl)-thiazol-2-ylcarbamoyl]-1H-indole-2-carboxylic acid | 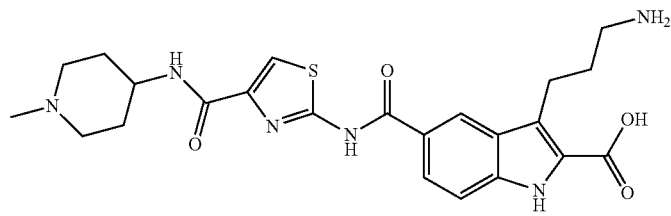 |

The following preferred compounds have an $IC_{50}$ less than 10 micromolar.

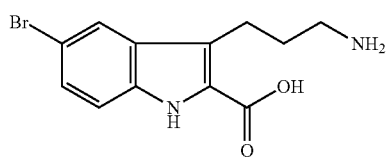

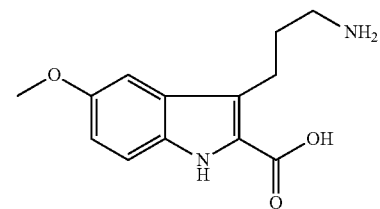

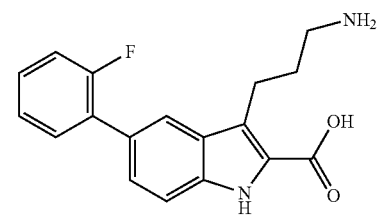

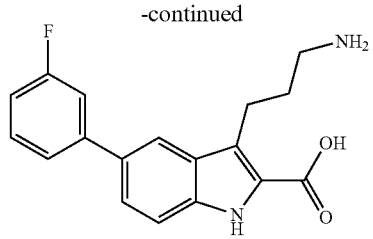

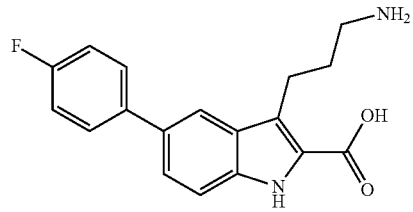

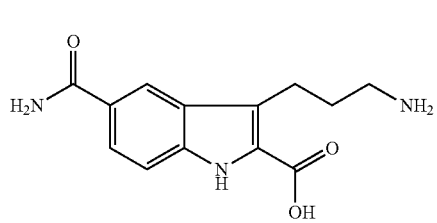

| 39 | 40 |
|---|---|
| -continued | -continued |
| 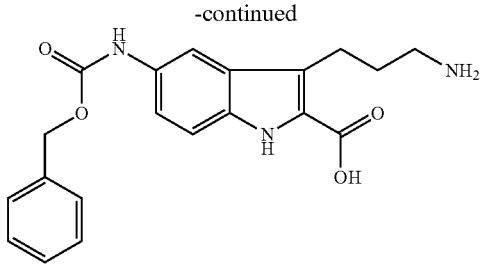 | 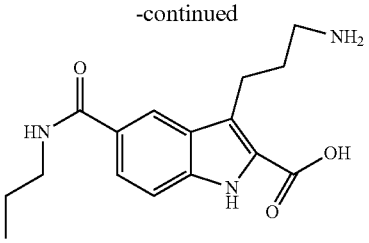 |
| 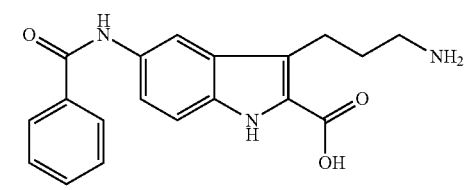 | 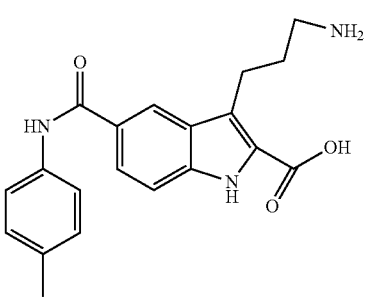 |
| 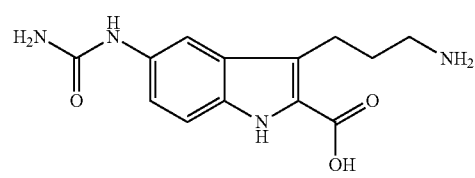 | 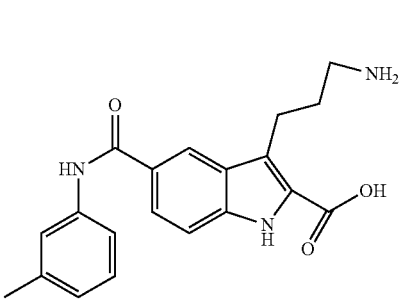 |
| 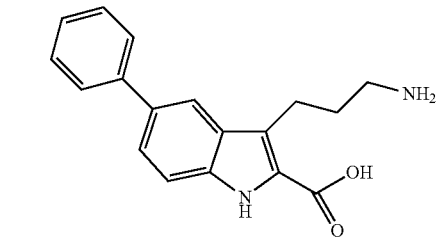 | 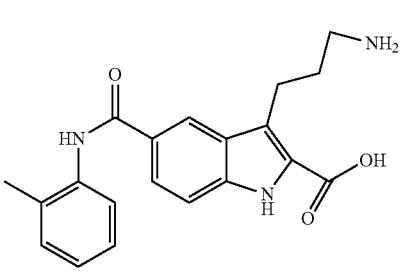 |
| 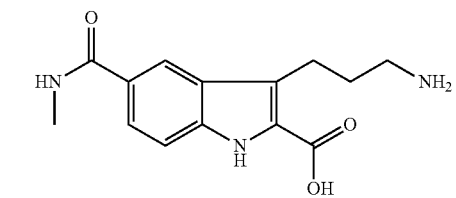 | 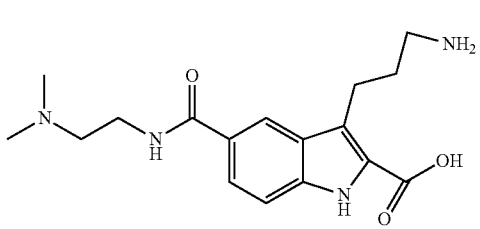 |
| 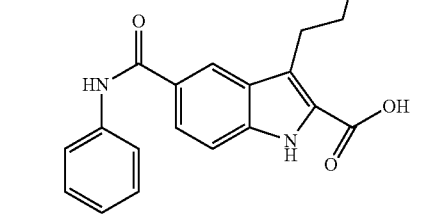 | 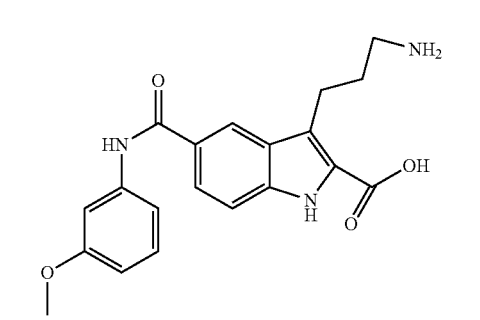 |
| 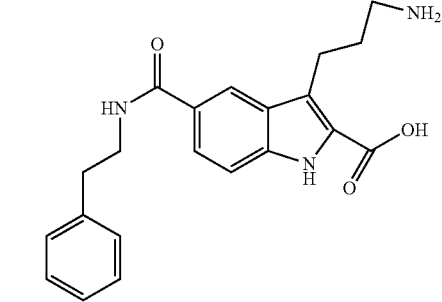 | |

-continued

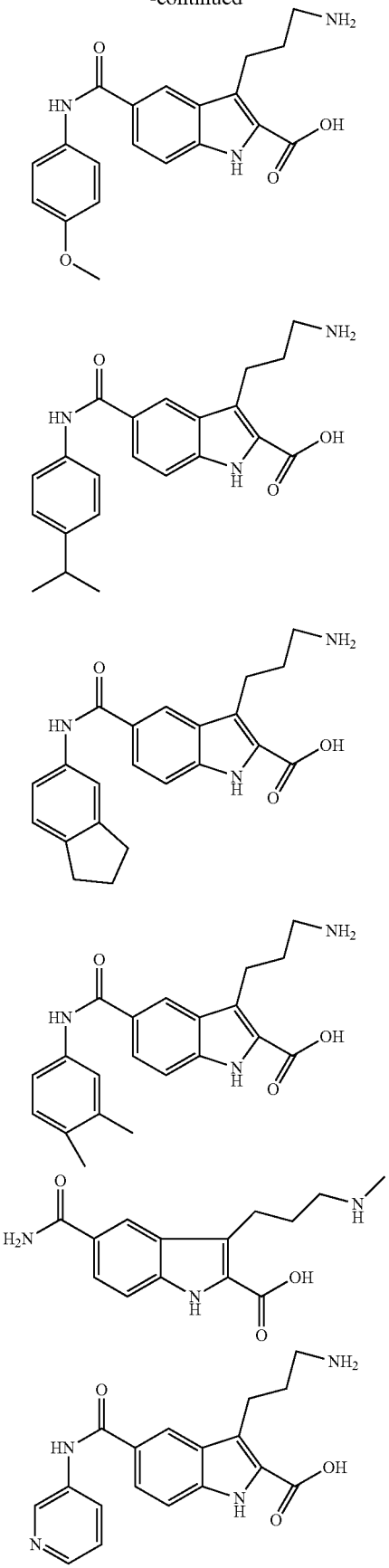

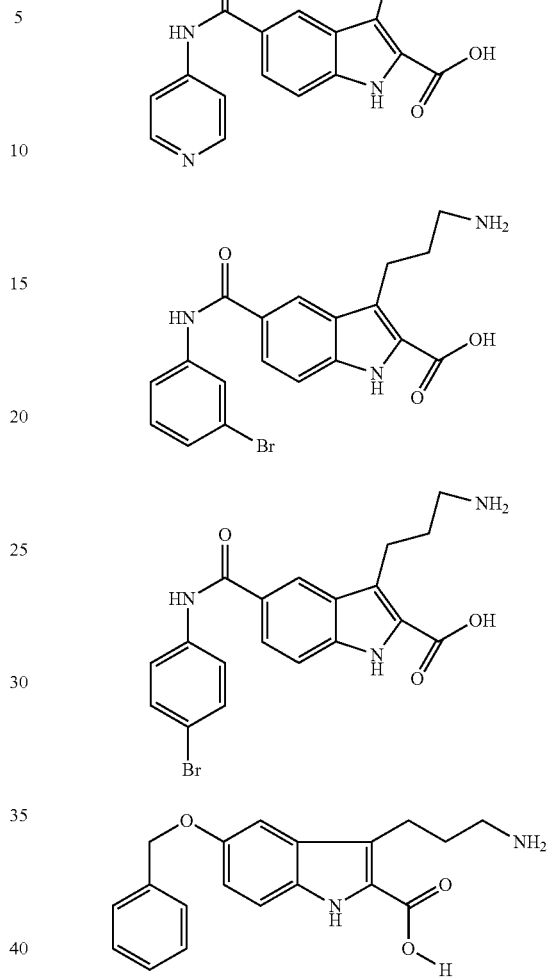

In all the compounds disclosed in this application, in the event the nomenclature is in conflict with the structure, it shall be understood that the compound is defined by the structure.

The invention includes the use of any compounds that contain one or more asymmetric carbon atoms which may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of formula (I) can exist in more than one tautomeric form. The invention includes methods using all such tautomers.

All terms as used herein in this specification, unless otherwise stated, shall be understood in their ordinary meaning as known in the art. For example, "$C_{1-6}$ alkoxy" is a $C_{1-6}$alkyl that contains an oxygen atom, such as methoxy, ethoxy, propoxy, butoxy. All alkyl, alkenyl and alkynyl groups shall be understood as being branched or unbranched where structurally possible and unless otherwise specified. Other more specific definitions are as follows:

The term "cycloalkyl" shall be understood to mean an aliphatic hydrocarbon radical containing from three to twelve carbon atoms. Cycloalkyls include hydrocarbon rings containing from three to ten carbon atoms. These cycloalkyls may be either aromatic and non-aromatic ring systems. The non-aromatic ring systems may be mono- or polyunsaturated. Preferred cycloalkyls include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used interchangeably.

The term "heterocycle" refers to a stable nonaromatic 4-8 membered (but preferably, 5 or 6 membered) monocyclic or nonaromatic 8-11 membered bicyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure. Unless otherwise stated, heterocycles include but are not limited to, for example pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, 1-oxo-λ4-thiomorpholinyl, 13-oxa-11-aza-tricyclo[7.3.1.0-2,7]trideca-2,4,6-triene, tetrahydropyranyl, 2-oxo-2H-pyranyl, tetrahydrofuranyl, 1,3-dioxolanone, 1,3-dioxanone, 1,4-dioxanyl, 8-oxa-3-aza-bicyclo[3.2.1]octanyl, 2-oxa-5-aza-bicyclo[2.2.1]heptanyl, 2-thia-5-aza-bicyclo[2.2.1]heptanyl, piperidinonyl, tetrahydropyrimidonyl, pentamethylene sulfide, pentamethylene sulfoxide, pentamethylene sulfone, tetramethylene sulfide, tetramethylene sulfoxide and tetramethylene sulfone.

The term "heteroaryl" shall be understood to mean an aromatic 5-8 membered monocyclic or 8-11 membered bicyclic ring containing 1-4 heteroatoms such as N, O and S. Unless otherwise stated, such heteroaryls include thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl and imidazo[4,5-b]pyridinyl.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein shall be understood to mean aromatic cycloalkyl or heteroaryl as defined herein. Each aryl or heteroaryl unless otherwise specified includes its partially or fully hydrogenated derivative. For example, quinolinyl may include decahydroquinolinyl and tetrahydroquinolinyl, naphthyl may include it's hydrogenated derivatives such as tetrahydranaphthyl. Other partially or fully hydrogenated derivatives of the aryl and heteroaryl compounds described herein will be apparent to one of ordinary skill in the art.

Terms which are analogs of the above cyclic moieties such as aryloxy or heteroaryl amine shall be understood to mean an aryl, heteroaryl or heterocycle (as defined above) attached to its respective group.

As used herein, "nitrogen" and "sulfur" include any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl.

The term "halogen" as used in the present specification shall be understood to mean bromine, chlorine, fluorine or iodine. The definitions "partially or fully halogenated" "substituted by one or more halogen atoms" includes for example, mono, di or tri halo derivatives on one or more carbon atoms. For alkyl, a nonlimiting example would be —$CH_2CHF_2$, —$CF_3$ etc.

The term "ureido", as used in the present specification, is a substituent having the general formula of $R^wR^zNC(O)NR^xR^y$ The term "carbamoyl", as used in the present specification, is a substituent having the general formula $C(O)NR^xR^y$ or $NHC(O)R^x$.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—(C1-C4 alkyl)4+ salts.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

General Synthetic Methods

The compounds of the invention may be prepared by the general methods and examples presented below, and methods known to those of ordinary skill in the art. Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. In the schemes below, unless otherwise specified, X and $R^1$-$R^4$ in the formulas shown below shall have the meanings defined for these groups in the definition of the formula I of the invention, described hereinabove. Intermediates used in the syntheses below are either commercially available or easily prepared by methods known to those skilled in the art. Reaction progress may be monitored by conventional methods such as thin layer chromatography (TLC). Intermediates and products may be purified by methods known in the art, including column chromatography, HPLC or recrystallization.

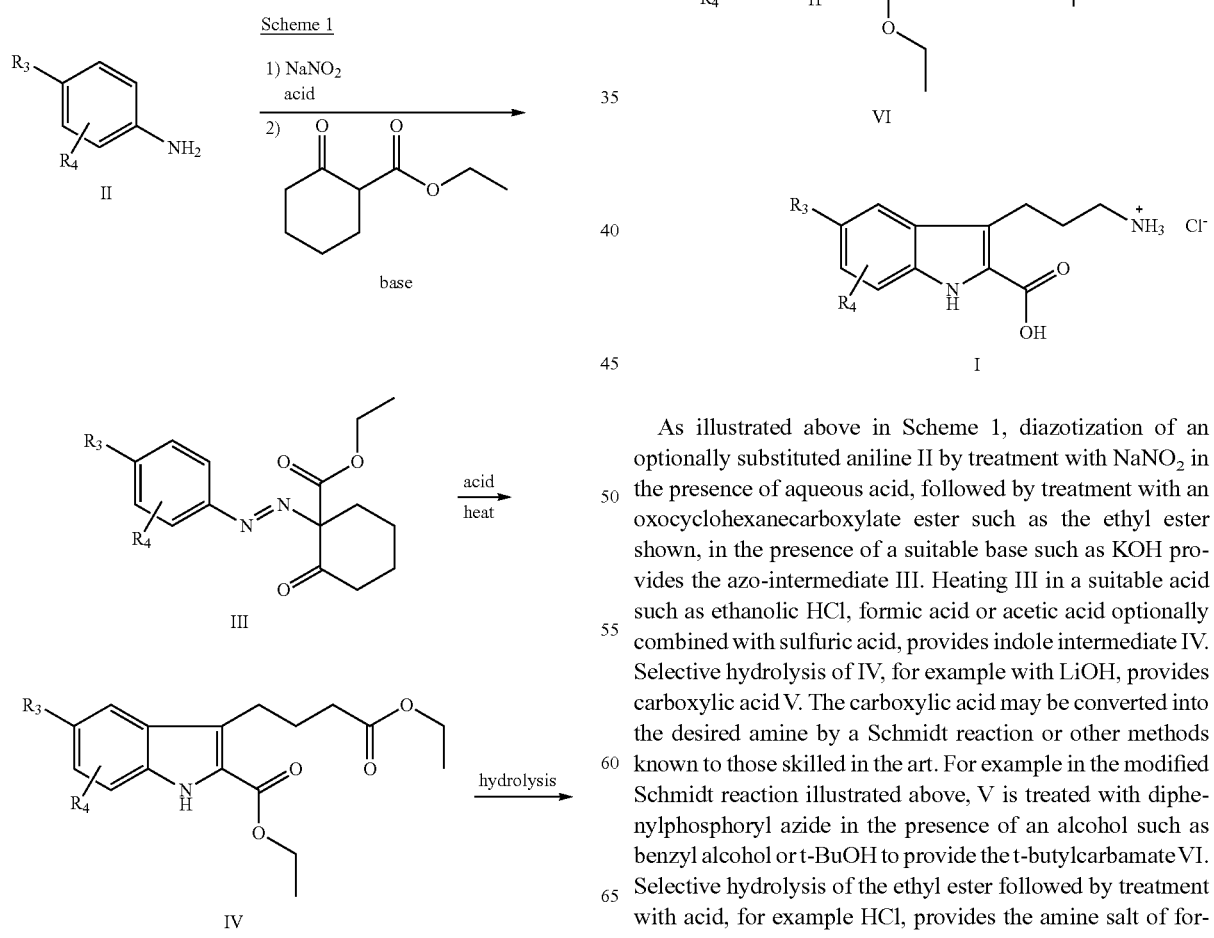

As illustrated above in Scheme 1, diazotization of an optionally substituted aniline II by treatment with $NaNO_2$ in the presence of aqueous acid, followed by treatment with an oxocyclohexanecarboxylate ester such as the ethyl ester shown, in the presence of a suitable base such as KOH provides the azo-intermediate III. Heating III in a suitable acid such as ethanolic HCl, formic acid or acetic acid optionally combined with sulfuric acid, provides indole intermediate IV. Selective hydrolysis of IV, for example with LiOH, provides carboxylic acid V. The carboxylic acid may be converted into the desired amine by a Schmidt reaction or other methods known to those skilled in the art. For example in the modified Schmidt reaction illustrated above, V is treated with diphenylphosphoryl azide in the presence of an alcohol such as benzyl alcohol or t-BuOH to provide the t-butylcarbamate VI. Selective hydrolysis of the ethyl ester followed by treatment with acid, for example HCl, provides the amine salt of formula I. Further modification of $R_3$, $R_4$ or the amine functionality by methods known in the art and methods illustrated in the Synthetic Examples section can provide additional desired compounds of formula I.

An alternate approach that may be used to prepare compounds of formula I is illustrated in Scheme 2.

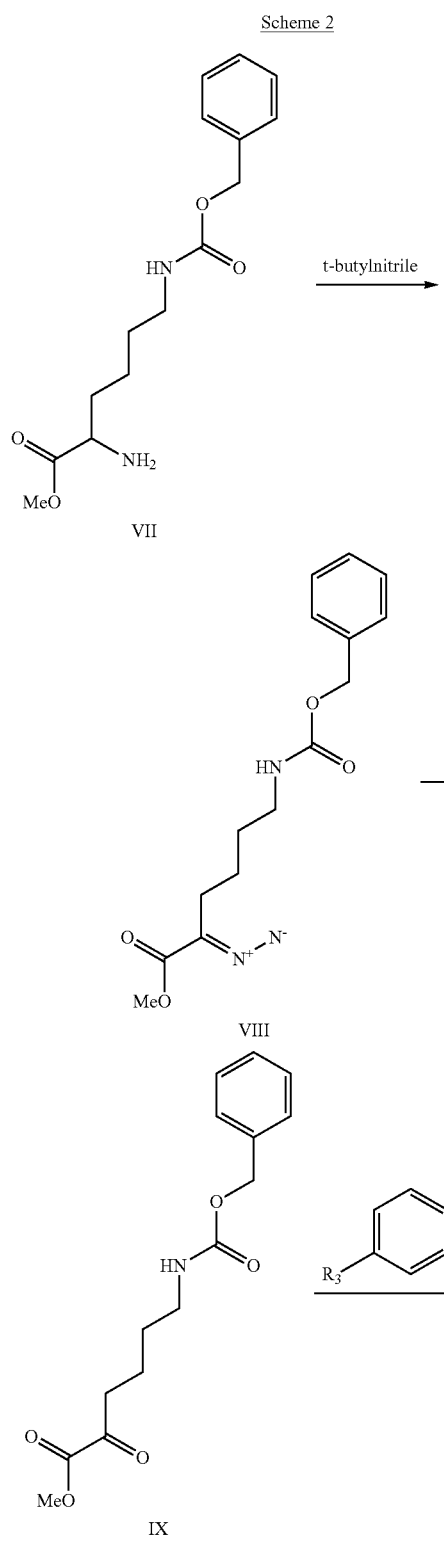

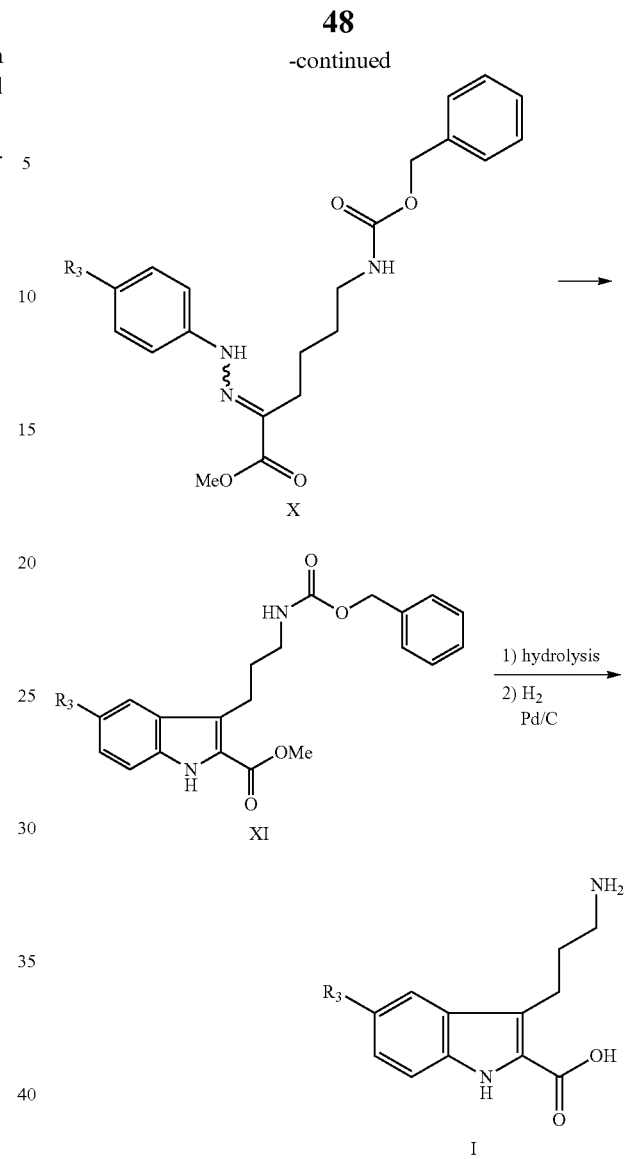

As illustrated above, ε-benzyloxycarbonyl-L-lysine methyl ester is treated with t-butyl nitrite in the presence of a suitable acid such as HOAc to provide VIII which may be reacted in situ with m-chloroperoxybenzoic acid to provide ketoester IX. This may be reacted with an optionally substituted phenylhydrazine in a suitable solvent such as HOAc to provide intermediate hydrazone X. Treatment of X in a suitable acid, for example $H_2SO_4$ in HOAc while heating provides XI. Selective hydrolysis of XI as described for VI in Scheme I, followed by treatment of the benzyl carbamate with hydrogen in the presence of palladium on carbon provides the desired compound of formula I.

If $R_3$ is $CO_2H$, intermediate XI is convenient for preparing compounds of formula I having $R_3$ being an amide —CONRR'. For example, as illustrated in Scheme 3, treatment of XIa with the desired amine RR'NH, in the presence of a suitable coupling reagent such as 1-(3-dimethylaminopropyl)-3-ethylcarbodiimide and 1-hydroxybenzotriazole hydrate provides the desired amide at $R_3$ (XII). The resulting intermediate XII may be treated as described above for XI to provide the desired compound of formula I with an amide at $R_3$.

Scheme 3
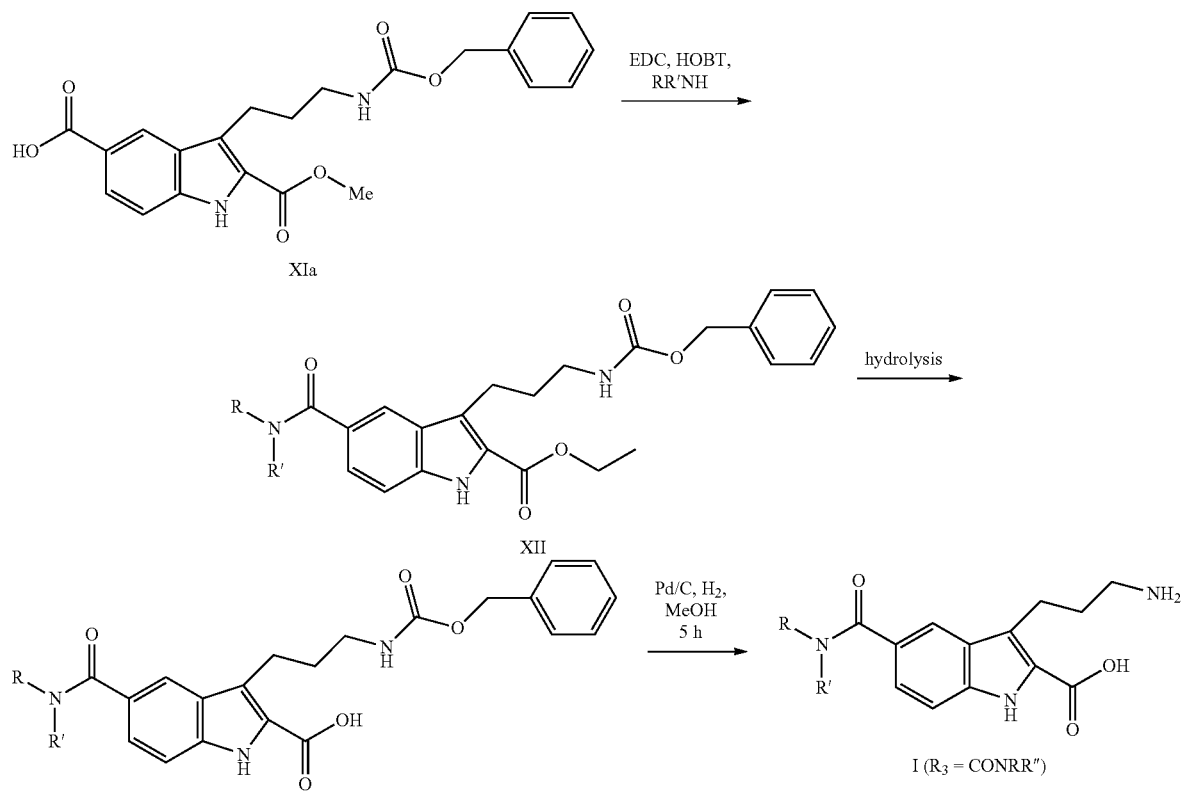
The above general methods and additional specific examples are illustrated in the section below.
SYNTHETIC EXAMPLES
Example 1
Preparation of 5-benzyloxy-3-(3-aminopropyl]-1H-indole-2-carboxylic acid hydrochloride
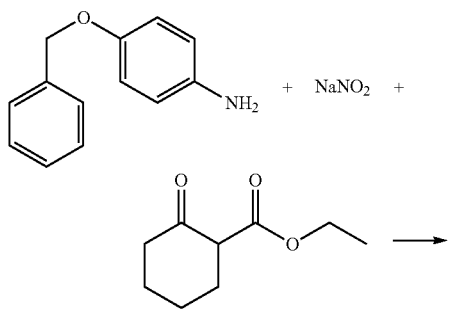
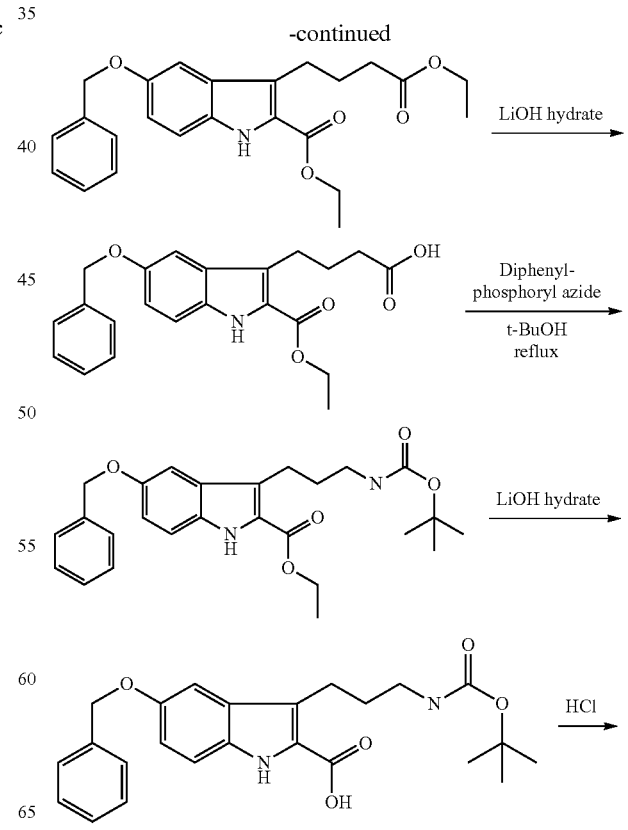

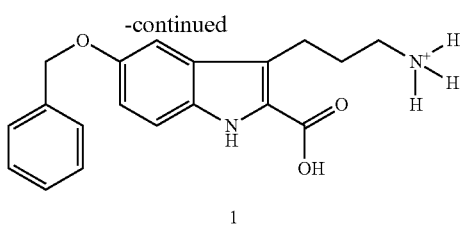

4-Benzyloxyaniline hydrochloride (24.5 g, 99 mmol, 1.0 equiv) was crushed into a free-flowing powder and suspended in 100 g of ice-water in a 500 mL round-bottomed flask with a stir bar. Concentrated HCl (16.8 mL) was added and the flask was immersed in an ice-water bath and stirring was begun. A solution of sodium nitrite (6.8 g, 99 mmol, 1.0 equiv) in 25 mL of deionized water was slowly added over a period of 15 min to the aniline mixture. At each 5 min interval 5 g of ice was added to the reaction mix to maintain the internal temperature close to 0° C. After the addition of the nitrite, most of the solid had dissolved and the tan solution was stirred at 0° C. for 10 min.

A second round-bottomed-flask (1000 mL in size with a stir bar) was charged with potassium hydroxide (17.5 g, 312 mmol, 3.15 equiv) and 100 mL of water. After the base dissolved (about 1 min), 100 g of ice was added followed by addition of ethyl 2-oxocyclohexanecarboxylate (16.4 g, 96 mmol, 0.97 equiv) which quickly dissolved in the basic solution. The beta-keto ester anion solution was vigorously stirred while the diazonium solution was slowly poured into the cold basic solution. Immediately, a bright yellow-orange precipitate formed which hindered the stir bar. After the addition, the flask was swirled for 10 min on the rotovap and then 26 mL of concentrated HCl was added. The precipitate immediately began to coalesce into a dark red-orange gum. The water was carefully decanted and the gum was washed 3×250 mL of water followed by decantation of the supernatant. The red-orange gum was dried at 30° C. under high-vacuum. The crude 1-(4-benzyloxy-phenylazo)-2-oxo-cyclohexanecarboxylic acid ethyl ester (35 g, 93%) was used in the next step without further manipulation.

Absolute ethanol (190 g) was placed in a 500 mL round-bottom-flask with a stir bar and cooled under Ar to 0° C. Acetyl chloride (23 g, 292 mmol, 1.0 equiv) was added dropwise over a 10 min period and the resulting solution was warmed to room temperature over the next hour to give an approximately 5% solution of HCl in 90/10 ethanol/ethyl acetate. The resulting solution was added to the 1-(4-benzyloxy-phenylazo)-2-oxo-cyclohexanecarboxylic acid ethyl ester prepared above (35 g, 92 mmol, 0.3 equiv) in a 1000 mL round-bottomed-flask and the resulting solution was gently refluxed on a hot water bath for 45 min. The reaction mixture was cooled and a white solid was present (ammonium chloride). The mixture was poured into 750 mL of water and the dark brown precipitate was collected by filtration and washed with 2×200 mL of water. The solid was stirred with 200 mL of methanol and filtered, and the light tan solid was washed 2×100 mL of methanol to provide 17 g (45%) of 5-benzyloxy-3-(3-ethoxycarbonyl-propyl)-1H-indole-2-carboxylic acid ethyl ester. This material was used without further manipulation.

5-Benzyloxy-3-(3-ethoxycarbonyl-propyl)-1H-indole-2-carboxylic acid ethyl ester (8 g, 19.5 mmol, 1.0 equiv) was suspended in 30 mL of ethanol. 30 mL of THF was added and the mix was stirred for 5 min and then heated gently at 40° C. on a water bath until all of the diester had dissolved. A solution of lithium hydroxide hydrate (1.23 g, 42 mmol, 1.5 equiv) in 30 mL of water was prepared and poured into the diester solution. A fine white precipitate formed that redissolved on the addition of another 10 mL of water. The resulting solution was stirred overnight. In the morning a test of the pH by pH paper revealed a pH of approximately 8 which indicated consumption of the hydroxide. TLC (100% ethyl acetate) showed a very faint spot for the diester (rf=0.95) and two overlapping spots near the baseline. The pH was adjusted to <1 with concentrated HCl and the products were extracted with 2×100 mL of ethyl acetate. The organics were combined and dried over sodium sulfate. The liquid was decanted and concentrated to a paste that was triturated with a mixture of 30 mL of methylene chloride in 120 mL of hexanes. The orange-beige precipitate was collected by filtration and washed with 100 mL of hexanes. $^1$H NMR revealed a 2.5 to 1 mixture of the desired 5-benzyloxy-3-(3-carboxy-propyl)-1H-indole-2-carboxylic acid ethyl ester to diacid (6.7 g).

The crude mixture from above (6.7 g) was dissolved in 50 mL of boiling ethyl acetate and the mixture was then cooled to room temperature (no solids reform). The above solution was purified by flash chromatography on silica gel ($SiO_2$ column size 5 cm×30 cm) using 100% ethyl acetate as the mobile phase. 5-Benzyloxy-3-(3-carboxy-propyl)-1H-indole-2-carboxylic acid ethyl ester was isolated as beige solid (3.5 g, 47%) that was used without further manipulation.

The purified ethyl ester from above (1.0 g, 2.62 mmol, 1.0 equiv) was suspended in 20 mL of t-butanol (anhydrous). Triethylamine (0.283 g, 2.8 mmol, 1.1 equiv) and diphenylphosphoryl azide (0.771 g, 2.8 mmol, 1.1 equiv) were added and the resulting mixture was refluxed under Ar for 5 h at which time MS showed a strong peak for the product and no peak for the starting material. The reaction solution was concentrated and the residue was re-dissolved in ethyl acetate. The solution was washed with 2×20 mL saturated aqueous sodium bicarbonate solution and the organic layer was dried over $Na_2SO_4$, decanted and concentrated. The product was purified by preparative reverse-phase HPLC on a semi-prep column using acetonitrile and water as the mobile phase. 5-Benzyloxy-3-[3-(t-butoxycarbonylamino)-propyl]-1H-indole-2-carboxylic acid ethyl ester was isolated as beige gum (0.2 g, 17%).

The above 5-benzyloxy-3-[3-(t-butoxycarbonylamino)-propyl]-1H-indole-2-carboxylic acid ethyl ester (0.2 g, 0.44 mmol, 1.0 equiv) was dissolved in 5 mL of ethanol. A solution of lithium hydroxide hydrate (0.2 g) in 5 mL of water was added and the resulting solution was stirred for 16 h at ambient temperature. The pH was adjusted to <1 with concentrated HCl and the product was quickly extracted with 2×15 mL of ethyl acetate. The organic layers were combined, dried over $Na_2SO_4$, decanted and concentrated to provide 5-benzyloxy-3-[3-(t-butoxycarbonylamino)-propyl]-1H-indole-2-carboxylic acid (186 mg) as a beige glass.

The above carboxylic acid (186 mg) was dissolved in 5 mL of 4 N HCl in dioxane. The resulting solution was stirred at ambient temperature for 1 h at which time MS analysis indicated consumption of the starting material and formation of the desired product. The reaction mixture was concentrated on a rotovap and the residue was triturated with diethyl ether. The title compound was collected as a fluffy white solid (121 mg) following filtration and drying in a stream of air; MS analysis electrospray, 325 (M+H).

Example 2

Preparation of 5-bromo-3-(3-aminopropyl]-1H-indole-2-carboxylic acid hydrochloride

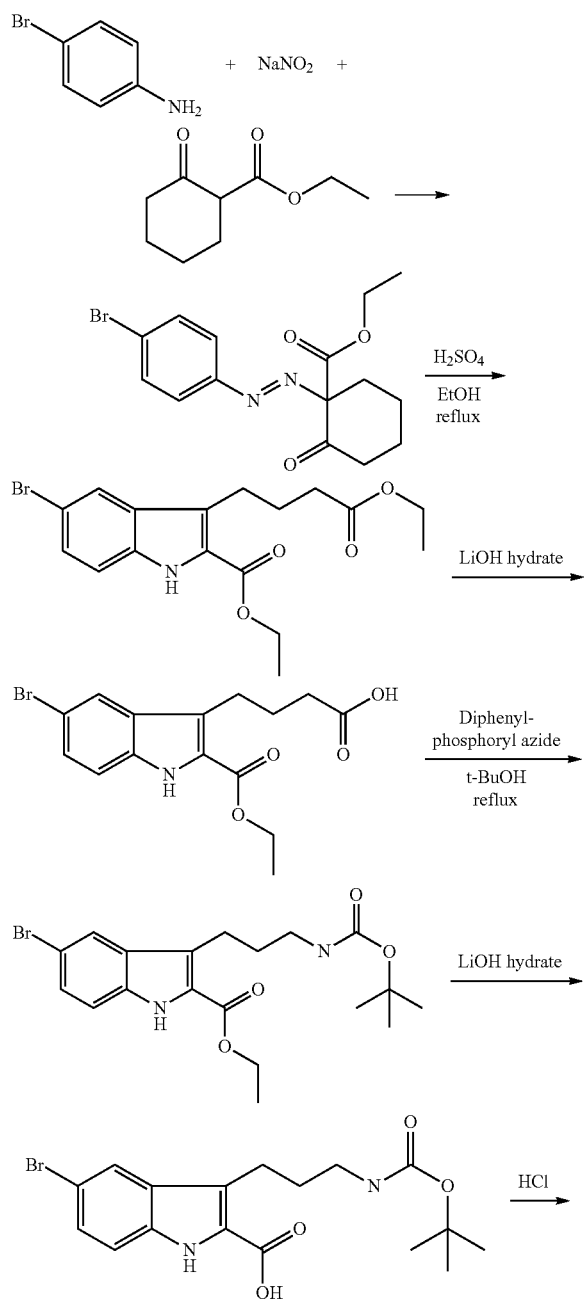

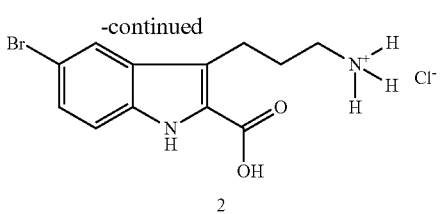

4-Bromoaniline (15.7 g, 91.2 mmol, 1.0 equiv) was suspended in 100 g of ice-water in a 500 mL round-bottomed flask with a stir bar. Concentrated HCl (25 mL) was added and the flask was immersed in an ice-water bath. To the stirred solution, a solution of sodium nitrite (6.5 g, 94.2 mmol, 1.03 equiv) in 25 mL of deionized water was slowly added over a period of 15 min. At each 5 min interval 5 g of ice was added to the reaction mix to maintain the internal temperature close to 0° C. After the addition of the nitrite, most of the solid had dissolved and the tan solution was stirred at 0° C. for 10 min.

A second round-bottomed-flask (1000 mL in size with a stir bar) was charged with potassium hydroxide (16.1 g, 287 mmol, 3.15 equiv) and 100 mL of water. After the base dissolved (about 1 min), 100 g of ice was added followed by ethyl 2-oxocyclohexanecarboxylate (15 g, 88.1 mmol, 0.97 equiv) which quickly dissolved in the basic solution. The beta-keto ester anion solution was vigorously stirred while the diazonium solution was slowly poured into the cold basic solution. Immediately, a bright yellow-orange precipitate formed which hindered the stir bar. After the addition, the flask was swirled for 10 min on the rotovap and then 26 mL of concentrated HCl was added. The solid immediately began to coalesce into a dark red-orange gum. The water was carefully decanted and the gum was washed 3×250 mL of water. The material was dissolved in 200 mL of CH$_2$Cl$_2$ and washed with 1×100 mL of water and the organic was dried over Na$_2$SO$_4$. The liquid was decanted and concentrated to provide 1-(4-bromo-phenylazo)-2-oxo-cyclohexanecarboxylic acid ethyl ester as a dark red gum (29 g, 90%). This material was used without further purification.

1-(4-Bromo-phenylazo)-2-oxo-cyclohexanecarboxylic acid ethyl ester (29 g, 82.1 mmol, 1.0 equiv), was dissolved in a mixture of 250 mL ethanol and 25 mL of sulfuric acid. The dark red mixture was refluxed for a total of 24 hours at which time MS analysis indicated that the product had formed and the starting material had been consumed. The solution was cooled and 500 mL of water was added with vigorous stirring. A dark waxy solid formed that was broken up with a spatula and the mixture was vigorously stirred for 2 h at which time a fine crystalline dark orange solid had formed that was collected by filtration and washed with 3×100 mL of water and dried. The solid was re-dissolved in 70 mL of CH$_2$Cl$_2$ and hexanes (300 mL) were added while stirring. When no solid precipitated, the flask was placed on a rotary evaporator and the solution was concentrated until a tan solid began to precipitate at which time the flask was removed from the rotovap and another 200 mL of hexanes was added with stirring and the resulting solid was collected by filtration, washed with 3×100 mL hexanes and dried to provide 5-bromo-3-(3-ethoxycarbonyl-propyl)-1H-indole-2-carboxylic acid ethyl ester (15 g, 48%). This material was used without further manipulation.

The above diethyl ester (7.12 g, 18.8 mmol, 1.0 equiv) was dissolved in a mixture of 25 mL of THF and 25 ml, of ethanol. A solution of potassium hydroxide (1.12 g, 20 mmol, 1.1 equiv) in 25 mL of water was added and the mixture was stirred for 16 h at room temperature. The reaction was not complete by TLC (EtOAc, Rf=1.00 for SM and Rf=0.80 (streaks) for product). The mixture was acidified to pH ~2 using 10% HCl and the solution was extracted with 3×75 mL of ethyl acetate. The pooled organic phases were dried (Na$_2$SO$_4$), filtered and evaporated. The residue was dissolved in 20 mL EtOAc and purified by flash chromatography on silica using 10% EtOAc in hexanes graded to 50% EtOAc in hexanes to provide recovered starting material and the desired mono-ester, 5-bromo-3-(3-carboxy-propyl)-1H-indole-2-carboxylic acid ethyl ester (2.91 g, 44%). This material was used without further manipulation.

To the above ester (0.86 g, 2.43 mmol, 1.0 equiv) in t-butanol (15 mL) was added triethylamine (1.1 mL) and diphenylphosphoryl azide (1.92 mL, 9 mmol, 3.7 equiv). The reaction mixture was stirred and heated at reflux under N$_2$ for 14 h. The reaction was cooled to ambient temperature and concentrated on an evaporator. The crude residue was then extracted with ethyl acetate, washed with 1N aqueous HCl and then with saturated aqueous NaHCO$_3$. The organic fraction was dried over anhydrous sodium sulfate, filtered, and evaporated. The crude product was purified by flash column chromatography (silica gel/ethyl acetate) to provide 5-bromo-3-[3-(t-butoxycarbonylamino)-propyl]-1H-indole-2-carboxylic acid ethyl ester (0.070 g, 7%). This material was used without further purification.

5-Bromo-3-[3-(t-butoxycarbonylamino)-propyl]-1H-indole-2-carboxylic acid ethyl ester (65 mg, 0.15 mmol, 1.0 equiv) was dissolved in 10 mL of 1:1 methanol/THF. To this was added a solution of lithium hydroxide hydrate (200 mg, 4.8 mmol, 31 equiv) in 5 mL water. The reaction was heated at 50° C. for 15 min and then stirred at ambient temperature overnight. The reaction was cooled to 0° C. and acidified to pH~2 with concentrated HCl. The product was extracted with ethyl acetate (2×25 mL). The solution was dried over anhydrous sodium sulfate, filtered, and evaporated to give 55 mg of 5-bromo-3-[3-(t-butoxycarbonylamino)-propyl]-1H-indole-2-carboxylic acid (55 mg, 91%). This material was used without further manipulation.

To 5-bromo-3-[3-(t-butoxycarbonylamino)-propyl]-1H-indole-2-carboxylic acid (55 mg, 0.14 mmol, 1.0 equiv) in methylene chloride (5 mL) at 0° C. was added 0.2 mL of 4M HCl in dioxane. The reaction was stirred at ambient temperature for 1 h. Then 10 mL of diethyl ether was added to the reaction and the reaction concentrated. To this residue was added 10 mL diethyl ether and the solid was filtered off and washed with diethyl ether several times and air dried for 15 min to provide the title compound (32 mg); MS, electrospray, 298 (M+H).

Example 3

Preparation of 3-(3-amino-propyl)-5-(2-fluoro-phenyl)-1H-indole-2-carboxylic acid hydrochloride

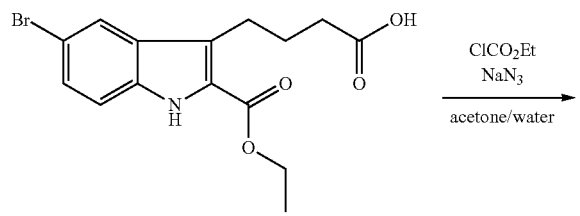

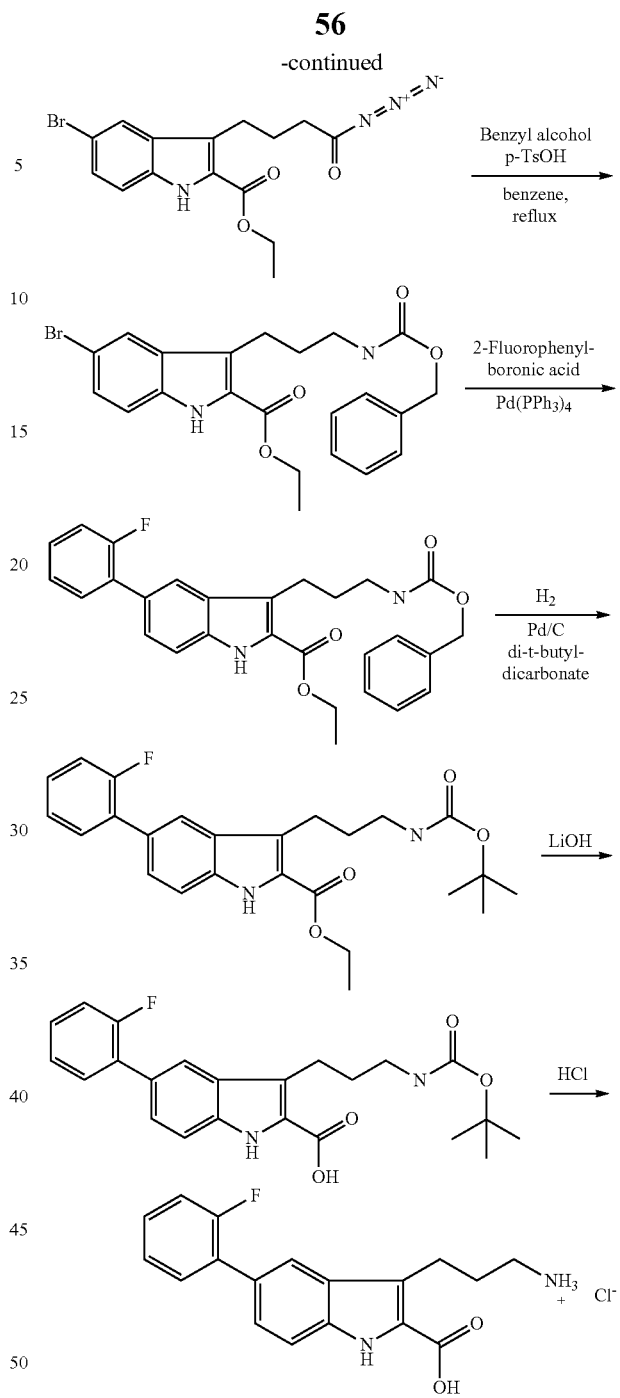

5-Bromo-3-(3-carboxy-propyl)-1H-indole-2-carboxylic acid ethyl ester (1.2 g, 3.40 mmol, 1.0 equiv) (see Example 2) was dissolved in 30 mL of acetone, cooled to −5° C. and triethylamine (0.76 ml, 5.44 mmol, 1.6 equiv) was added. To this cold solution, ethyl chloroformate (0.6 mL, 5.44 mmol, 1.6 equiv) was added dropwise and the mixture was stirred for 30 min at 0° C. A solution of sodium azide (440 mg, 6.8 mmol, 2.0 equiv) in 2 mL of water was added slowly and the mixture was stirred for a further 1 h at 0° C. The reaction mixture was then poured into ice-water (50 mL) and extracted 3×50 mL of diethyl ether. The pooled organic fractions were washed with 1×50 mL of water, 1×50 mL of saturated sodium bicarbonate, 1×50 mL of water, dried (Na$_2$SO$_4$), filtered and evaporated on the rotovap to provide 3-(3-azidocarbonylpropyl)-5-bromo-1H-indole-2-carboxylic acid ethyl ester (1.28 g, 100%) which was used without further purification.

3-(3-Azidocarbonyl-propyl)-5-bromo-1H-indole-2-carboxylic acid ethyl ester (1.28 g, 3.4 mmol, 1.0 equiv), TsOH hydrate (65 mg, 0.34 mmol, 0.1 equiv), and benzyl alcohol (0.74 mL, 6.8 mmol, 2.0 equiv) were refluxed in 30 mL of benzene for 16 h. The solution was then poured into saturated aqueous sodium bicarbonate (50 mL) and extracted with 2×50 mL of diethyl ether. The pooled organic fractions were dried ($Na_2SO_4$), filtered, and evaporated. The residue was purified by flash chromatography on silica gel using 0% EtOAc in hexanes graded to 20% EtOAc in hexanes to provide 5-bromo-3-[3-benzyloxycarbonyl-propyl]-1H-indole-2-carboxylic acid ethyl ester (1.3 g, 75%). This material was used without further manipulation.

5-Bromo-3-[3-benzyloxycarbonyl-propyl]-1H-indole-2-carboxylic acid ethyl ester (100 mg, 0.22 mmol, 1.0 equiv), $Na_2CO_3$ (95 mg, 0.9 mmol, 4.1 equiv), and 2-fluoro-phenyl-boronic acid (36 mg, 1.2 equiv) were dissolved in the biphasic mixture of degassed water/THF (each layer was homogeneous). Palladium tetrakis(triphenylphosphine) (12 mg) was added and the reaction vessel was capped and heated to 110° C. with good stirring for 16 h (black Pd had precipitated out at this point). The mixture was then cooled to room temperature and diluted with 20 mL of EtOAc and 20 mL of water. The layers were separated and the aqueous layer was extracted once with 20 mL of EtOAc. The pooled organic fractions were dried ($Na_2SO_4$), filtered, and evaporated. The crude residue was purified by flash chromatography on silica using 0% EtOAc in hexanes graded to 30% EtOAc in hexanes to provide 3-(3-benzyloxycarbonylamino-propyl)-5-(2-fluoro-phenyl)-1H-indole-2-carboxylic acid ethyl ester (33 mg, 32%). This material was used without further manipulation.

The above ethyl ester (33 mg, 0.070 mmol, 1.0 equiv) was dissolved in MeOH and $Boc_2O$ (20 mg, 0.09 mmol, 1.2 equiv) and 10% palladium on carbon (10 mg) were added. The mixture was stirred under an atmosphere of hydrogen gas (balloon) for 6 h. An aliquot was filtered and submitted for LCMS analysis, which indicated that the reaction was complete. The mixture was filtered through diatomaceous earth, washing well with methanol. The solvent was evaporated and the residue was taken up in $CH_2Cl_2$ and purified by flash chromatography using 0% EtOAc in hexanes graded to 20% EtOAc in hexanes as mobile phase to yield 3-[3-(t-butoxycarbonylamino)-propyl]-5-(2-fluoro-phenyl)-1H-indole-2-carboxylic acid ethyl ester (14 mg, 45%). This material was used without further manipulation.

The above ethyl ester (14 mg, 0.032 mmol, 1.0 equiv) was dissolved in 2 mL of 1:1 methanol/THF. To this was added a solution of lithium hydroxide hydrate (25 mg, 0.6 mmol) in 1 mL water. The reaction was heated at 50° C. for 15 min and then stirred at ambient temperature overnight. The reaction was cooled to 0° C. and acidified to pH~2 with concentrated HCl. The product was extracted with ethyl acetate (2×10 mL). The solution was dried over anhydrous sodium sulfate, filtered, and evaporated to give 3-[3-(t-butoxycarbonylamino)-propyl]-5-(2-fluoro-phenyl)-1H-indole-2-carboxylic acid (13 mg, 95%). This material was used without further manipulation.

To the above carboxylic acid (13 mg, 0.031 mmol, 1.0 equiv) in methylene chloride (2 mL) at 0° C. was added 0.2 mL of 4 N HCl in dioxane. The reaction was stirred at ambient temperature for 1 h. Then 10 mL of diethyl ether was added to the reaction and the reaction concentrated. To this residue was added 5 mL diethyl ether and the solid was filtered off and washed with diethyl ether several times and air dried for 15 min to provide the title compound (8 mg); MS, electrospray, 313 (M+H).

Using the methods described above in this Example, the following analogs were also synthesized:

3-(3-Amino-propyl)-5-(3-fluoro-phenyl)-1H-indole-2-carboxylic acid hydrochloride; MS, electrospray, 313 (M+H)

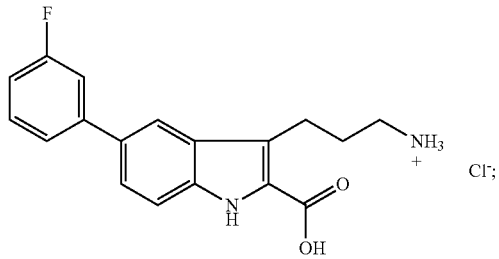

3-(3-Amino-propyl)-5-(4-fluoro-phenyl)-1H-indole-2-carboxylic acid hydrochloride; MS, electrospray, 313 (M+H)

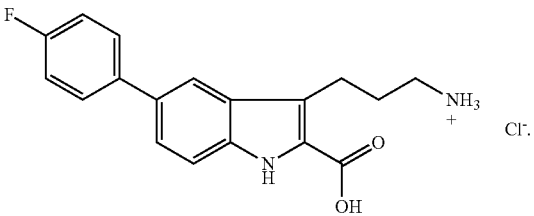

Example 4

Preparation of 5-methoxy-3-(3-aminopropyl)-1H-indole-2-carboxylic acid hydrochloride

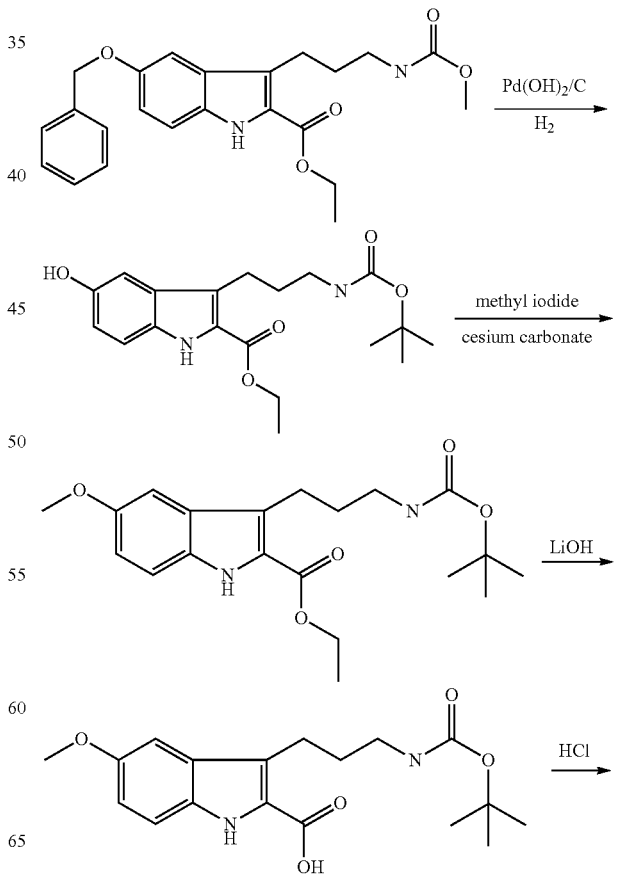

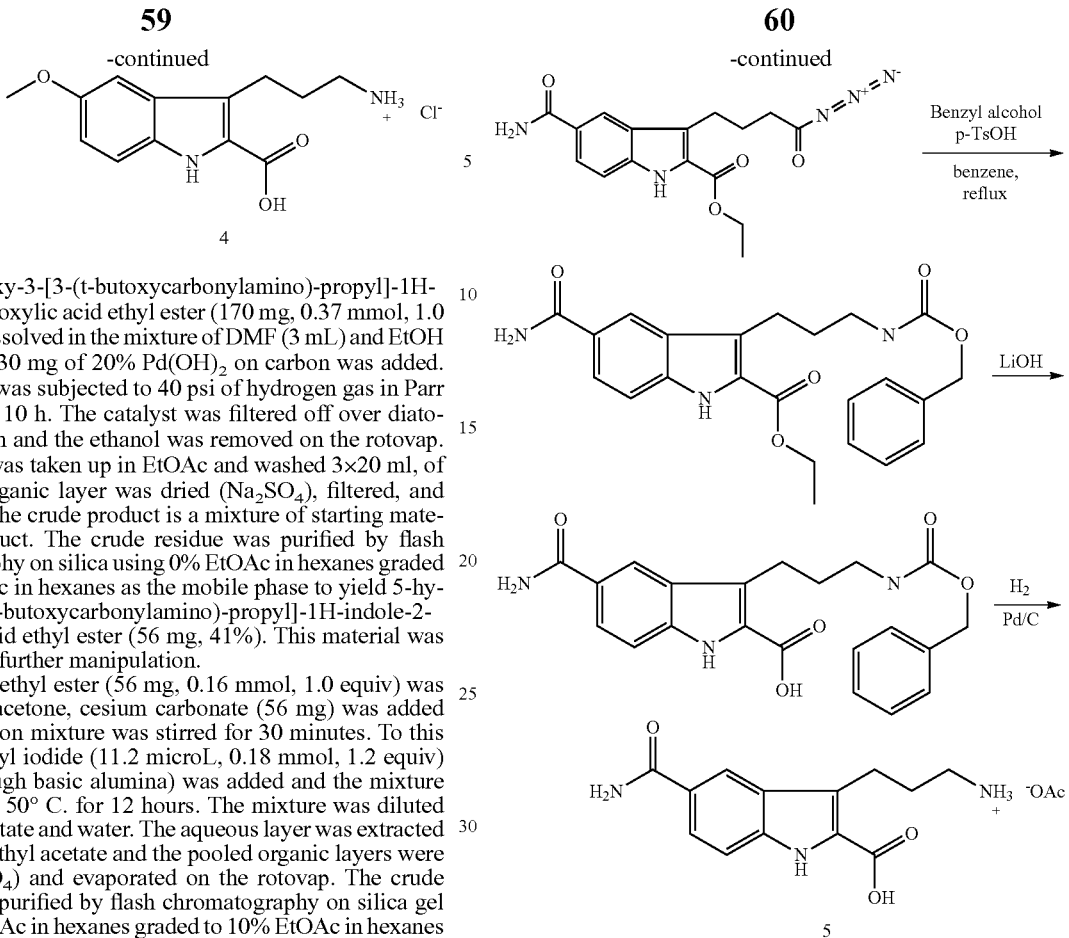

5-Benzyloxy-3-[3-(t-butoxycarbonylamino)-propyl]-1H-indole-2-carboxylic acid ethyl ester (170 mg, 0.37 mmol, 1.0 equiv) was dissolved in the mixture of DMF (3 mL) and EtOH (18 mL) and 30 mg of 20% Pd(OH)$_2$ on carbon was added. The reaction was subjected to 40 psi of hydrogen gas in Parr apparatus for 10 h. The catalyst was filtered off over diatomaceous earth and the ethanol was removed on the rotovap. The residue was taken up in EtOAc and washed 3×20 ml of brine. The organic layer was dried (Na$_2$SO$_4$), filtered, and evaporated. The crude product is a mixture of starting material and product. The crude residue was purified by flash chromatography on silica using 0% EtOAc in hexanes graded to 30% EtOAc in hexanes as the mobile phase to yield 5-hydroxy-3-[3-(t-butoxycarbonylamino)-propyl]-1H-indole-2-carboxylic acid ethyl ester (56 mg, 41%). This material was used without further manipulation.

The above ethyl ester (56 mg, 0.16 mmol, 1.0 equiv) was dissolved in acetone, cesium carbonate (56 mg) was added and the reaction mixture was stirred for 30 minutes. To this mixture methyl iodide (11.2 microL, 0.18 mmol, 1.2 equiv) (filtered through basic alumina) was added and the mixture was stirred at 50° C. for 12 hours. The mixture was diluted with ethyl acetate and water. The aqueous layer was extracted 2×15 mL of ethyl acetate and the pooled organic layers were dried (Na$_2$SO$_4$) and evaporated on the rotovap. The crude material was purified by flash chromatography on silica gel using 0% EtOAc in hexanes graded to 10% EtOAc in hexanes to yield 5-methoxy-3-[3-(t-butoxycarbonylamino)-propyl]-1H-indole-2-carboxylic acid ethyl ester (27 mg, 46%).

The above ethyl ester (27 mg, 0.072 mmol, 1.0 equiv) was dissolved in 2 mL of THF and 2 mL of ethanol. A solution of LiOH (60 mg) in 2 mL of water was added and the mixture was stirred for 6 h at 50° C. TLC (EtOAc, Rf=1.00 for SM and Rf=0.35 (streaks) for product) analysis indicated that the reaction was complete. The mixture was acidified to pH ~2 using 10% HCl and the solution was extracted 3×20 mL of EtOAc. The pooled organic phases were dried (Na$_2$SO$_4$), filtered, and evaporated on the rotovap to yield 5-methoxy-3-[3-(t-butoxycarbonylamino)-propyl]-1H-indole-2-carboxylic acid (27 mg, 100%) that was used without further manipulation.

The above carboxylic acid (27 mg) was suspended in 3 mL of dichloromethane and 0.2 mL of a 4 N solution of HCl in dioxane was added. After 3.5 h, TLC analysis (EtOAc) showed only baseline material thus 5 mL of ether was added and the resulting solid was collected by filtration and dried to yield the title compound (15 mg, 78%); MS, electrospray, 249 (M+H).

Example 5

Preparation of 5-carboxamide-3-(3-aminopropyl)-1H-indole-2-carboxylic acid acetate salt

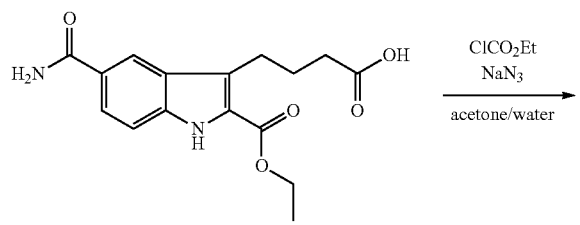

5-Carboxamide-3-(3-carboxy-propyl)-1H-indole-2-carboxylic acid ethyl ester (prepared from 4-carboxamide aniline using the same procedure described in Example 2 for the 5-bromo analog) (325 mg, 1.02 mmol, 1.0 equiv) was dissolved in 15 mL of acetone, cooled to −5° C. and triethylamine (0.25 mL, 1.8 mmol, 1.8 equiv) was added. To this cold solution, ethyl chloroformate (0.2 mL, 1.8 mmol, 1.8 equiv) was added dropwise and the mixture was stirred for 30 min at 0° C. A solution of sodium azide (145 mg, 2.25 mmol, 2.2 equiv) in 2 mL of water was added slowly and the mixture was stirred for a further 1 h at 0° C. The reaction mixture was then poured into ice-water (15 mL) and extracted 3×15 mL of diethyl ether. The pooled organic fractions were washed 1×10 mL of water, 1×10 mL of saturated sodium bicarbonate, 1×10 mL of water, dried (Na$_2$SO$_4$), filtered and evaporated on the rotovap to provide 3-(3-azidocarbonyl-propyl)-5-carboxamide-1H-indole-2-carboxylic acid ethyl ester (330 mg which was used without further purification.

The above ethyl ester (330 mg, 0.96 mmol, 1.0 equiv), TsOH hydrate (15 mg, 0.1 equiv), and benzyl alcohol (0.25 mL, 2.25 mmol, 2.3 equiv) were refluxed in 12 mL of benzene for 4 h. The solution was then poured into sat. aqueous sodium bicarbonate (12 mL) and extracted with 2×10 mL of diethyl ether. The pooled organic fractions were dried (Na$_2$SO$_4$), filtered, and evaporated. The residue was purified by flash chromatography on silica gel using 0% EtOAc in hexanes graded to 20% EtOAc in hexanes to provide 5-carboxamide-3-[3-benzyloxycarbonyl-propyl]-1H-indole-2-carboxylic acid ethyl ester (216 mg). This material was used without further manipulation.

The above ethyl ester (216 mg, 0.51 mmol, 1.0 equiv) was dissolved in 5 mL of ethanol. A solution of lithium hydroxide hydrate (0.3 g) in 5 mL of water was added to the first solution and the resulting solution was stirred for 16 h at ambient temperature. The pH was adjusted to <1 with concentrated HCl and the product was quickly extracted with 2×15 mL of ethyl acetate. The organic layers were combined, dried over Na₂SO₄, decanted and concentrated to provide 5-carboxamide-3-(3-benzyloxycarbonylamino-propyl)-1H-indole-2-carboxylic acid (200 mg) as a beige glass that was used without further manipulation.

The above carboxylic acid (127 mg, 0.32 mmol, 1.0 equiv) was dissolved in 10 mL of methanol. 10% Palladium hydroxide on carbon (15 mg) was added and the flask was sealed and a vacuum pulled over the solution. The void was refilled with hydrogen gas from a balloon and the resulting reaction mixture was stirred under 1 atmosphere of hydrogen overnight (17 h). The mixture was filtered through a plug of diatomaceous earth and the filtrate was concentrated. The residue was dissolved in 5 mL of acetic acid and diethyl ether was added with stirring until a fluffy precipitate formed. The white fluffy solid was collected by filtration and washed with 2×10 mL of ether to yield the title compound (50 mg); MS analysis electrospray, 262 (M+H).

Utilizing the above methods described in this Example, the corresponding 5-(N-methyl-carboxamide)-3-(3-aminopropyl]-1H-indole-2-carboxylic acid acetate salt was also synthesized; MS, electrospray, 276 (M+H)

Example 6

Preparation of 5-(benzyloxycarbonyl)-amino-3-(3-aminopropyl]-1H-indole-2-carboxylic acid hydrochloride

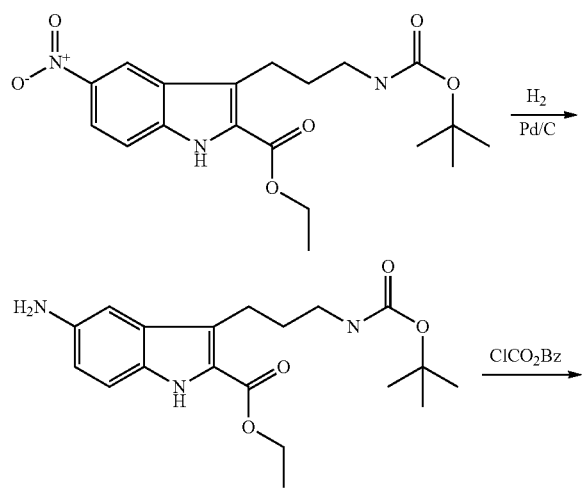

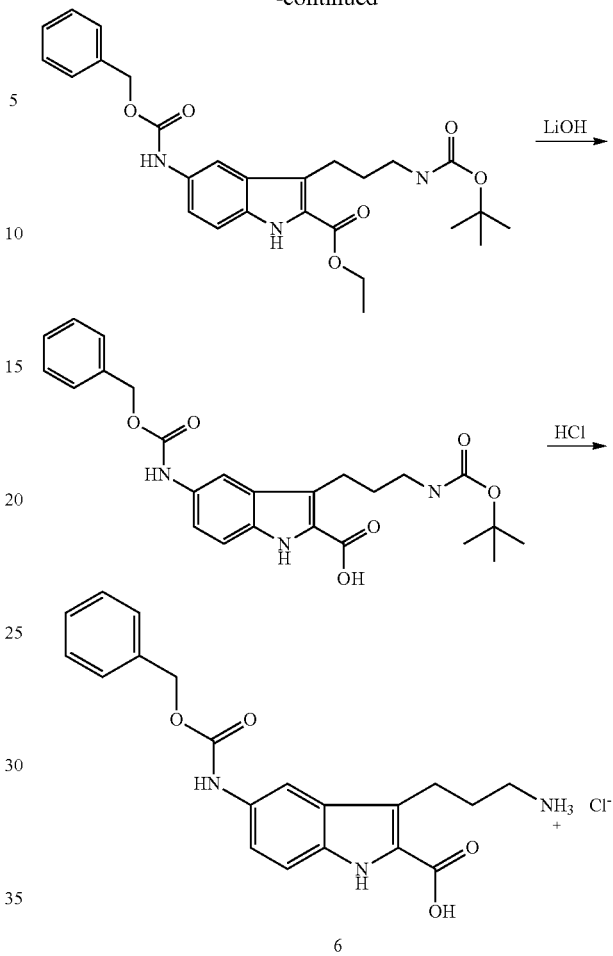

5-Nitro-3-[3-(t-butoxycarbonylamino)-propyl]-1H-indole-2-carboxylic acid ethyl ester (prepared by the procedure described in Example 2 for the 5-bromo analog) (426 mg) was dissolved in 20 mL of methanol. Palladium on carbon (85 mg) was added and the flask was seal with a rubber septum. A vacuum was pulled through a needle and the void was refilled from a balloon of hydrogen gas. The resulting mixture was stirred under 1 atm of hydrogen gas for 17 h. In the morning, LCMS analysis revealed consumption of the starting material and formation of the product. The reaction mixture was filtered through diatomaceous earth and concentrated under vacuum to yield 5-amino-3-[3-(t-butoxycarbonylamino)-propyl]-1H-indole-2-carboxylic acid ethyl ester as an orange foam (432 mg, solvent trapped within). This material was used without further manipulation.

5-Amino-3-[3-(t-butoxycarbonylamino)-propyl]-1H-indole-2-carboxylic acid ethyl ester (125 mg) was dissolved in 10 mL of THF. To the solution was added 0.5 mL of benzylchloroformate and 0.5 mL of triethylamine. The resulting solution was stirred at ambient temperature overnight (16 h). In the morning the reaction mixture was diluted with 20 mL of water and 20 mL of diethyl ether. The layers were separated and the aqueous layer was washed with 20 mL of diethyl ether. The organic layers were combined and dried over sodium sulfate. After decantation, the solvent was removed on the rotary evaporator. The residue was purified by flash chromatography on silica using 5% EtOAc in hexanes graded to 50% EtOAc in hexanes as the mobile phase to yield 5-(benzyloxycarbonyl)-amino-3-[3-(t-butoxycarbonylamino)-propyl]-1H-indole-2-carboxylic acid ethyl ester (101 mg). This material was clean by 1H NMR and used in the next step without further purification.

The above ethyl ester (101 mg), was dissolved in 5 mL of methanol. To the solution, was added 150 mg of lithium hydroxide hydrate and 1 mL of water. The reaction was stirred at 50° C. for 2 h at which time LCMS analysis indicated formation of the desired product and consumption of the starting material. The reaction was cooled and neutralized to pH of about 2 with drops of 10% HCl in water. Water (15 mL) was added and the resulting solid was collected by filtration, washed with 2×5 mL of water and dried under vacuum to yield 5-(benzyloxycarbonyl)-amino-3-[3-(t-butoxycarbonylamino)-propyl]-1H-indole-2-carboxylic acid (72 mg) as an off-white solid. $^1$H NMR showed the product to be greater than 95% pure. This material was used in the next step without further manipulation.

5-(Benzyloxycarbonyl)-amino-3-[3-(t-butoxycarbonylamino)-propyl]-1H-indole-2-carboxylic acid (72 mg) was dissolved in 5 mL of 4 N HCl in dioxane. Within 10 min a white crystalline solid had formed. The mixture was stirred for 45 min at which time the reaction was diluted with 10 mL of methylene chloride. The filtrate was removed with a filter-tipped cannula and the solid was washed 3×10 mL of methylene chloride and dried, providing the title compound; MS, electrospray, 369 (M+H).

Example 7

Preparation of 5-benzoylamino-3-(3-aminopropyl]-1H-indole-2-carboxylic acid hydrochloride

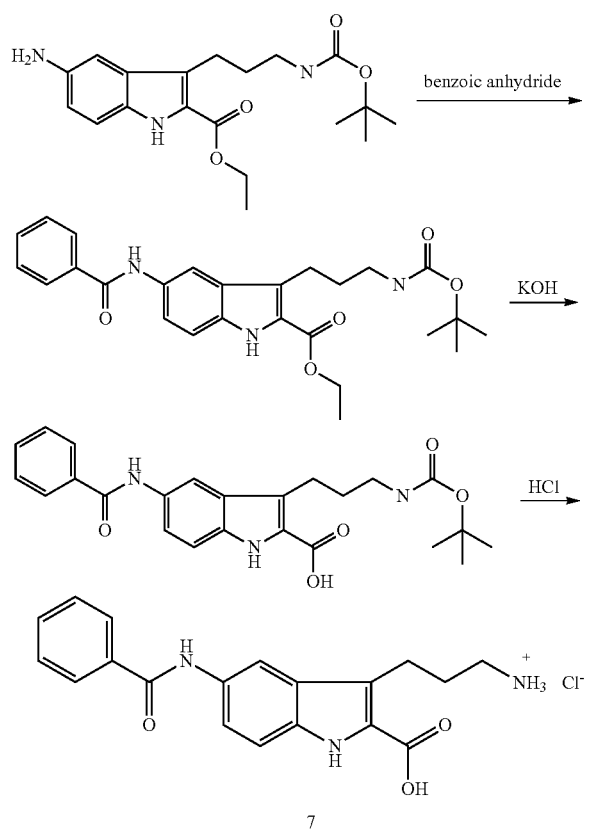

5-Amino-3-[3-(t-butoxycarbonylamino)-propyl]-1H-indole-2-carboxylic acid ethyl ester (40 mg, 0.11 mmol, 1.0 equiv) was dissolved in 10 mL of methylene chloride and 1 mL of triethylamine. Benzoic anhydride (45 mg, 0.20 mmol, 1.8 equiv) was added and the solution was stirred overnight. In the morning the reaction was washed with 10 mL of water and the organic layer was concentrated. The crude residue was purified by flash chromatography on silica using 0% ethyl acetate in methylene chloride graded to 100% ethyl acetate over 30 min to yield 5-benzoylamino-3-[3-(t-butoxycarbonylamino)-propyl]-1H-indole-2-carboxylic acid ethyl ester (43 mg). This material was used without further manipulation.

The above ethyl ester (43 mg) was dissolved in 10 mL of a 50/50 mixture of THF and ethanol. A solution of 1 g KOH in water (5 mL) was added and the resulting solution was stirred at ambient temperature overnight (17 h). In the morning, the reaction solution was diluted with 40 mL of water and the pH adjusted to about 2 with conc. HCl. The resulting milky mixture was extracted with 2×10 mL of ethyl acetate and the organics were combined, dried over $Na_2SO_4$ and concentrated to yield 5-benzoylamino-3-[3-(t-butoxycarbonylamino)-propyl]-1H-indole-2-carboxylic acid (31 mg). This material was used without further purification.

The above carboxylic acid (31 mg) was dissolved in 5 mL of 4N HCl in dioxane. Within 2 min a white precipitate had formed. The mixture was stirred for 45 min and then diluted with 10 mL of methylene chloride. The solid was filtered with a filter-tipped cannula and washed with 2×10 mL of methylene chloride. The solid was dried under vacuum to provide the title compound; MS, electrospray, 339 (M+H)

Example 8

Preparation of 5-ureido-3-(3-aminopropyl]-1H-indole-2-carboxylic acid hydrochloride

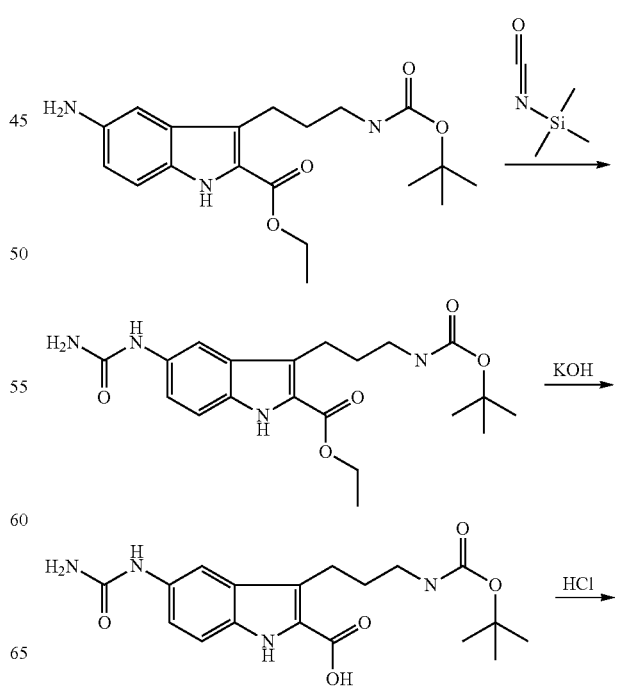

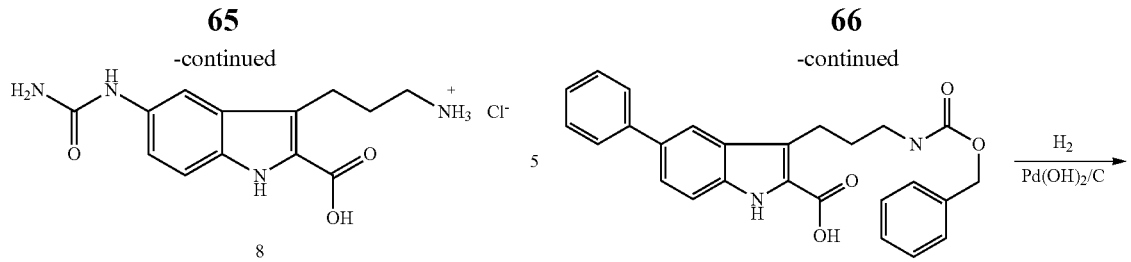

8

5-Amino-3-[3-(t-butoxycarbonylamino)-propyl]-1H-indole-2-carboxylic acid ethyl ester (40 mg, 0.11 mmol, 1.0 equiv) was dissolved in 10 mL of methylene chloride and 1 mL of triethylamine. Trimethylsilyl isocyanate was added and the solution was stirred overnight. In the morning the reaction was washed with 10 mL of water and the organic layer was concentrated. The crude residue was purified by flash chromatography on silica (10 g of $SiO_2$) using 0% ethyl acetate in methylene chloride to 100% ethyl acetate graded over 25 min at a flow rate of 15 mL/min-then 100% ethylacetate for another 15 min. The fractions with pure product (TLC) were combined and concentrated to provide 5-ureido-3-[3-(t-butoxycarbonylamino)-propyl]-1H-indole-2-carboxylic acid ethyl ester as a white solid (41 mg). This material was used without further purification.

The above ethyl ester (41 mg) was dissolved in 10 mL of ethanol. A solution of 1 g KOH in water (5 mL) was added and the resulting solution was stirred at ambient temperature overnight. In the morning the reaction solution was diluted with 40 mL of water and the pH adjusted to about 2 with conc. HCl. The resulting clear solution was extracted with 3×20 mL of ethyl acetate and the organics were combined, dried over $Na_2SO_4$ and concentrated to provide 5-ureido-3-[3-(t-butoxycarbonylamino)-propyl]-1H-indole-2-carboxylic acid (32 mg).

The above carboxylic acid (31 mg) was dissolved in 10 mL of 4N HCl in dioxane. The mixture was spun on the rotovap without vacuum for 45 min. The solid was filtered with a filter-tipped cannula and washed with 2×10 mL of methylene chloride. The solid was dried under vacuum to yield the title compound (21 mg); MS, electrospray, 278 (M+H).

Example 9

Preparation of 5-phenyl-3-(3-aminopropyl)-1H-indole-2-carboxylic acid acetate salt

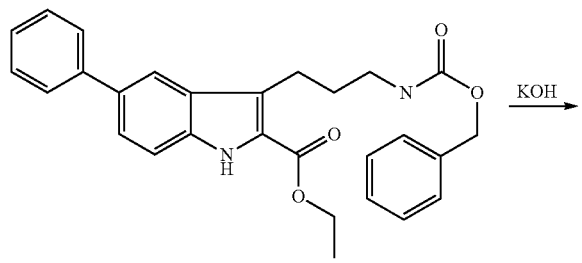

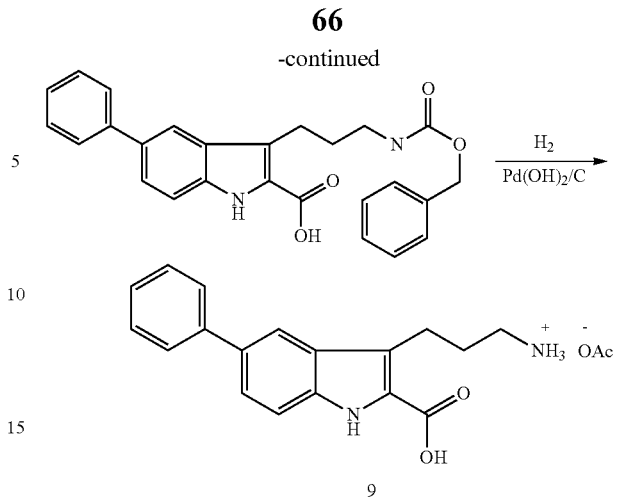

9

5-Phenyl-3-[3-benzyloxycarbonyl-propyl]-1H-indole-2-carboxylic acid ethyl ester (40 mg, 0.088 mmol, 1.0 equiv) was dissolved in 4 mL of a 1:1 mixture of THF and ethanol. To this homogenous solution, KOH in water was added and the reaction mixture was stirred at 50° C. for 6 h. At this point TLC (100% EtOAc) showed only baseline material. The reaction was poured into 20 mL of 1 M HCl and was extracted 2×25 mL of EtOAc. The pooled organic fractions were dried ($Na_2SO_4$), filtered, and evaporated to yield 5-phenyl-3-[3-benzyloxycarbonyl-propyl]-1H-indole-2-carboxylic acid (34 mg, 90%).

The above carboxylic acid (34 mg) and the $PdOH_2$ on carbon catalyst (30 mg) were stirred in methanol under an atmosphere of hydrogen gas (balloon) for 16 h. A white precipitate had formed. Ether (10 mL) was added and the mixture was filtered through filter paper. Acetic acid (2 mL) was added to the solid to dissolve the desired product and the mixture was filtered through filter paper. Ether (20 mL) was added which failed to precipitate the product, the ether was removed under vacuum and the product was dissolved in 1 mL of methanol and water (20 mL) was added. A fluffy white precipitate was isolated (2.8 mg); MS, electrospray, 295 (M+H).

Example 10

Preparation of 3-(3-Benzyloxycarbonylamino-propyl)-1H-indole-2,5-dicarboxylic acid 2-ethyl ester (Method A)

This procedure illustrates the synthesis of an intermediate useful in preparing compounds of the invention.

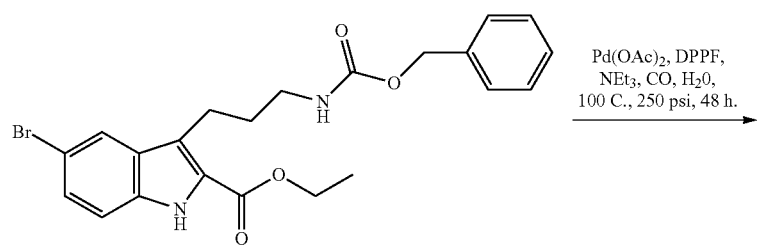

-continued

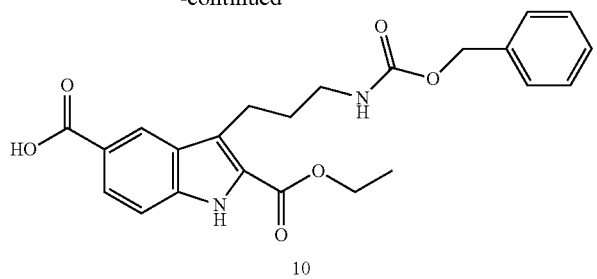

A pressure reactor was charged with a solution of 5-bromo-3-[3-benzyloxycarbonyl-propyl]-1H-indole-2-carboxylic acid ethyl ester (750 mg, 1.6 mmol), in DMF (8 mL). Water (1.5 ml, 18.0 mmol) was added, followed by triethylamine (2.2 mL, 16.3 mmol). Palladium acetate (367 mg, 1.6 mmol) was added, followed by 1,1-bis(diphenylphosphino)ferrocene (453 mg, 0.8 mmol). The reactor was flushed with Argon, sealed, pressurized with carbon monoxide to 250 psi. and heated to 100° C. for 48 h. The reaction mixture was diluted with EtOAc and washed with 1N HCl. The organic layer was passed through a plug of diatomaceous earth. The filtrate was evaporated and the resulting oil was purified by flash chromatography, eluting with 20-100% ethyl acetate/hexane and finally with EtOAc containing 1% TFA to give the title compound (300 mg, 43%).

Example 11

Preparation of 3-(3-Benzyoloxycarbonylaminopropyl)-1H-indole-2,5-dicarboxylic acid 2-methyl ester (Method B)

This procedure illustrates the synthesis of an intermediate useful in preparing compounds of the invention.

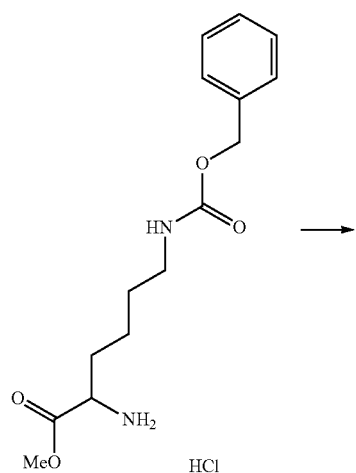

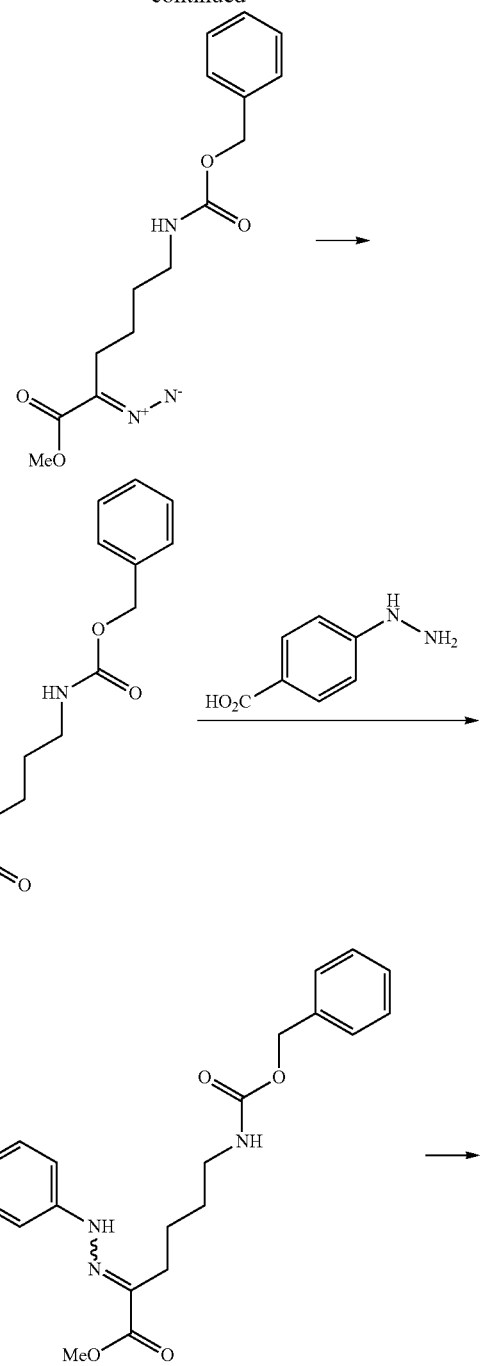

-continued

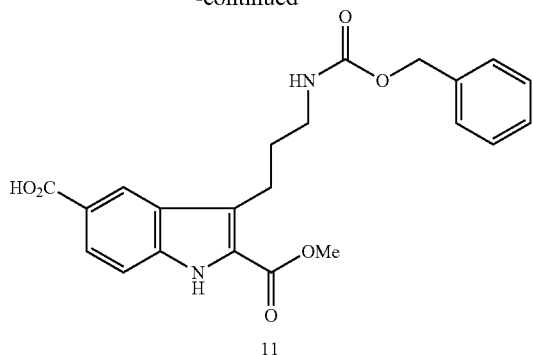

11

As would be known to one skilled in the art, epsilon-benzyloxycarbonyl-L-lysine methyl ester hydrochloride (5.00 g, 15.1 mmol) was partitioned between $CH_2Cl_2$ and aqueous $Na_2CO_3$ solution. The organic layer was dried over $MgSO_4$ and evaporated. To a solution of the resulting free base in $CHCl_3$ (75 mL) was added t-butyl nitrite (2.26 mL, 19 mmol) and HOAc (181 microL, 3.16 mmol), and the solution was stirred and heated to reflux for 2 h, by which time no starting material remained by ninhydrin stain. The cooled solution was used directly in the next step.

The $CHCl_3$ solution was cooled in ice bath to 2° C. Solid m-chloroperoxybenzoic acid (m-CPBA) (80%, 3.26 g, 15.1 mmol) was added over 2 min. Initial addition was endothermic as m-CPBA dissolved. When the addition was complete, the temperature was allowed to rise, and was maintained at 5-10° C. for 30 min. Gas evolution was seen. After 30 min gas evolution had almost ceased. The mixture was warmed to 15° C. for a further 15 min. After 50 min the solution was washed with aqueous $Na_2CO_3$ solution. The aqueous layer was extracted with $CH_2Cl_2$ and the combined organic layers were dried over $MgSO_4$ and evaporated. The product was purified by flash chromatography, eluting with hexane/EtOAc (7:3). The first-eluted spot contained a by-product which co-eluted with the diazoester. The second-eluted spot was the desired 6-benzyloxycarbonylamino-2-oxo-hexanoic acid methyl ester (2.47 g, 56%). This contained some minor impurities, but was used directly in the next step.

4-Hydrazinobenzoic acid (1.15 g, 7.58 mmol) was dissolved in acetic acid (25 mL) and water (20 mL) with warming. The resulting solution was stirred and cooled in an ice-bath to +5° C. A solution of the above ketoester (2.47 g, 8.42 mmol) in acetic acid (15 mL) was added over 2 min and stirring at 2-5° C. was continued. After 20 min the solution became cloudy, and a precipitate formed. After 1.5 h, more water (20 mL) was added to complete precipitation. The precipitate was filtered, washed with water and dried to give the desired hydrazone (2.55 g, 71%), as a 10:1 ratio of E/Z isomers by HPLC.

Concentrated sulfuric acid (0.61 g, 6.2 mmol) was added dropwise to acetic acid (35 mL). To the resulting solution was added the above hydrazone (1.76 g, 4.12 mmol). The stirred mixture was heated in an oil bath at 80° C. The reaction was followed by HPLC. The two peaks of the hydrazone E and Z isomers, which interconvert, were gradually converted to a mixture of the desired product and the indole free amine formed by loss of the benzyloxycarbonyl protecting group. After 7 h very little hydrazone was evident. The reaction mixture was cooled and solid sodium acetate (1.08 g, 13.2 mmol) was added to neutralize the sulfuric acid. The acetic acid was evaporated, finally using water and toluene azeotropes to leave a yellow solid. A solution of $Na_2CO_3$ (1.34 g, 12.6 mmol) in water (40 mL) and THF (40 mL) was used to dissolve yellow solid residue. Benzyl chloroformate (0.29 mL, 2.1 mmol) was added, and the mixture stirred for 3 h at room temperature. HPLC showed conversion of the free amine back to the desired product. The mixture was diluted with EtOAc and washed with water. The organic layer was dried over $MgSO_4$ and evaporated to give a pale yellow solid, 1.78 g. The solid was refluxed with EtOAc (10 mL) for 30 min (did not all dissolve), cooled and filtered to give the title compound (1.00 g, 59%), pure by NMR and HPLC. The filtrate contained more product by TLC. Purification of the filtrate by flash chromatography, eluting with $CH_2Cl_2$/MeOH, 97:3 yielded additional product, 175 mg, with slight impurities.

Example 12

Preparation of 3-(3-Amino-propyl)-5-phenylcarbamoyl-1H-indole-2-carboxylic acid acetate salt

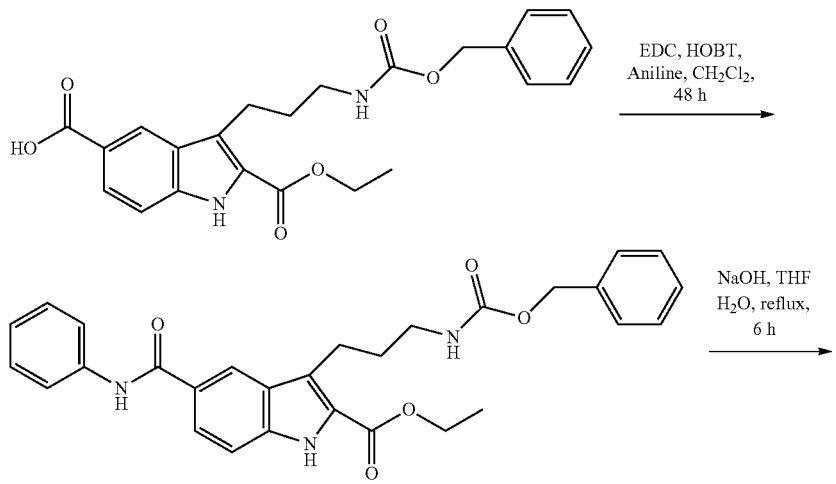

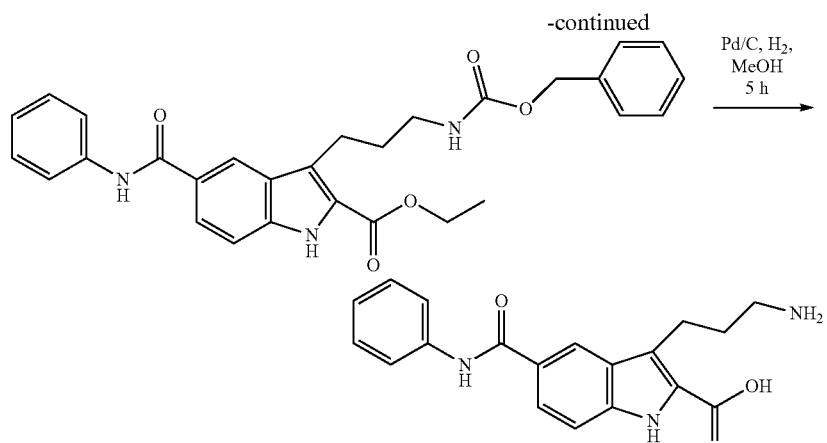

A reaction flask equipped with a nitrogen line and a stir bar was charged with a solution of 3-(3-benzyloxycarbonylamino-propyl)-1H-indole-2,5-dicarboxylic acid 2-ethyl ester (64 mg, 0.15 mmol) in dichloromethane (2 mL) and DMSO (1 mL). 1-(3-dimethylaminopropyl)-3-ethylcarbodiimide hydrochloride (37.5 mg, 0.19 mmol) and 1-hydroxybenzotriazole hydrate (26.5 mg, 0.19 mmol) were added. The reaction mixture was stirred for 0.5 h. Aniline (20.5 microL, 0.23 mmol) was added and stirring continued for 48 h. The reaction mixture was diluted with ethyl acetate and washed in turn with 1N HCl. and saturated sodium carbonate. The organic layer was dried with anhydrous sodium sulfate. The solvent was evaporated and the resulting oil was purified by flash chromatography with 50-100% ethyl acetate/hexane to give 3-(3-benzyloxycarbonylamino-propyl)-5-phenylcarbamoyl-1H-indole-2-carboxylic acid ethyl ester (44 mg, 58%).

A reaction flask equipped with a nitrogen line and a stir bar was charged with the above ethyl ester (44 mg, 0.09 mmol) in methanol (2.5 mL) and water (2.5 mL). Sodium hydroxide (25 mg, 0.63 mmol) was added, followed by THF (1 mL). The reaction mixture was refluxed for 6 h at 100° C. The solvent was evaporated and water was added. The aqueous layer was acidified with 1N HCl to pH 2. The product was extracted with ethyl acetate. The organic layer was dried with anhydrous magnesium sulfate. The solvent was evaporated to give (3-benzyloxycarbonylamino-propyl)-5-phenylcarbamoyl-1H-indole-2-carboxylic acid, which was used in the next step without any purification.

A reaction flask equipped with a stir bar was charged with a solution of the above carboxylic acid (40 mg, 0.08 mmol) in methanol (10 mL). 10% Palladium on carbon (20 mg) was added. The reaction mixture was sealed with a rubber septum and the air was evacuated under house vacuum. A balloon filled with hydrogen gas was attached to the flask, and the reaction mixture was stirred for 5 h. The mixture was filtered through diatomaceous earth and the filtrate was evaporated. The residue was washed with 2 mL of ether and 2 mL of hexane. The product was dried and 5 mL of acetic acid was added. The acetic acid was evaporated under high vacuum to give the title compound as the acetate salt (25 mg, 71%).

The compounds listed below were prepared in an analogous manner.

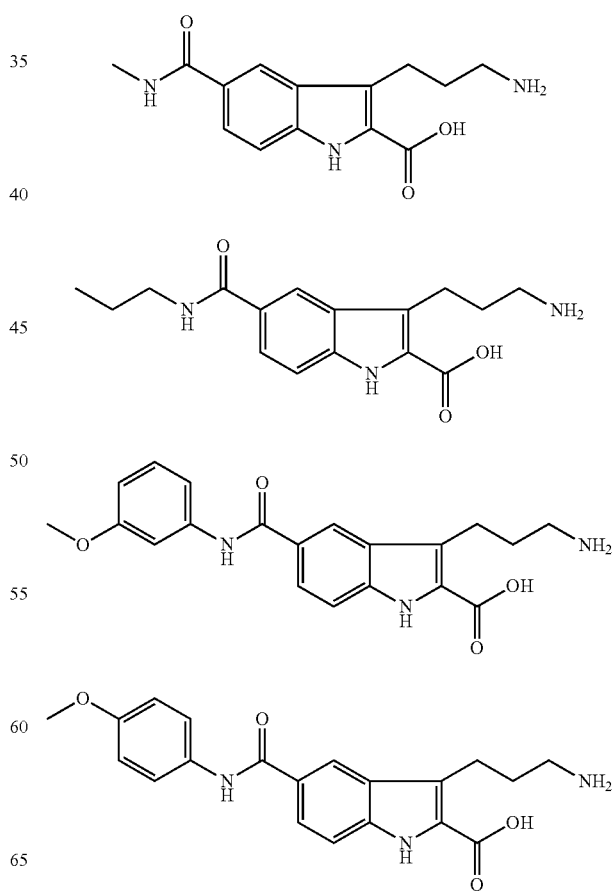

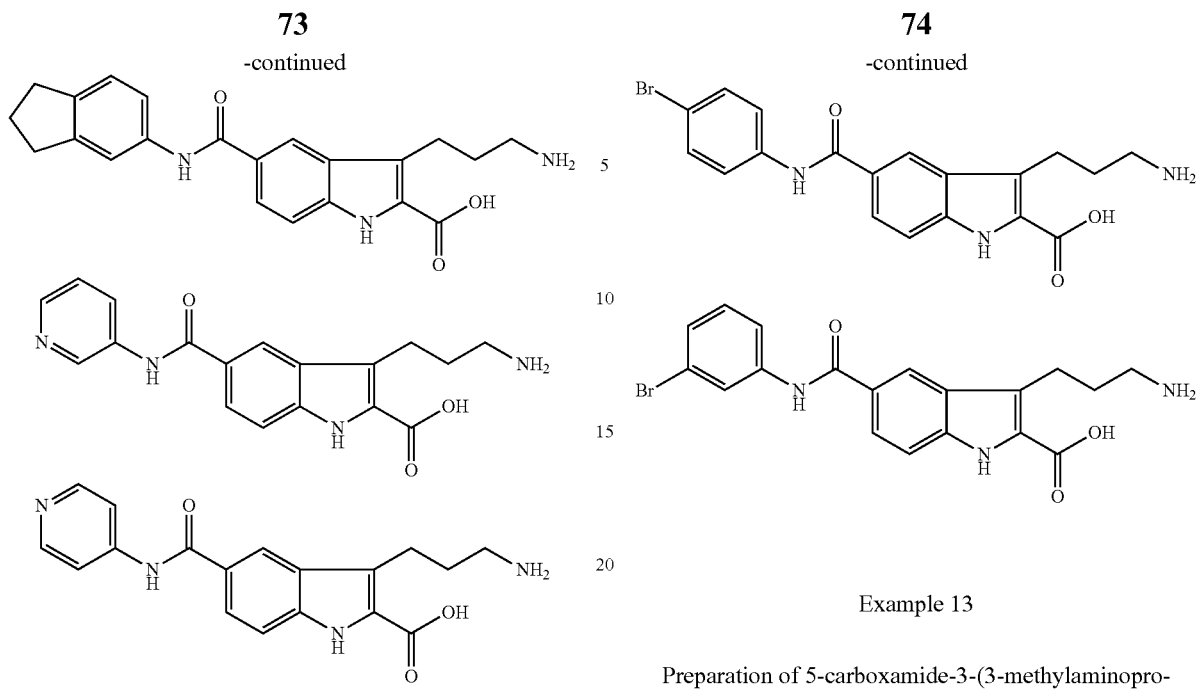
Example 13
Preparation of 5-carboxamide-3-(3-methylaminopropyl)-1H-indole-2-carboxylic acid
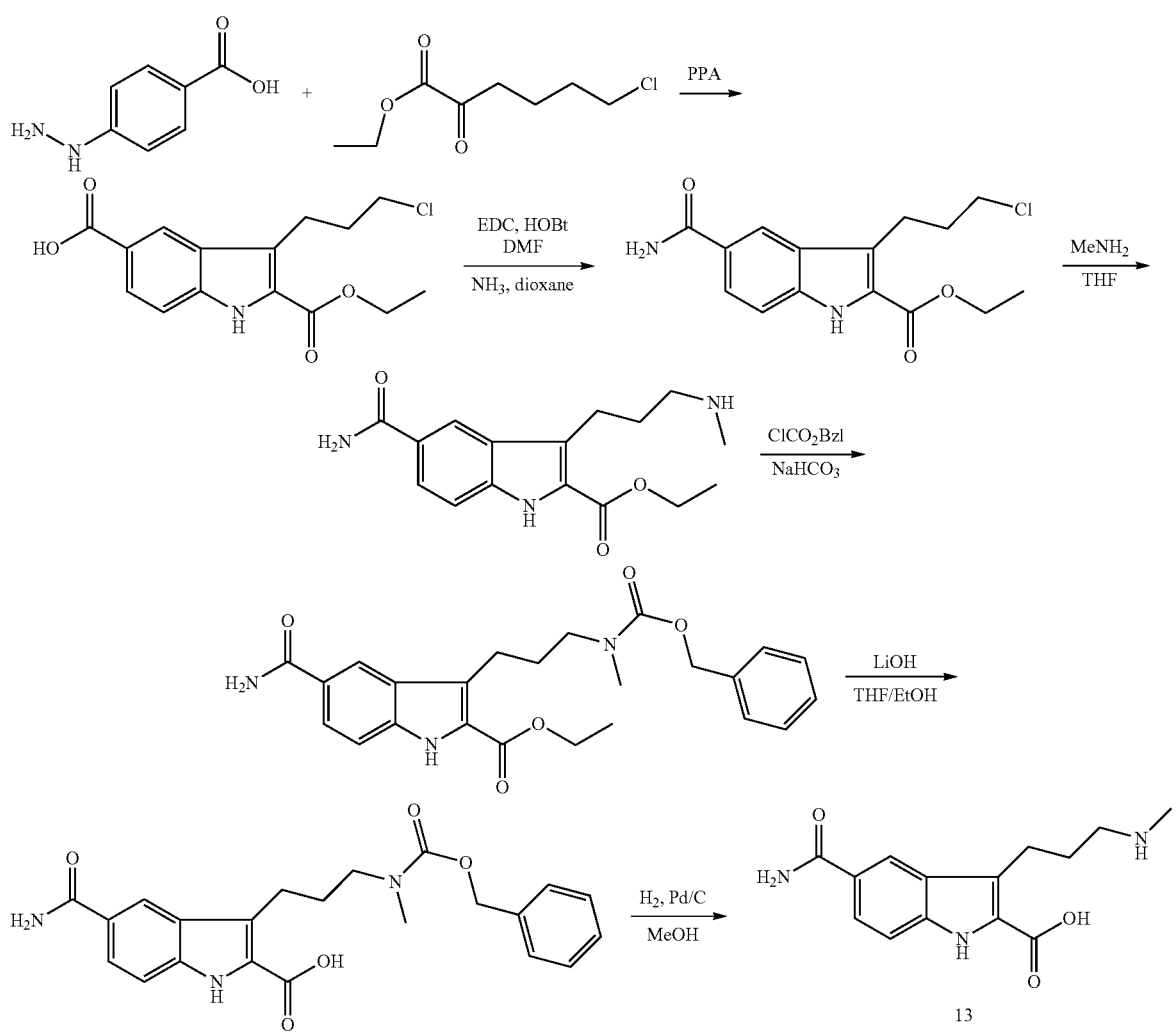

4-Hydrazinobenzoic acid (460 mg, 3.02 mmol) and ethyl 6-chloro-2-oxohexanoate (580 mg, 3.01 mmol) were combined with 10 mL polyphosphoric acid in an Erlenmeyer flask. The reaction mixture was heated to 115° C. and stirred at this temperature for 1 hour. The mixture was allowed to cool and added to 100 mL ice water, after which time it was extracted with 5×40 mL dichloromethane. The combined extracts were washed with saturated aqueous sodium bicarbonate and brine, dried with sodium sulfate, and evaporated to 838 mg. The product was purified by flash chromatography using a gradient of 10-20% methanol in dichloromethane as eluant, providing 680 mg, 73% yield.

The above acid (315 mg, 1.13 mmol) was dissolved in DMF (8 mL). The solution was cooled to 0° C. under $N_2$. EDC (239 mg, 1.25 mmol) then HOBt (169 mg, 1.25 mmol) were added as solids. The resulting mixture was stirred for 2 hours while the temperature gradually warmed to room temperature. The reaction mixture was again cooled to 0° C., and a solution of ammonia in dioxane (6 mL, 0.5M, 3 mmol) was added via syringe. The resulting mixture was stirred overnight at room temperature, poured into brine, and extracted with 4×20 mL ethyl acetate. The combined extracts were washed with saturated aqueous $NaHCO_3$ and brine, then dried and evaporated. The oily residue was triturated with dichloromentane and 95.4 mg of product was isolated by filtration. The mother liquors were evaporated and the residue was purified by flash chromatography using a gradient of 15-75% ethyl acetate in hexane as eluant. A second portion of product (53 mg) was isolated. The combined yield was 148.4 mg, 42%.

The above ester (75 mg, 0.24 mmol) was dissolved in a 2 M solution of methylamine in THF (15 mL) in a pressure tube. The tube was sealed and the reaction mixture was stirred at room temperature for 3 days, then heated at 65° C. for 4 days. The solvents were evaporated and the residue was taken up in 1N HCl (30 mL). The solution was washed with 2×25 mL ethyl acetate, then neutralized with saturated aqueous $NaHCO_3$. The product could not be extracted from the aqueous solution, therefore the aqueous solution was treated directly with benzylchloroformate (60 mg, 0.35 mmol) dissolved in 25 mL chloroform. The resulting mixture was stirred at room temperature overnight. The organic fraction was separated and evaporated. The residue was purified by flash chromatography using a gradient of 50-75% ethyl acetate in hexane. The product was isolated as a white solid, 58 mg, 55%.

The above ester (58 mg, 0.13 mmol) was dissolved in THF (1 mL) in a reaction tube. Lithium hydroxide monohydrate (70 mg, 1.38 mmol) was ground and slurried in EtOH (1 mL) and added to the solution of the ester. The tube was sealed and the reaction mixture was heated at 60° C. for 3 hours, then 35° C. for an additional 16 hours. LCMS indicated the reaction was approximately 80% complete. The reaction mixture was heated an additional 16 hours at 60° C., cooled, and poured into water (10 mL). The resulting mixture was washed with 2×15 mL ethyl acetate, neutralized with a few drops of conc HCl, and extracted with 2×15 mL ethyl acetate. The final extracts were combined, and washed with brine, dried with $Na_2SO_4$ and evaporated to give 49 mg (90%) of the carboxylic acid as a white solid.

The above carboxylic acid (38 mg, 0.09 mmol) was dispersed in MeOH (3 mL) in a reaction tube. The tube was swept with $N_2$ and Pd/C (5 mg) was added. The tube was sealed with a septum and evacuated with vacuum followed by introduction of $N_2$. The tube was again evacuated with vacuum and $H_2$ was introduced via a balloon. The reaction mixture was stirred at room temperature for 4 hours, after which time the balloon was removed and the tube was evacuated with vacuum followed by introduction of $N_2$. The catalyst was then filtered from the reaction mixture and the resulting solution was evaporated to give 28 mg of the title compound which was triturated in $Et_2O$/MeOH to a white solid (22 mg, 86%). ESMS: m/z 275 (M+H), mp 266-8 dec.

The compounds listed below may also be prepared by the methods described above:

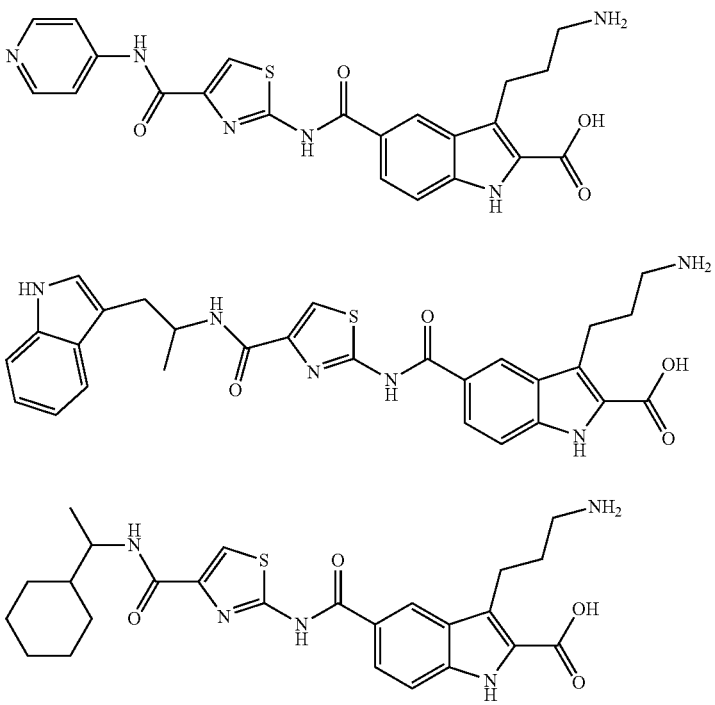

-continued
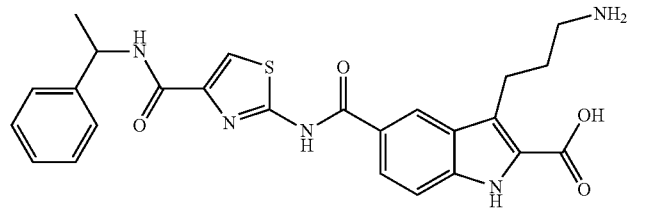
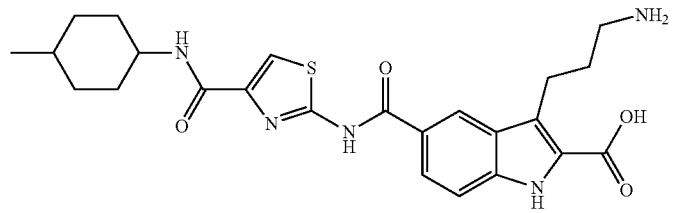
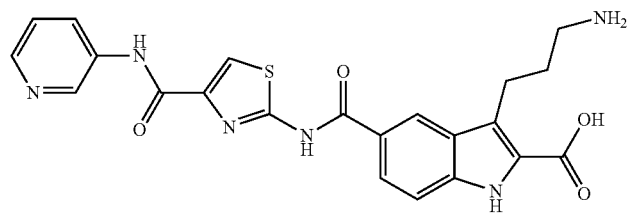
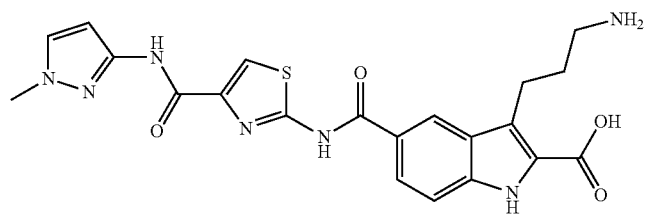
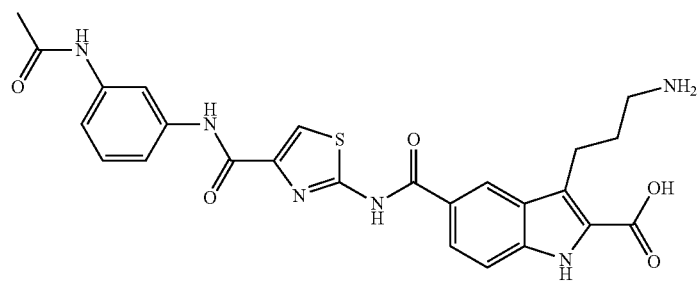
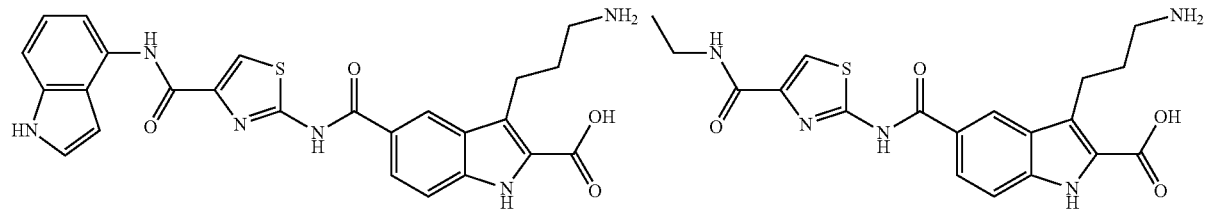
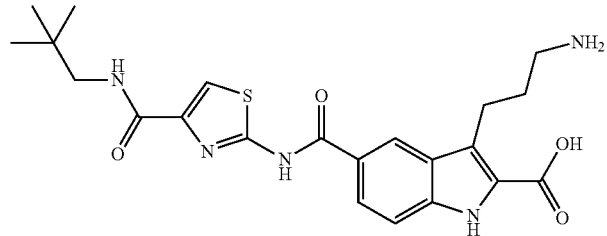

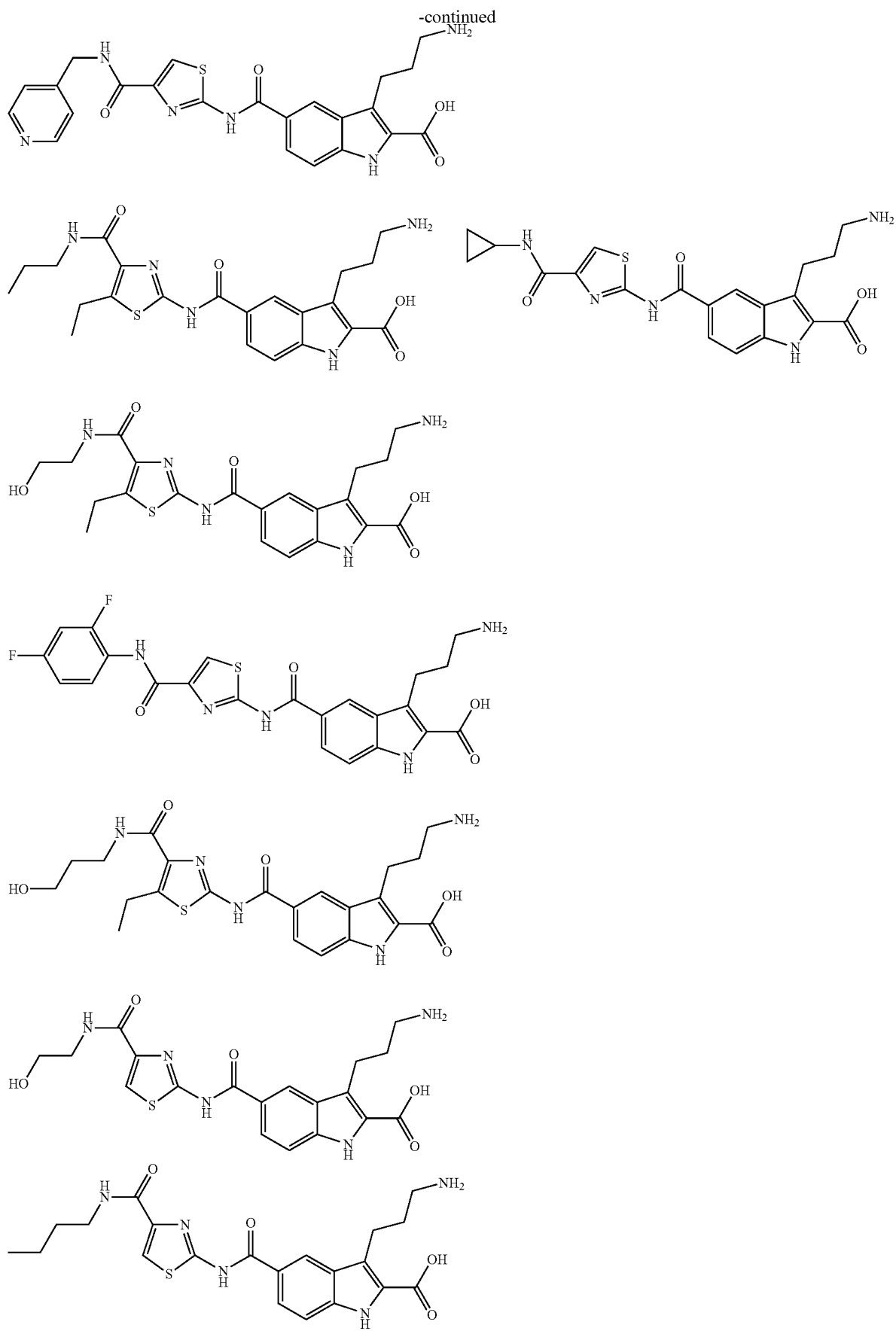

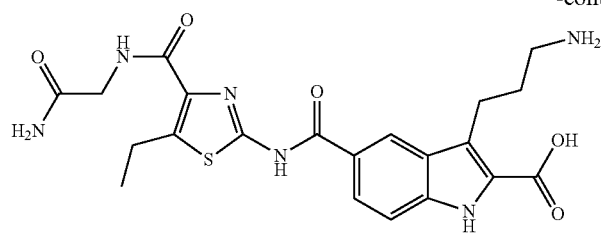
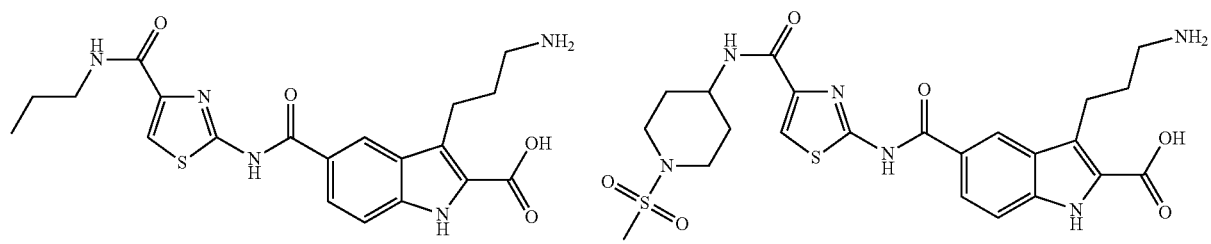
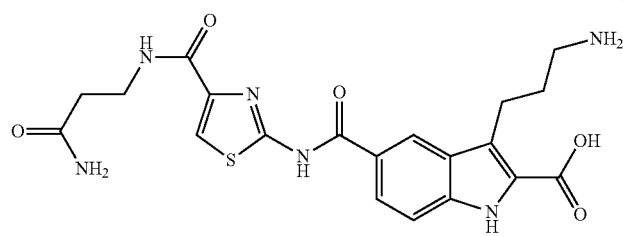
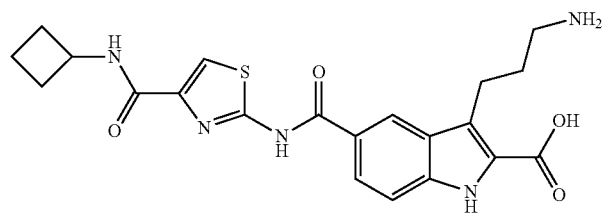
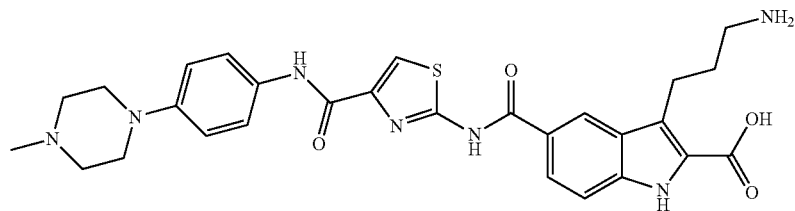
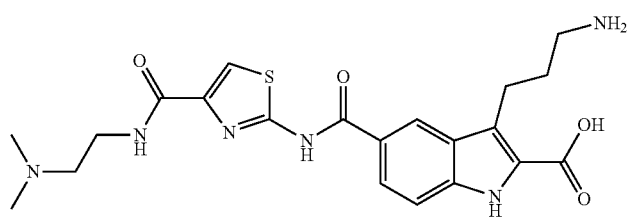
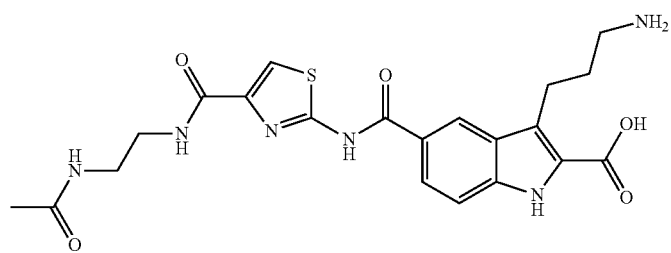

-continued
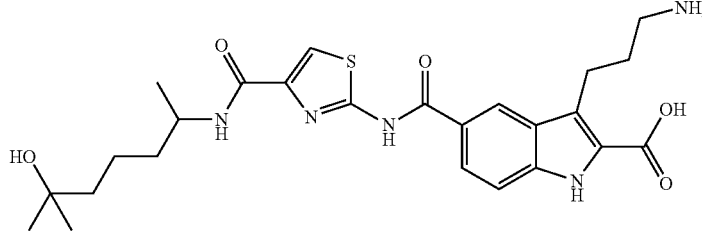
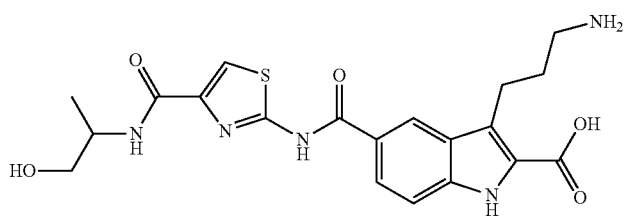
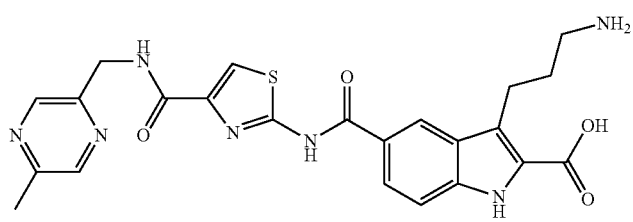
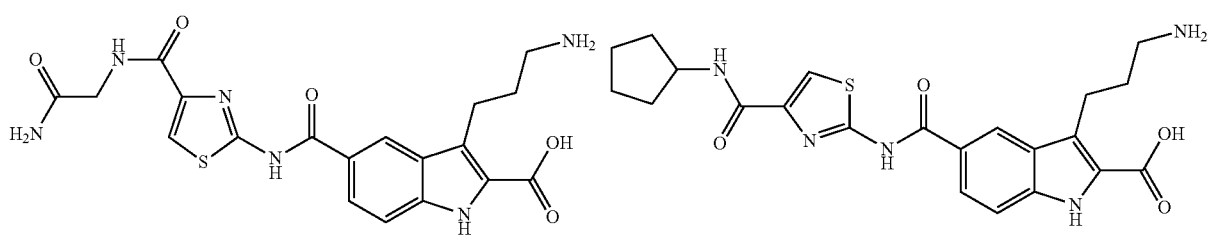
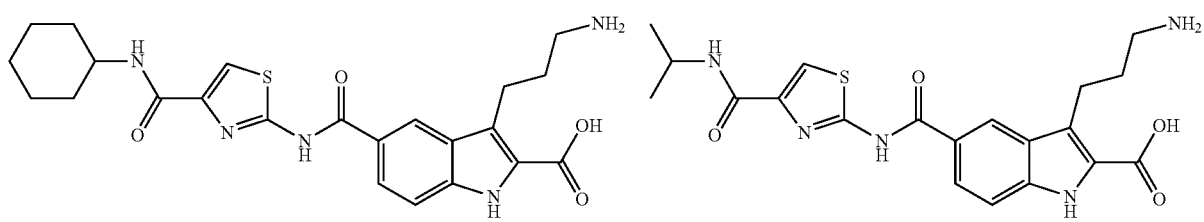
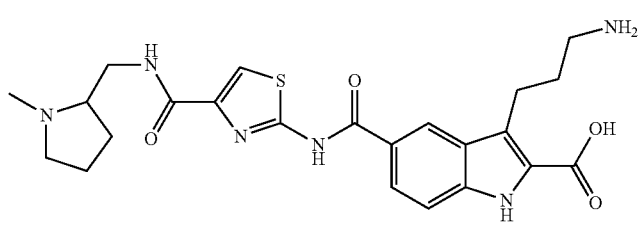
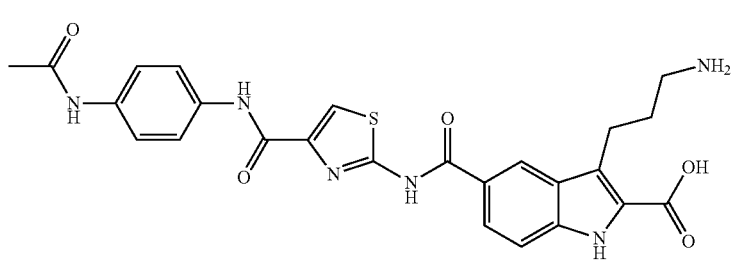

-continued
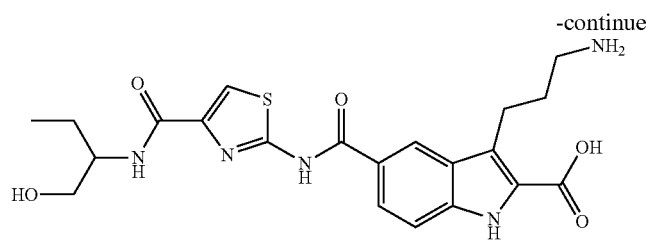
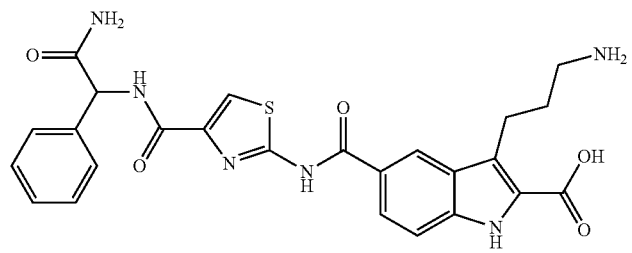
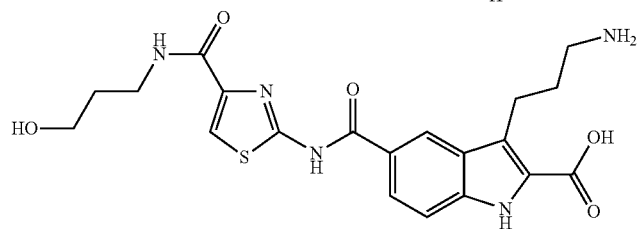
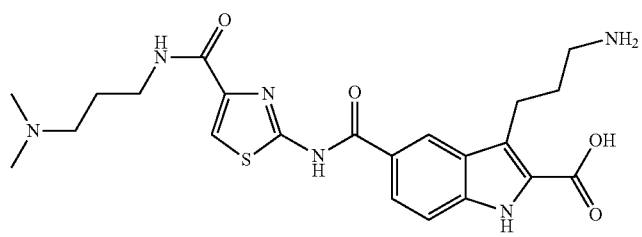
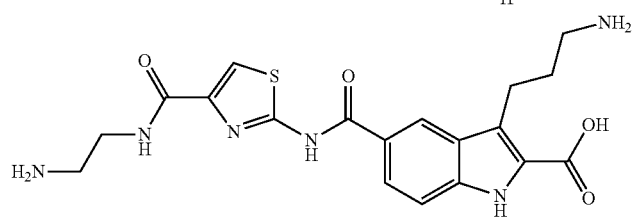
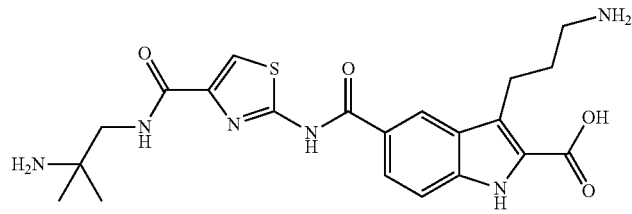
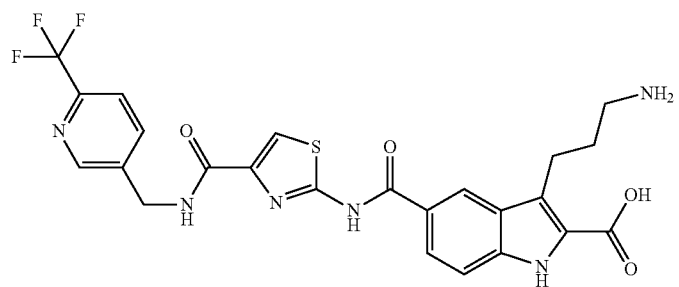

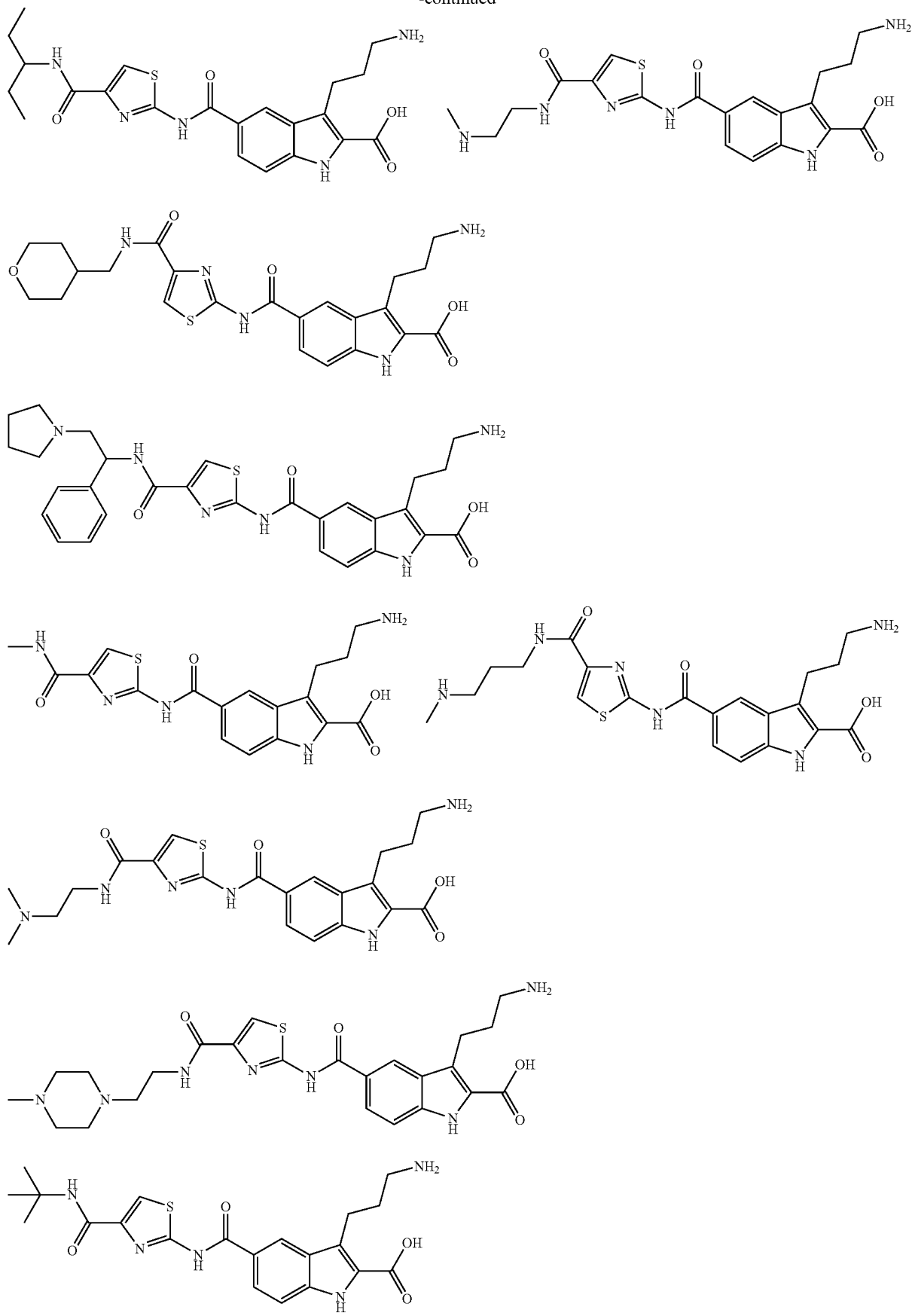

-continued
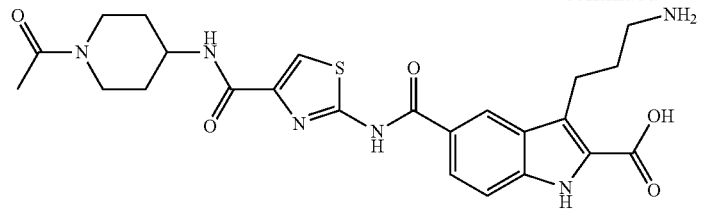
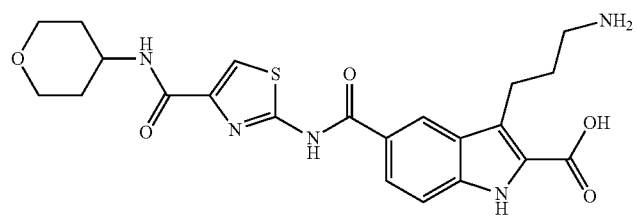
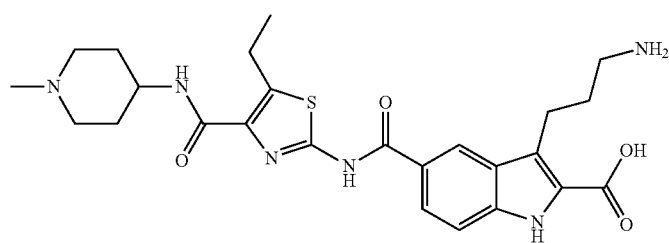
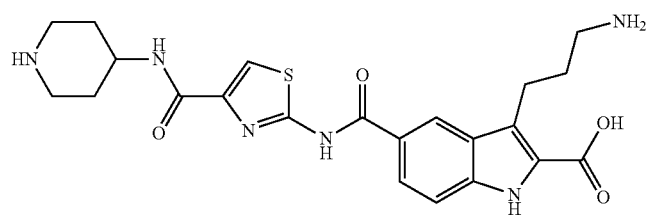
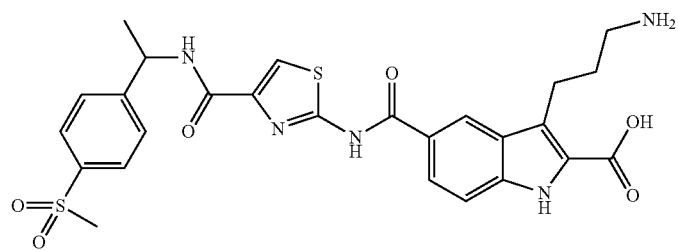
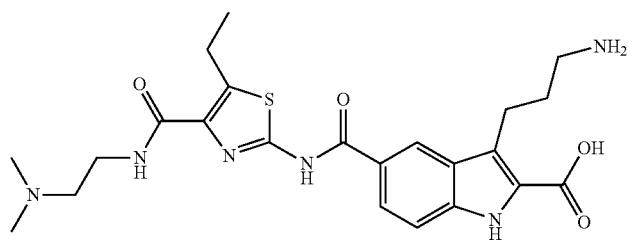
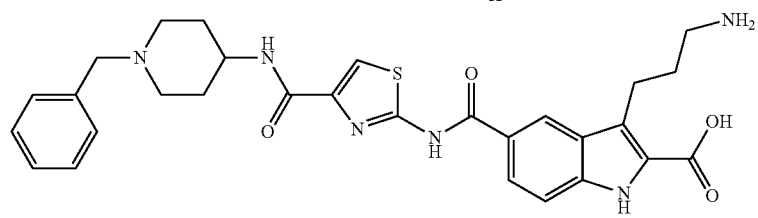

-continued

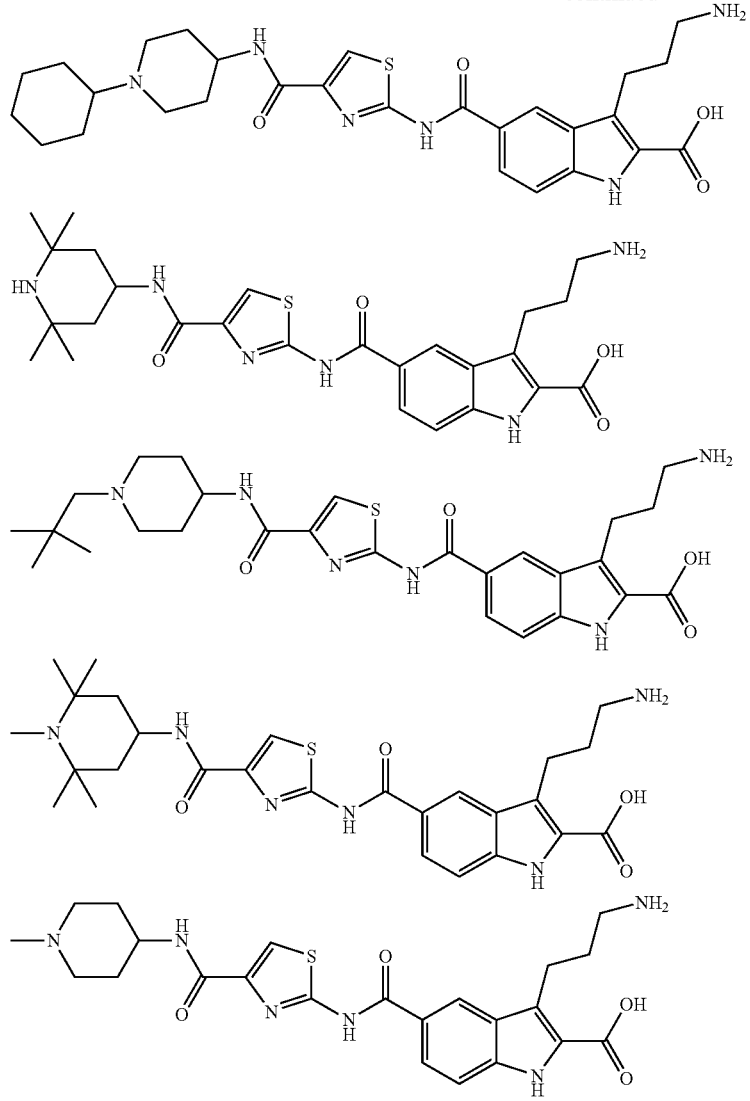

Procedure for the Identification of MAPKAP-k2 Inhibitors

The protein reagents required for the phosphoryl transfer reaction catalyzed by MAPKAP-k2 include 1 nM MAPKAP-k2 (1-400) and 500 nM biotinylated LSP1 (179-339). The MAPKAP-k2 (1-400) splice variant used in the reaction is expressed as an amino-terminal glutathione transferase fusion protein in insect cells, purified by glutathione affinity chromatography and activated with murine p38α (Lukas et al., (2004) Biochemistry 43, 9950-9960). The biotinylated LSP1 (179-339) is prepared from an amino-terminal GST fusion of the carboxy-terminal portion of lymphocyte specific protein 1 (LSP1 179-339), expressed in E. coli and purified by glutathione affinity chromatography (Lukas et al., (2004) Biochemistry 43, 9950-9960). LSP1 (179-339) is covalently modified with iodoacetyl biotin (Pierce Chemicals). The phosphoryl transfer reaction (30 min) is performed in Reacti-Bind NeutrAvidin Coated plates (Pierce Chemicals) in buffer containing 50 mM HEPES (pH 7.6), 50 mM KCl, 10 mM $MgCl_2$, 100 microM $Na_3VO_4$, 0.01% CHAPS, 1 mM DTT, 10 microg/mL bovine serum albumin, 2 microM ATP, 0-30 microM compound and 1-2% DMSO (v/v).

The protein reagent required for detection of MAPKAP-k2 (1-400) dependent phosphorylation of biotinylated LSP1 (179-339) and inhibitors of MAPKAP-k2 (1-400) catalysis is $Eu^{3+}$ chelated anti-phospho-LSP1 IgG1 monoclonal antibody. The anti-phospho-LSP1 IgG1 monoclonal antibody is raised against the following amino acid sequence: CRTP-KLARQA(phospho-S)IELPSM (Anaspec) conjugated to KLH antigen from Pierce Chemicals. The antibody is covalently modified with Eu N1 ITC Chelate from Perkin Elmer Life Sciences. The detection of MAPKAP-k2 (1-400) dependent phosphorylation of LSP1 (179-339) and inhibitors of MAPKAP-k2 (1-400) catalysis is performed by (1) washing the Reacti-Bind NeutrAvidin Coated plates with Delfia Wash Buffer (Perkin Elmer Life Sciences), (2) adding the $Eu^{3+}$ chelated anti-phospho-LSP1 IgG1 monoclonal antibody to the Reacti-Bind NeutrAvidin Coated plates (1 hr), (3) washing the Reacti-Bind NeutrAvidin Coated plates with Delfia Wash Buffer, (4) adding Delfia Enhancement Solution (15 min) from Perkin Elmer Life Sciences, and (5) reading time resolved fluorescence with an excitation maximum of 360 nm and an emission maximum of 620 nm on an LJL Biosystems Analyst instrument.

Inhibition of TNF Production in THP Cells

The inhibition of cytokine production can be observed by measuring inhibition of TNFα in lipopolysaccharide stimulated THP cells. All cells and reagents were diluted in RPMI 1640 with phenol red and L-glutamine, supplemented with additional L-glutamine (total: 4 mM), penicillin and streptomycin (50 units/ml each) and fetal bovine serum (FBS, 3%) (GIBCO, all conc. final). Assay was performed under sterile conditions; only test compound preparation was nonsterile. Initial stock solutions were made in DMSO followed by dilution into RPMI 1640 2-fold higher than the desired final assay concentration. Confluent THP.1 cells ($2\times10^6$ cells/ml, final conc.; American Type Culture Company, Rockville, Md.) were added to 96 well polypropylene round bottomed culture plates (Costar 3790; sterile) containing 125 microl test compound (2 fold concentrated) or DMSO vehicle (controls, blanks) DMSO concentration did not exceed 0.2% final. Cell mixture was allowed to preincubate for 30 min, 37° C., 5% $CO_2$ prior to stimulation with lipopolysaccharide (LPS; 1 microg/ml final; Siga L-2630, from $E.\ coli$ serotype 0111.B4; stored as 1 mg/ml stock in endotoxin screened distilled $H_2O$ at −80° C.). Blanks (unstimulated) received $H_2O$ vehicle; final incubation volume was 250 microl. Overnight incubation (18-24 hr) proceeded as described above. Assay was terminated by centrifuging plates 5 min, room temperature, 1600 rpm (400×g); supernatants were transferred to clean 96 well plates and stored −80° C. until analyzed for human TNFα by a commercially available ELISA kit (Biosource #KHC3015, Camarillo, Calif.). Data was analyzed by non-linear regression (Hill equation) to generate a dose response curve using SAS Software System (SAS institute, Inc., Cary, N.C.). The calculated $IC_{50}$ value is the concentration of the test compound that caused a 50% decrease in the maximal TNFα production.

Lipopolysaccharide (LPS)-Induced TNF-Alpha Production:

B10.RIII mice were obtained from Jackson laboratories, LPS from Sigma Chemical Co. (# L-2880), D-+-galactosamine from Sigma chemical Co. (# G-0500) and Aerrane (isoflurane, USP) from Baxter Pharmaceuticals, NDC 10019-773-40. Animals were weighed and their tails were marked. Mice were anesthetized with isoflurane and their tails were warmed with gauze dipped in hot water prior to challenge. They were challenged with 200 ng of LPS/1 mg galactosamine in 200 uL per mouse delivered intravenously (i.v.) into the tail vein. 1 hour after challenge, the mice were anesthetized with isoflurane and were bled by cardiac punction. Approximately 100 uL were collected. The blood was dispensed into eppendorf tubes treated with EDTA and shaken. This procedure was repeated for all animals. The blood was centrifuged for ~5 minutes at 14,000 rpm in an eppendorf microfuge. The plasma was collected, put into labeled eppendorf tubes and frozen at −20° C. Plasma samples were then assayed for the presence of TNF-alpha using a mouse TNF-alpha ELISA duoset (DY410) kit purchased form R&D systems conducted as per the protocol supplied. Plasma samples are diluted to allow samples to fall on the linear portion of the standard response curve.

Methods of Using the Compounds of the Present Invention

In accordance with the invention, there are provided novel methods for using the compounds of the present invention. The compounds disclosed therein effectively block inflammatory cytokine production from cells. The inhibition of cytokine production is an attractive means for preventing and treating a variety of cytokine mediated diseases or conditions associated with excess cytokine production, e.g., diseases and pathological conditions involving inflammation. Thus, the compounds are useful for the treatment of diseases and conditions as described in the Background section, including the following conditions and diseases:

osteoarthritis, atherosclerosis, contact dermatitis, bone resorption diseases, reperfusion injury, asthma, multiple sclerosis, Guillain-Barre syndrome, Crohn's disease, ulcerative colitis, psoriasis, graft versus host disease, systemic lupus erythematosus and insulin-dependent diabetes mellitus, rheumatoid arthritis, toxic shock syndrome, Alzheimer's disease, diabetes, inflammatory bowel diseases, acute and chronic pain as well as symptoms of inflammation and cardiovascular disease, stroke, myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, syndromes associated with hemodialysis, leukopheresis, granulocyte transfusion associated syndromes, and necrotizing entrerocolitis, complications including restenosis following percutaneous transluminal coronary angioplasty, traumatic arthritis, sepsis, chronic obstructive pulmonary disease and congestive heart failure. The compounds of the invention may also be useful for anticoagulant or fibrinolytic therapy (and the diseases or conditions related to such therapy).

The compounds of the invention will be useful for treating oncological diseases and other cytokine mediated diseases and conditions related to p38 and MK2 as known in the art. These diseases include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma and mesothelioma.

Examples of brain cancers include, but are not limited to brain stem, optic and hypophtalmic glioma, cerebella and cerebral astrocytoma, medulloblastoma, ependymoma, as well as pituitary, neuroectodermal and pineal tumor.

Examples of peripheral nervous system tumors include, but are not limited to neuroblastoma, ganglioneuroblastoma, and peripheral nerve sheath tumors.

Examples of tumors of the endocrine and exocrine system include, but are not limited to thyroid carcinoma, adrenocortical carcinoma, pheochromocytoma, and carcinoid tumors.

Tumors of the male reproductive organs include, but are not limited to prostate and testicular cancer.

Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, and urethral cancers.

Eye cancers include, but are not limited to intraocular melanoma and retinoblastoma.

Examples of liver cancers include, but are not limited to hepatocellular carcinoma (liver cell carcinomas with or without fibrolamellar variant), hepatoblastoma, cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer.

Lymphomas include, but are not limited to AIDS-related lymphoma, non-Hodgkin's lymphoma, Hodgkins lymphoma, cutaneous T-cell lymphoma, and lymphoma of the central nervous system.

Sarcomas include, but are not limited to sarcoma of the soft tissue, osteosarcoma, Ewings sarcoma, malignant fibrous histiocytoma, lymphosarcoma, angiosarcoma, and rhabdomyosarcoma. Leukemias include, but are not limited to acute myeloid leukemia, acute lymphoblastic leukemia, chronic lymphocytic leukemia, chronic myelogenous leukemia, and hairy cell leukemia.

Plasma cell dyscrasias include, but are not limited to multiple myeloma, and Waldenstrom's macroglobulinemia.

These disorders have been well characterized in man, but also exist with a similar etiology in other mammals, and can be treated by pharmaceutical compositions of the present invention.

For therapeutic use, the compounds may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. The above described compounds may be physically combined with the conventional therapeutics or other adjuvants into a single pharmaceutical composition. Reference is this regard may be made to Cappola et al.: U.S. Pat. No. 6,565,880, PCT/US 01/21860 and U.S. application Ser. No. 10/214,782, each incorporated by reference herein in their entirety. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds may be administered separately (either serially or in parallel). Separate dosing allows for greater flexibility in the dosing regime.

As mentioned above, dosage forms of the compounds described herein include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are well in the art known. Dosage levels and requirements are well-recognized in the art and may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. Reference in this regard may also be made to US publication No. US 2003-0118575 A1. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

What is claimed is:

1. A compound having the following formula (I):

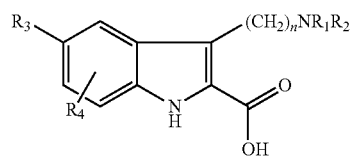

wherein:

$R_1$ and $R_2$ are H or $C_{1-3}$alkyl;

$R_3$ is $C(O)NR_5R_6$ wherein $R_5$ is hydrogen, $C_{1-6}$ alkyl, $C_{2-6}$ alkenyl, $C_{2-6}$ alkynyl, $C_{1-6}$ alkoxy, or $C_{3-7}$ cycloalkyl; and $R_6$ is hydrogen, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, hydroxy, $C_{3-7}$ cycloalkyl, heterocyclyl, aryl, aryloxy, acyl, heteroaryl, $C_{3-7}$ cycloalkyl -$C_{1-6}$ alkyl, aryl-$C_{1-6}$ alkyl, aryl-$C_{1-6}$ haloalkyl, heterocyclyl-$C_{1-6}$ alkyl, heteroaryl-$C_{1-6}$ alkyl, $C_{3-7}$ cycloalkyl-$C_{2-6}$ alkenyl, aryl-$C_{2-6}$ alkenyl, heterocyclyl-$C_{2-6}$ alkenyl, heteroaryl-$C_{2-6}$ alkenyl, di$C_{1-3}$ alkylamino$(CH_2)_{2-4}$, or $C_{2-6}$ alkylthio, wherein the sulfur atom is optionally oxidized to a sulfoxide or sulfone; wherein each aryl, heterocycle or heteroaryl may be singly or multiply substituted with $R^y$, wherein $R^y$ is chosen from:

halogen, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, hydroxy, $C_{3-7}$ cycloalkyl, heterocyclyl, aryl optionally substituted with $R^x$, aryloxy, acyl, heteroaryl optionally substituted with $R^x$, $C_{3-7}$ cycloalkyl —$C_{1-6}$ alkyl, aryl-$C_{1-6}$ alkyl, aryl-$C_{1-6}$ haloalkyl, aryl-$C_{1-6}$aminoalkyl, heterocyclyl-$C_{1-6}$ alkyl, heteroaryl-$C_{1-6}$ alkyl, $C_{3-7}$ cycloalkyl-$C_{2-6}$ alkenyl, aryl-$C_{2-6}$ alkenyl, heterocyclyl-$C_{2-6}$ alkenyl, heteroaryl-$C_{2-6}$ alkenyl, $C_{2-6}$ alkylthio wherein the sulfur atom is optionally oxidized to a sulfoxide or sulfone, —$OCF_3$, amino, $C_{1-3}$alkylamino, di$C_{1-3}$alkylamino, acylamino, hydroxyethylamino, —CN, —$CO_2C_{1-3}$ alkyl, —$CH_2NH_2$, —$C(O)N(R^a)(R^b)$ where $R^a$ and $R^b$ are independently selected from H, $C_{1-3}$alkyl, —$CH_2C(O)NH_2$, —$(CH_2)_nOH$, —$(CH_2)_nNR^cR^d$, where n is 2 or 3 and $R^c$ and $R^d$ are independently selected from H, $C_{1-3}$alkyl and $C(O)CH_3$, or —$C(O)NH-N=C-R^e$, where $R^e$ is aryl or heteroaryl optionally substituted with $R^x$, or $R^a$ and $R^b$ together with the N they are connected to form a pyrrolidine, piperazine, piperidine or morpholine ring optionally substituted with one to three groups selected from —$CO_2C_{1-3}$alkyl, —$C(O)NH_2$, —OH, $C_{1-3}$alkyl, amino, $C_{1-3}$alkylamino and di$C_{1-3}$alkylamino; or $R_5$ and $R_6$ are taken together with the nitrogen they are connected to form a heterocyclyl ring;

$R_4$ is selected from H, $C_{1-6}$alkyl, halogen and $CF_3$;

$R^x$ selected from:

amino, $C_{1-6}$ alkyl, $C_{2-6}$ alkenyl, amino $C_{1-6}$ alkyl, hydroxy$C_{1-6}$ alkyl, cyano $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, hydroxy, $C_{3-7}$ cycloalkyl, heterocyclyl, aryl, aryloxy, acyl, heteroaryl, $C_{3-7}$ cycloalkyl-$C_{1-6}$ alkyl, aryl -$C_{1-6}$ alkyl, aryl-$C_{1-6}$ haloalkyl, heterocyclyl-$C_{1-6}$ alkyl, heteroaryl-$C_{1-6}$ alkyl, $C_{3-7}$ cycloalkyl -$C_{2-6}$ alkenyl, aryl-$C_{2-6}$ alkenyl, heterocyclyl-$C_{2-6}$ alkenyl, heteroaryl-$C_{2-6}$ alkenyl, carbonyl, carbamoyl, ureido, or $C_{2-6}$ alkylthio wherein the sulfur atom is oxidized to a sulfoxide or sulfone; and n is 3.

2. The compound of claim 1 wherein $R_1$ and $R_2$ are H;

$R_4$ is H; and, $R^x$ is selected from: amino $C_{1-6}$ alkyl, $C_{2-6}$ alkenyl, amino $C_{1-6}$ alkyl, hydroxy $CC_{1-6}$ alkyl, cyano $CC_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, hydroxy, $C_{3-7}$ cycloalkyl, acyl, $C_{3-7}$ cycloalkyl-$C_{1-6}$ alkyl, $C_{3-7}$ cycloalkyl-$C_{2-6}$ alkenyl, carbonyl, carbamoyl and $CO_2C_{1-6}$alkyl.

3. The compound of claim 1 wherein $R_1$ and $R_2$ are H;

$R_3$ is —C(O)NR$_5$R$_6$ wherein $R_5$ is hydrogen; and $R_6$ is chosen from hydrogen, $C_{1-6}$ alkyl, $C_{3-7}$ cycloalkyl, heterocyclyl, aryl, heteroaryl, $C_{3-7}$ cycloalkyl -$C_{1-6}$ alkyl, aryl-$C_{1-6}$ alkyl, heterocyclyl-$C_{1-6}$ alkyl, heteroaryl-$C_{1-6}$ alkyl, or $(CH_3)_2NCH_2CH_2$—, wherein each aryl, heterocycle or heteroaryl may be singly or multiply substituted with $R^y$, wherein $R^y$ is chosen from: halogen, $C_{1-6}$ alkyl, $C_{2-6}$ alkenyl, $C_{2-6}$ alkynyl, $C_{1-6}$ alkoxy, hydroxy, $C_{3-7}$ cycloalkyl, acyl, $C_{3-7}$ cycloalkyl -$C_{1-6}$ alkyl, aryl-$C_{1-6}$ alkyl, aryl-$C_{1-3}$ aminoalkyl, heterocyclyl-$C_{1-6}$ alkyl, heteroaryl-$C_{1-6}$ alkyl, $C_{2-6}$ alkylthio wherein the sulfur atom is optionally oxidized to a sulfoxide or sulfone, —OCF$_3$, amino, $C_{1-3}$alkylamino, di$C_{1-3}$alkylamino, acylamino, hydroxyethylamino, —CN, —CO$_2$C$_{1-3}$alkyl, —CH$_2$NH$_2$, —C(O)N(R$^a$)(R$^b$) where $R^a$ and $R^b$ are independently selected from H, $C_{1-3}$alkyl, —CH$_2$C(O)NH$_2$, —(CH$_2$)$_n$OH, or —(CH$_2$)$_n$NR$^c$R$^d$, and $R^c$ and $R^d$ are independently selected from H, $C_{1-3}$alkyl and C(O)CH$_3$;

$R_4$ is H; and $R^x$ is selected from: amino $C_{1-6}$ alkyl, $C_{2-6}$ alkenyl, amino $C_{1-6}$ alkyl, hydroxy $C_{1-6}$ alkyl, cyano $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, hydroxy, $C_{3-7}$ cycloalkyl, acyl, $C_{3-7}$ cycloalkyl—$C_{1-6}$ alkyl, $C_{3-7}$ cycloalkyl-$C_{2-6}$ alkenyl, carbonyl, carbamoyl and $CO_2C_{1-6}$alkyl.

4. A pharmaceutical composition comprising a compound of claim 1 together with a pharmaceutically acceptable carrier or excipient.

* * * * *